United States Patent
Maelicke

(10) Patent No.: US 10,265,325 B2
(45) Date of Patent: *Apr. 23, 2019

(54) CHOLINERGIC ENHANCERS WITH IMPROVED BLOOD-BRAIN BARRIER PERMEABILITY FOR THE TREATMENT OF DISEASES ACCOMPANIED BY COGNITIVE IMPAIRMENT

(71) Applicant: NEURODYN LIFE SCIENCES INC., Charlottetown (CA)

(72) Inventor: Alfred Maelicke, Nieder-Olm (DE)

(73) Assignee: Neurodyn Life Sciences Inc., Charlottetown (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/699,626

(22) Filed: Sep. 8, 2017

(65) Prior Publication Data

US 2018/0008613 A1    Jan. 11, 2018

Related U.S. Application Data

(60) Continuation of application No. 13/861,134, filed on Apr. 11, 2013, now Pat. No. 9,763,953, which is a division of application No. 12/422,901, filed on Apr. 13, 2009, now abandoned, which is a continuation-in-part of application No. 12/067,799, filed as application No. PCT/EP2006/009220 on Sep. 22, 2006, now abandoned, said application No. 12/422,901 is a continuation-in-part of application No. 11/683,148, filed on Mar. 7, 2007, now abandoned.

(60) Provisional application No. 60/780,243, filed on Mar. 7, 2006, provisional application No. 61/046,683, filed on Apr. 21, 2008.

(30) Foreign Application Priority Data

Sep. 22, 2005   (EP) .................................. 05020721

(51) Int. Cl.
  *A61K 31/55*    (2006.01)
  *C07D 307/91*   (2006.01)
  *C07D 405/12*   (2006.01)
  *C07D 491/06*   (2006.01)
  *C07F 9/6561*   (2006.01)

(52) U.S. Cl.
  CPC ............ *A61K 31/55* (2013.01); *C07D 307/91* (2013.01); *C07D 405/12* (2013.01); *C07D 491/06* (2013.01); *C07F 9/6561* (2013.01); *Y02A 50/465* (2018.01)

(58) Field of Classification Search
  CPC .... A61K 31/55; C07D 307/91; C07D 405/12; C07D 491/06; C07F 9/6561; Y02A 50/465
  See application file for complete search history.

(56) References Cited

U.S. PATENT DOCUMENTS

| | | | |
|---|---|---|---|
| 5,250,287 A * | 10/1993 | Cocozza | A61M 15/0065 128/203.21 |
| 6,150,354 A | 11/2000 | Davis et al. | |
| 6,638,925 B2 | 10/2003 | Czollner et al. | |
| 2003/0162770 A1 | 8/2003 | Davis | |
| 2004/0266659 A1 | 12/2004 | Laberge | |
| 2005/0026979 A1 | 2/2005 | Ghazzi et al. | |
| 2005/0065176 A1 | 3/2005 | Field et al. | |
| 2009/0253654 A1 | 10/2009 | Maelicke | |

FOREIGN PATENT DOCUMENTS

| | | |
|---|---|---|
| EP | 0384676 A1 | 8/1990 |
| EP | 0515301 A2 | 11/1992 |
| EP | 0 649 846 A1 | 4/1995 |

(Continued)

OTHER PUBLICATIONS

Albuquerque, et al. 1995 "Nicotinic Receptor Function in the Mammalian Central Nervous System" *Annals New York Academy of Sciences*, 757: 48-72.

(Continued)

*Primary Examiner* — Sarah Pihonak

(74) *Attorney, Agent, or Firm* — Knobbe, Martens, Olson & Bear LLP

(57) ABSTRACT

A method for the treatment of a neurodegenerative, psychiatric or neurological disease associated with a cholinergic deficit comprising administering GLN-1062 or a pharmaceutically acceptable salt thereof by nasal administration to a patient in need thereof.

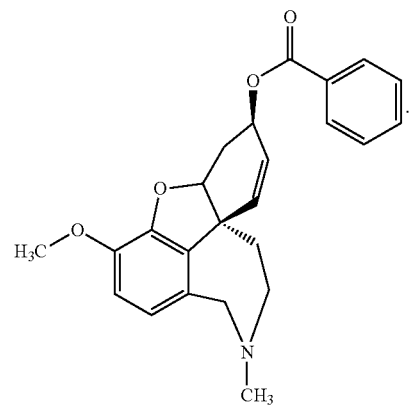

GLN-1062

8 Claims, 29 Drawing Sheets

(56) References Cited

FOREIGN PATENT DOCUMENTS

| EP | 0648771 A1 | 4/1995 |
|---|---|---|
| EP | 0653427 A1 | 5/1995 |
| EP | 1020470 A2 | 7/2000 |
| EP | 1777222 A1 | 4/2007 |
| JP | 2003-026683 | 1/2003 |
| WO | WO 88/08708 A1 | 11/1988 |
| WO | WO 97/40049 A1 | 10/1997 |
| WO | WO 99/08672 A1 | 2/1999 |
| WO | WO 99/21561 A1 | 5/1999 |
| WO | WO 00/30446 A1 | 6/2000 |
| WO | WO 00/32199 A1 | 6/2000 |
| WO | WO 00/33840 A1 | 6/2000 |
| WO | WO 01/43697 A2 | 6/2001 |
| WO | WO 01/74820 A1 | 10/2001 |
| WO | WO 2004/014393 A1 | 2/2004 |
| WO | WO 2005/027975 A1 | 3/2005 |
| WO | WO 2005/030332 A2 | 4/2005 |
| WO | WO 2005/030333 A2 | 4/2005 |
| WO | WO 2005/030713 A2 | 4/2005 |
| WO | WO 2005/041979 A1 | 5/2005 |
| WO | WO 2005/072713 A2 | 8/2005 |
| WO | WO 2005/074535 A2 | 8/2005 |
| WO | WO 2014/016430 A1 | 1/2014 |

OTHER PUBLICATIONS

Albuquerque, et al. 1997 "Minireview: Nicotinic Acetylcholine Receptors on Hippocampal Neurons: Distribution on the Neuronal Surface and Modulation of Receptor Activity" *Journal of Receptors and Signal Transduction Research* 17(1-3): 243-266.

Albuquerque, et al. 1997 "Properties of Neuronal Nicotinic Acetylcholine Receptors: Pharmacological Characterization and Modulation of Synaptic Function" *Journal of Pharmacology and Experimental Therapeutics* 280(3): 1117-1136.

Alkondon, et al. 1997 "Choline is a Selective Agonist of α7 Nicotinic Acetylcholine Receptors in the Rat Brain Neurons" *European Journal of Neuroscience* 9: 2734-2742.

Alkondon, et al. 2000 "α7 nicotinic acetylcholine receptors and modulation of gabaergic synaptic transmission in the hippocampus" *European Journal of Pharmacology* 393: 59-67.

Arias, et al. 2005 "Unequal neuroprotection afforded by the acetylcholinesterase inhibitors galantamine, Donepezil, and Rivastigmine in SH-SY5Y neuroblastoma cells: Role of nicotinic receptors" *The Journal of Pharmacology and Experimental Therapeutics* 315(3): 1346-1353.

Aronson, et al. 2009 "Optimal dosing of Galantamine in patients with mild or moderate Alzheimer's disease" *Drugs Aging* 20(3): 231-239.

Baakman, A.C. et al. "Pharmocokinetics, safety and pharmacodynamics of Memogain, a new prodrug of galantamine, in healthy subjects" CHDR Poster, Received in the EPO on Nov. 18, 2014.

Baakman, et al. 2016 "First in human study with prodrug of galantamine: Improved benefit-risk ratio?" *Alzheimer's & Dementia: Translational Research & Clinical Interventions*: 1-10.

Banks, W.A. 2008 "Developing drugs that can cross the blood-brain barrier: applications to Alzheimer's disease" *BMC Neuroscience* 9(Suppl. 3):S2, pp. 1-4.

Barnes, et al. 2000 "Chronic treatment of old rats with donepezil or galantamine: Effects on memory, hippocampal plasticity and nicotinic receptors" *Neuroscience* 99(1): 17-23.

Bickel, et al. 1991 "Galanthamine: Pharmacokinetics, tissue distribution and cholinesterase inhibition in brain of mice" Neuropharmacology 30(5): 447-454.

Böhm, H.-J. et al. 2004 "Fluorine in Medicinal Chemistry" *ChemBioChem* 5: 637-643.

Bores, G. and Kosley Jr., R.W. (1996) "Galanthmine derivatives for the treatment of Alzheimer's disease" *Drugs of the Future* 21: 627-636.

Bores, G. et al. (1996) "Pharamacological Evaluation of Novel Alzheimer's Disease Therapeutics: Acetylcholinesterase Inhibitors Related to Galanthamine" *The Journal of Pharmacology and Experimental Therapeutics* 277: 728-738.

Brodaty, H. et al. 2005 "Galantamine Prolonged-Release formulation in the treatment of mild to moderate Alzheimer's Disease" Dement Geriatr Cogn Disord 20: 120-132.

De Jonge, et al. 2007 "The alpha7 nicotinic acetylcholine receptor as a pharmacological target for inflammation" *British Journal of Pharmacology* 151: 915-929.

Deutsch, et al. 2013 "Targeting alpha-7 nicotinic neurotransmission in schizophrenia: A novel agonist strategy" *Schizophr Res.* 148: 138-144.

Dunbar, et al. 2006 "Post hoc comparison of daily rates of nausea and vomiting with once- and twice-daily galantamine from a double-blind, placebo-controlled, parallel-group, 6-month study" *Clinical Therapeutics* 28(3): 365-372.

Ferrari, et al. 1999 "Changes in nicotinic acetylcholine receptor subunit mRNAs and nicotinic binding in spontaneously hypertensive stroke prone rats" *Neuroscience Letters* 277: 169-172.

Fonck, et al. 2003 "Increased sensitivity to agonist-induced seizures, straub tail, and hippocampal theta rhythm in knock-in mice carrying hypersensitive α4 nicotinic receptors" The Journal of Neuroscience 23(7): 2582-2590.

Francis, et al. 1999 "The cholinergic hypothesis of Alzheimer's disease: a review of progress" *Journal of Neurol Neurosurg Psychiatry* 66: 137-147.

Froestl, et al. 2014 "Cognitive Enhancers (Nootropics). Part 1: Drugs interacting with receptors. Update 2014" *Journal of Alzheimer's Disease* 41: 961-1019.

Griffith et al. 2007 "The safety and efficacy of galantamine in patients with partial epilepsy and memory difficulties" *Epilepsia* 48(6): 222.

Han, S.-Y. et al. 1991 "Synthesis and biological activity of galanthamine derivatives as acetylcholinesterase (AChE) inhibitors" *Bioorganic & Medical Chemistry Letters* 11:579-580.

Han, S.Y. et al. (1992) "Chemical and pharmacological characterization of galantamine, an acetylcholinesterase inhibitor, and its derivatives. A potential application in Alzheimer's disease?" *Eur J Med Chem* 27: 673-687.

Haroutunian, et al. 1985 "Pharmacological alleviation of cholinergic lesion induced memory deficits in rats" Life Sciences 37: 945-952.

Irvine, G.B. et al. 2008 "Protein Aggregation in the Brain: The Molecular Basis for Alzheimer's and Parkinson's Diseases" *Mol Med* 14(7-8) 451-464.

Kewitz, et al. 1994 "Galanthamine in Alzheimer's disease" in Alzheimer Diseases: Therapeutic Strategies, H. Giacobiol and R. Becker eds. (in 5 pages).

Leiser, et al. 2009 "A cog in cognition: How the α7 nicotinic acetylcholine receptor is geared towards improving cognitive deficits" *Pharmacology & Therapeutics* 122: 302-311.

Leonard, et al. 2007 "In vitro formulation optimization of intranasal galantamine leading to enhanced bioavailability and reduced emetic response in vivo" *International Journal of Pharmaceutics* 335: 138-146.

Lindvall & Kokaia 2006 "Stem cells for the treatment of neurological disorders" *Nature* 441: 1094-1096.

Maelicke, et al. 1995 "Minireview: Noncompetitive Agonism at Nicotinic Acetylcholine Receptors; Functional Significance for CNS Signal Transduction" *Journal of Receptors and Signal Transduction* 15(1-4): 333-353.

Maelicke, et al. 1996 "New approach to drug therapy in Alzheimer's dementia" *Drug Discovery Today* 1(2): 53-59.

Mann et al. 2006 "Galantamine: a cholinergic patch in the treatment of alcoholism: a randomized, placebo-controlled trial" *Psychopharmacology* 184: 115-121.

Mannens, G.S.J. et al. 2002 "The metabolism and excretion of galantamine in rats, dogs, and humans" *Drug Metablolism and Disposition* 30(5):553-563.

Maelicke, et al. 2009 "Memogain is a galantamine pro-drug having dramatically reduced adverse effects and enhanced efficacy" *J Mol Neurosci*: (in 3 pages).

(56) References Cited

OTHER PUBLICATIONS

Maelicke 2011 "Memogain, a pleasant, highly potent and neuroprotective novel drug treatment in Alzheimer's disease" Alzheimer's & Dementia vol. 7(4): p. S799, Poster Presentation P4-265.

Martin, et al. 2007 "Schizophrenia and the α7 nicotinic acetylcholine receptor" *International Review of Neurobiology* 78: 225-246.

Molliver, et al. 1987 "Serotonergic neuronal systems: What their anatomic organization tells us about function" *Journal of Clinical Psychopharmacology* 7(6): 3S-23S.

Neurodyn Interim Report on Part 1 of Memogain Phase 1A Clinical trial, published Jan. 13, 2014; on the internet at: neurodyn-inc.com/neurodyn-inc-completes-part-i-of-memogain-phase-ia-clinical-trial/.

O'Brien, et al. 1993 "Letters to the editor—Age-Associated Memory Impairment" *International Journal of Geriatric Psychiatry* 8: 779-884.

Oral Proceedings in European Patent—Documents Submitted (European Application No. 08735211.8), dated Feb. 19, 2014.

Oral Proceedings in European Patent—Minutes (European Patent No. 2137192), dated May 15, 2017.

Oral Proceedings in European Patent—Decision From Boards of Appeal of the European Patent Office (European Patent No. 2137192), dated Aug. 8, 2017.

Perry, et al. 1995 "Alteration in nicotine binding sites in Parkinson's Disease, Lewy body dementia and Alzheimer's Disease: Possible index of early neuropathology" *Neuroscience* 64(2): 385-395.

Petit, TL 1988 "The neurobiology of learning and memory: elucidation of the mechanisms of cognitive dysfunction" *NeuroToxicology* 9: 413-428.

Popa, R.V. et al. (2004) "Differential Effects of Galantaminone and Galantamine N-Butylcarbamate on α7 Nicotinic Acetylcholine Receptors in Hippocampal Neurons" *Neurobiology of Aging* vol. 25, Suppl 2, p. S217 (Poster P1-417).

Raskind, et al. 2000 "Galantamine in AD—A 6-month randomized, placebo-controlled trial with a 6-month extension" *Neurology* 54: 2261-2268.

Santos, et al. 2002 "The Nicotinic Allosteric Potentiating Ligand Galantamine Facilitates Synaptic Transmission in the Mammalian Central Nervous System" *Molecular Pharmacology* 61(5): 1222-1234.

Schilström, B. et al. 2007 "Galantamine Enhances Dopaminergic Neurotransmission In Vivo Via Allosteric Potentiation of Nicotinic Acetylcholine Receptors" *Neuropsychopharmacology* 32: 43-53.

Schrattenholz, et al. 1996 "Agonist responses of neuronal nicotinic acetylcholine receptors are potentiated by a novel class of allosterically acting ligands" *Molecular Pharmacology* 49:1-6.

Schröder, et al. 1991 "Nicotinic cholinoceptive neurons of the frontal cortex are reduced in Alzheimer's Disease" *Neurobiol Aging* 12(3): 259-262.

Schröder, et al. 1995 "Gene expression of the nicotinic acetylcholine receptor α4 subunit in the frontal cortex in Parkinson's disease patients" *Neuroscience Letters* 187: 173-176.

Singh et al. 2007 "Advances in the treatment of Parkinson's disease" *Progress in Neurobiology* 81: 29-44.

Stedman's Medical Dictionary Definition of Myopathy, 2000 Lippincott Williams & Wilkins.

Steinlein, et al. 1995 "A missense mutation in the neuronal nicotinic acetylcholine receptor α4 subunit is associated with autosomal dominant nocturnal frontal lobe epilepsy" *Nature Genetics* 11: 201-203.

Togashi, et al. 1994 "Neurochemical profiles in cerebrospinal fluid of stroke-prone spontaneously hypertensive rats" *Neuroscience Letters* 166: 117-120.

Vinogradova, O.S. et al. 1998 "Pacemaker neurons of the forebrain medial septal area and theta rhythm on the hippocampus" *Membr Cell Biol* 11: 715-725.

Wevers, A. et al. 1998 "Nicotinic receptors in Alzheimers disease—from autopsy studies to organotypic culture models" *Int J Geriatric Psychopharmacol* 1: 158-163.

Wilcock, et al. 2000 "Efficacy and safety of galantamine in patients with mild to moderate Alzheimer's disease: multicentre randomised controlled trial" *BMJ* 321: 1-7.

Wilkinson, et al. 2001 "Galantamine: a randomized, double-blind, dose comparison in patients with Alzheimer's disease" *International Journal of Geriatric Psychiatry* 16: 852-857.

Wonnacott 1997 "Presynaptic nicotinic ACh receptors" *Trends in Neurosciences* 20(2): 92-98.

Zhang, L. et al. 2004 "Cholinergic drugs for Alzheimer's Disease enhance in vitro dopamine release" *Molecular Pharmacology* 66:538-544.

Zhao, Q. et al. 2005 "Pharmacokinetics of extended-release and immediate-release formulations of galantamine at steady state in healthy volunteers" Current Medical Research and Opinion 21: 1547-1554.

Baakman, et al. 2016 "First in human study with prodrug of galantamine: Improved benefit-risk ratio?" *Alzheimer's & Dementia: Translational Research & Clinical Interventions* 2(1): 13-22.

\* cited by examiner

| No. | STRUCTURE | logP | Example |
|---|---|---|---|
| 1 | 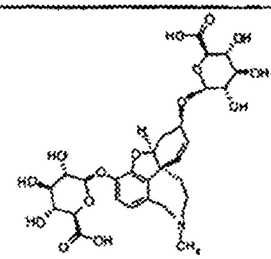 | -3.08 | 9 |
| 2 | 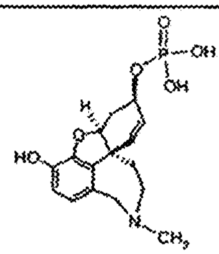 | -0.69 | |
| 3 | 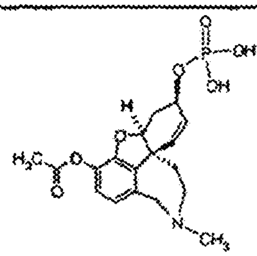 | -0.38 | |
| 4 | 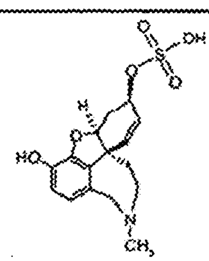 | -0.33 | |
| 5 | 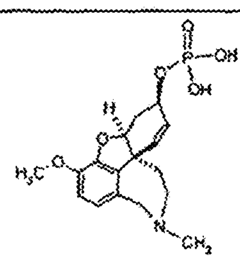 | -0.22 | |

| 6 |  | -0.02 | |
| 7 |  | 0.14 | 24 |
| 8 |  | 0.51 | 23 |
| 9 |  | 0.77 | |
| 10 |  | 0.82 | |
| 11 |  | 0.83 | |

| 12 |  | 0.83 | |
| 13 |  | 0.89 | |
| 14 |  | 0.98 | |
| 15 |  | 1.25 | 11 |
| 16 |  | 1.28 | |
| 17 |  | 1.30 | Galanthamine mentioned here just for comparison |

| | | | |
|---|---|---|---|
| 18 |  | 1.57 | |
| 19 |  | 1.63 | |
| 20 |  | 1.64 | 1 |
| 21 |  | 1.68 | |
| 22 |  | 1.72 | |
| 23 |  | 1.80 | |

| | | | |
|---|---|---|---|
| 24 |  | 1.82 | |
| 25 |  | 1.87 | |
| 26 |  | 1.87 | |
| 27 |  | 1.96 | 2 |
| 28 |  | 2.04 | |
| 29 |  | 2.05 | |

| 30 |  | 2.09 | 5 |
|----|----|------|---|
| 31 |  | 2.26 | |
| 32 |  | 2.27 | |
| 33 |  | 2.33 | 7 |
| 34 |  | 2.37 | |
| 35 |  | 2.39 | |

| | | | |
|---|---|---|---|
| 36 |  | 2.42 | |
| 37 |  | 2.44 | 4 |
| 38 |  | 2.45 | |
| 39 |  | 2.55 | |
| 40 |  | 2.62 | 10 |
| 41 |  | 2.63 | 17 |

| | | | |
|---|---|---|---|
| 42 |  | 2.66 | 6 |
| 43 |  | 2.76 | 21 |
| 44 |  | 2.81 | |
| 45 |  | 2.89 | 18 |
| 46 |  | 2.90 | |
| 47 |  | 2.94 | |

| 48 |  | 3.15 | |
| 49 |  | 3.31 | |
| 50 |  | 3.36 | |
| 51 |  | 3.36 | 19 |
| 52 |  | 3.68 | |
| 53 |  | 3.67 | 3 |

| | | | |
|---|---|---|---|
| 54 |  | 3.69 | |
| 55 |  | 3.93 | |
| 56 |  | 3.95 | |
| 57 |  | 3.99 | |
| 58 |  | 3.99 | |
| 59 |  | 4.07 | 8 |

| 60 |  | 4.09 | |
| 61 |  | 4.23 | 15 |
| 62 |  | 4.77 | 13 |
| 63 |  | 4.78 | 16 |
| 64 |  | 4.83 | 12 |
| 65 |  | 6.34 | 14 |

| | | |
|---|---|---|
| 66 |  | 7.00 |
| 67 |  | 10.61 |
| 68 |  | -1.32 |
| 69 |  | -0.58 |
| 70 |  | -0.50 |
| 71 |  | -0.24 |

| 72 |  | −0.05 | |
| 73 |  | 0.08 | |
| 74 |  | 0.45 | |
| 75 |  | 0.45 | |
| 76 |  | 0.54 | |
| 77 |  | 0.77 | |

| | | | |
|---|---|---|---|
| 78 | | 0.83 | |
| 79 | | 0.83 | |
| 80 | | 1.05 | |
| 81 | | 1.14 | |
| 82 | | 1.15 | |
| 83 | | 1.15 | |

Fig. 1 (continued)

| 84 |  | 1.36 | |
| 85 |  | 1.38 | |
| 86 |  | 1.49 | |
| 87 |  | 1.68 | |
| 88 |  | 1.71 | |
| 89 |  | 1.72 | |

| | | | |
|---|---|---|---|
| 90 | | 1.73 | |
| 91 | | 1.76 | |
| 92 | | 1.81 | |
| 93 | | 1.84 | |
| 94 | | 1.99 | |
| 95 | | 2.14 | 22 |

Fig. 1 (continued)

| 96 |  | 2.14 | |
| 97 |  | 2.15 | |
| 98 |  | 2.20 | |
| 99 |  | 2.27 | |
| 100 |  | 2.35 | |
| 101 |  | 2.38 | |

| | | |
|---|---|---|
| 102 |  | 2.89 |
| 103 |  | 2.97 |
| 104 |  | 3.07 |
| 105 |  | 3.27 |
| 106 |  | 3.33 |
| 107 |  | 3.88 |

| 108 | | 4.09 | |
| 109 | | 4.13 | |
| 110 | | 4.19 | |
| 111 | | 4.19 | |
| 112 | | 4.26 | |
| 113 | | 4.29 | |

Fig. 1 (continued)

| | | |
|---|---|---|
| 114 | | 4.31 |
| 115 | | 4.67 |
| 116 | | 4.98 |
| 117 | | 5.68 |
| 118 | | 5.86 |
| 119 | | 6.08 |

Fig. 1 (continued)

| 120 |  | 6.36 | |
| 121 |  | 7.42 | |
| 122 |  | 7.80 | |
| 123 |  | 7.81 | |
| 124 |  | 9.75 | |
| 125 |  | 11.70 | |

A. *Preparation of STD, QC and Study Samples*

---

To 50µL of blood/brain homogenate study/spiked sample 150µL of cold acetonitrile containing Metoprolol (100.03ng/mL) was added
↓
Vortexed for 30 seconds.
↓
Centrifuged at 13000 rpm for 10 min at 4 °C
↓
100 µL of supernatant diluted with 100µL of milli-Q water
↓
Vortexed and transferred into pre-labeled auto sampler vials.

---

B. *Preparation of Calibration Curve Standards for Recovery*

---

To 50µL of blank blood/brain homogenate 150µL of cold acetonitrile containing Metoprolol (100.03ng/mL) was added
↓
Vortexed for 30 seconds.
↓
Centrifuged at 13000 rpm for 10 min at 4 °C
↓
Separate the supernant
↓
Add 2µL of Spiking solution-II to 198 µL of above supernant and vortex
↓
100 µL of above mixture diluted with 100µL of milli-Q water
↓
Vortexed and transferred into pre-labeled auto sampler vials

CHOLINERGIC ENHANCERS WITH IMPROVED BLOOD-BRAIN BARRIER PERMEABILITY FOR THE TREATMENT OF DISEASES ACCOMPANIED BY COGNITIVE IMPAIRMENT

BACKGROUND OF THE INVENTION

Field of the Invention

The disclosure refers to compounds that, in addition to enhancing the sensitivity to acetylcholine and choline, and to their agonists, of neuronal cholinergic receptors, and/or acting as cholinesterase inhibitors and/or neuroprotective agents, have enhanced blood-brain barrier permeability in comparison to their parent compounds. The compounds are derived (either formally by their chemical structure or directly by chemical synthesis) from natural compounds belonging to the class of amaryllidaceae alkaloids e.g., Galantamine, Narwedine and Lycoramine, or from metabolites of said compounds. The compounds of the present invention can either interact as such with their target molecules, or they can act as "pro-drugs", in the sense that after reaching their target regions in the body, they are converted by hydrolysis or enzymatic attack to the original parent compound and react as such with their target molecules, or both. The compounds of this disclosure may be used as medicaments for the treatment of human brain diseases associated with a cholinergic deficit, including the neurodegenerative diseases Alzheimer's and Parkinson's disease and the neurological/psychiatric diseases vascular dementia, schizophrenia and epilepsy. Galantamine derivatives disclosed herein have higher efficacy and lower levels of adverse side effects in comparison to galantamine, in treatment of human brain diseases.

Description of the Related Art

The diffusion of compounds from the blood plasma into the brain is complicated by the presence of the blood-brain barrier that is a membrane that segregates the brain interstitial fluid from the circulating blood. In designing drugs active in the central nervous system and able to cross the blood-brain barrier, one can exploit endogenous active mechanisms, utilize proper delivery techniques or modify the chemical structure through the synthesis of pro-drug derivatives.

Galantamine is an alkaloid that can be isolated from the bulbs of various snowdrop (*Galanthus*) and *narcissus* species (daffodils, Amaryllidaceae), and recently in particularly high concentrations from *Lycoris radiata*, and related species. Synthetic Galantamine hydrobromide is manufactured by, among other companies, Sanochemia and Janssen Pharmaceutica. The drug has been approved in more than 70 nations for the treatment of mild-to-moderate Alzheimer's disease (AD), a neurodegenerative brain disease. Extensive studies of the pharmacokinetic profile, tissue distribution and accumulation of Galantamine in mice, rats, rabbits and dogs have shown that Galantamine given orally is by no means preferentially distributed to the brain where it is supposed to exert its therapeutic activity in said brain diseases. In contrast, it is accumulated at much higher concentrations in other body tissues. In male and female rat tissues the highest concentrations are observed in kidney (tissue to plasma ratio; T/P ~10-15), salivary and adrenal gland (T/P ~7-14), female rat spleen (T/P ~20), lung, liver, heart, skeletal muscle and testes (T/P ~2-4). In contrast, the brain to plasma ratio is only T/P ~1.5. Similarly, the brain/plasma partition coefficient Kbrain is significantly lower than most other Korgan of Galantamine.

Limited penetration ability of Galantamine through the blood-brain barrier (BBB) into the central nervous system (CNS) is indicated also by the compound's log P value of 1.3, log P being defined as the decadic logarithm of the partition coefficient P which is the ratio of the concentration of compound in aqueous phase to the concentration of compound in immiscible solvent, as the neutral molecule. The log P value is obtained by predictive computational methods and provides a general guideline as to whether a drug gains rapid access to the CNS, or not. Thus, it has been established over the past more than 30 years that, assuming passive absorption, drugs with optimum CNS penetration generally have log P values around or somewhat above 2. Significantly lower log P values are often associated with low brain-to-plasma and high non-brain tissue-to-plasma ratios (see above: log P and T/P ratios for Galantamine). However, much higher log P values are also of disadvantage, as high lipophilicity is often associated with toxicity, non-specific binding, insufficient oral absorption and limited bioavailability. It follows from this account that BBB penetration and T/P ratios are essential parameters to be considered in the case of drugs that are supposed to act mainly or exclusively in the central nervous system.

Other important parameters controlling BBB penetration of a compound are the total polar surface area, the existence of ionizable groups on the molecule and the affinity of binding to biological membranes as compared to the affinity of binding to serum albumin. The latter data set is often used to scrutinize calculated log P values. In those cases in which special transport systems do not play a major role for the transport of a compound through the BBB, the predictions of lipophilicity and BBB penetration properties are quite suitable for the design of derivatives that transfer the BBB more efficiently than the parent compound.

The present disclosure relates to methods by which the lipophilicity and/or BBB penetration and/or brain-to-plasma ratio of a compound is enhanced by formation of a reversible linkage with one or more suitable groups so as to yield "pro-drugs", i.e., chemical derivatives that, after having passed through the blood-brain barrier, are converted (back) to the original compound itself inside the patients brain. Liberation of the parent compound may be by chemical hydrolysis or enzymatic attack, or by redox reactions. In another embodiment, the present invention refers to compounds that after chemical modification of the base compound have achieved a log P value more favourable for BBB penetration, with these derivatives acting as such at their target molecules in the patient's brain.

The plant alkaloid galantamine has been described as a cholinesterase inhibitor (ChE-I) and as a nicotinic acetylcholine receptor (nAChR) sensitizing agent (APL; allosterically potentiating ligand), and galantamine has been proposed for the treatment of several human brain diseases, including Alzheimer's disease (AD). Presently, the compliance of Alzheimer patients to treatment with ChE-I and APL is rather low, of the order of 20%, a key reason being the adverse effects nausea, diarrhea, vomiting, anorexia and muscle cramps. In the case of galantamine, the majority of these adverse effects is due to actions of the drug while passing through the gastro-intestinal tract, and to its rather limited permeation through the blood-brain barrier (BBB) into the brain. To help patients coping with the adverse effects of galantamine, the manufacturer's recommended daily dose of the drug is limited to 16-24 mg per day, and this dose is slowly reached by stepwise dose increase, beginning at 4 mg/day and over a period of 2-3 months.

The rather low levels of accumulation of galantamine in the brain, when administered as the unmodified drug, are a serious disadvantage with respect to the drug's therapeutic use, i.e., for the treatment of cognitive disorders, such as AD. As indicated by the brain-to-plasma ratio of ~1.3, only a small part of the administered drug reaches the brain, and the high levels of the drug in other (peripheral) tissues cause most, if not all, of the observed adverse effects. The mostly peripheral action of galantamine is also indicated in its previous use for the treatment of a number of neuromuscular disorders, including Myasthenia gravis and poliomyelitis.

In WO2007/039138 reference is made to the low hydrophobicity and related limited partition into the human brain of galantamine, and several procedures for overcoming these drawbacks of a medication that is supposed to act on target molecules located in the brain's central nervous system are proposed. In the same document numerous derivatives of galantamine that significantly improve transport of the respective compound through the blood-brain barrier (BBB) are described and they are proposed as drugs for the treatment of a variety of diseases associated with cognitive deficits.

Presently approved drugs for the treatment of Alzheimer's disease (AD) have in common that they all target excitatory neurotransmission in the brain, namely the cholinergic and the glutamatergic systems. Three of the four presently available drugs (Donepezil, Rivastigmin, Galantamine, Memantine) are cholinergic enhancers (Donepezil, Rivastigmin, Galantamine) in that they all inhibit the family of acetylcholine-degrading enzymes denoted as cholinesterases (ChE). Inhibition of ChE increases the synaptic concentrations of acetylcholine (ACh), thereby enhancing and prolonging the action of ACh on muscarinic (mAChR) and nicotinic (nAChR) acetylcholine receptors. In addition to acting as ChE inhibitor, Galantamine also acts by allosterically stimulating (sensitizing) cholinergic receptors. Allosteric sensitization of nicotinic receptors enhances their activation by ACh or choline (Ch), thereby correcting for a disease-associated deficit in transmitter or receptor concentration (Maelicke A & Albuquerque E X (1996) Drug Discovery Today 1, 53-59; Maelicke A & Albuquerque E X (2000) Eur J Pharmacol 393, 165-170). In addition to their therapeutic benefits, these drugs induce adverse peripheral and central side effects; the muscarinic ones including nausea, vomiting and diarrhea, and the nicotinic ones including tremors and muscle cramps. From meta data (Cochrane reviews, (2004), Issue 4) and direct comparison clinical studies (Wilcock G K et al. (2000) Brit Med Journ 321:1-7), the relatively weakest of the three presently used ChE inhibitors, Galantamine, has the highest clinical efficacy, with the therapeutic benefit achieved at concentrations that are well below those required for effective inhibition of AChE (Raskind M A et al. (2000) Neurology 54, 2261-2268; Maelicke A & Albuquerque E X (2000) Eur J Pharmacol 393, 165-170). It has been suggested that the higher therapeutic efficacy of Galantamine, as compared to the other two available ChE inhibitors, is due to an additional or alternative mode of action, i.e., allosteric sensitization of nAChR (Maelicke A & Albuquerque E X (1996) Drug Discovery Today 1, 53-59).

Galantamine enhances nicotinic cholinergic neurotransmission by acting directly on nicotinic receptors (Schrattenholz A et al. (1996) Mol Pharmacol 49, 1-6; Samochocki M et al. (2003) J Pharmacol Exp Therap 305, 1024-1036). The drug binds to a distinct allosteric site on these receptors (Schrider B et al. (1993) J Biol Chem 269, 10407-10416), from which it acts synergistically with acetylcholine (or choline) to facilitate nAChR activation (Maelicke A & Albuquerque E X (1996) Drug Discovery Today 1, 53-59; Maelicke A & Albuquerque E X (2000) Eur J Pharmacol 393, 165-170). Compounds acting like Galantamine in this way are referred to as "allostericaly potentiating ligands (APL)" (Schrattenholz A et al. (1996) Mol Pharmacol 49, 1-6, Maelicke A & Albuquerque E X (2000) Eur J Pharmacol 393, 165-170).

The APL action on human nicotinic receptors has been demonstrated by electrophysiological studies using human brain slices (Alkondon, M. et al., (2000) J Neurosci 20, 66-75) and human recombinant cell lines each expressing a single nAChR subtype (Samochocki M et al (2000) Acta Neuro Scand Suppl 176, 68-73, Samochocki M et al. (2003) J Pharmacol Exp Therap 305, 1024-1036). All human nAChR subtypes analysed so far are sensitive to enhancement by APL. In the presence of Galantamine, the binding affinity and channel opening probability of nAChR are increased, leading to a decrease in EC50 for ACh between 30% and 65% (Samochocki M et al (2000) Acta Neuro Scand Suppl 176, 68-73, Samochocki M et al. (2003) J Pharmacol Exp Therap 305, 1024-1036). Furthermore, Galantamine increases the slope of the dose-response curve for ACh, which has been interpreted as an increase in the cooperativity between nAChR subunits (Maelicke A & Albuquerque E X (1996) Drug Discovery Today 1, 53-59).

The APL effect of Galantamine is observed at submicromolar concentrations (Samochocki M et al (2000) Acta Neuro Scand Suppl 176, 68-73, Samochocki M et al. (2003) J Pharmacol Exp Therap 305, 1024-1036), i.e., below the concentration range at which ChE inhibition takes place. The two modes of action of nicotinic APL are independent of each other, as was shown by ion flux studies (Okonjo K et al (1991) Eur J Biochem 200, 671-677; Kuhlmann J et al (1991) FEBS Lett 279, 216-218) and electrophysiological studies of brain slices from both rats and humans (Santos M D et al (2002) Mol Pharmacol 61, 1222-1234). In these studies, when cholinesterase activity was completely blocked by either reversible or irreversible blocking agents, the nicotinic APL, e.g., Galantamine, still was able to produce an APL effect of the same size as in the absence of the other ChE inhibitors. Of the cholinesterase inhibitors presently approved as AD drugs, Galantamine is the only one with nicotinic APL activity (Maelicke A et al (2000) Behav Brain Res 113, 199-206).

The use of Galantamine and other APL as a drug treatment strategy for cognitive disorders, including AD and PD was proposed in 1996 (Maelicke A & Albuquerque E X (1996) Drug Discovery Today 1, 53-59). Later, the proposal was extended to vascular and mixed dementia (Maelicke A et al (2001) Biol Psychiatry 49, 279-288), schizophrenia, epilepsy and other diseases with a nicotinic cholinergic deficit.

The comparatively low levels of accumulation of Galantamine in the brain are a serious disadvantage with respect to the drug's therapeutic use, i.e., for the treatment of cognitive disorders, such as AD. As indicated by the T/P ratios, only a small part of the administered drug reaches the brain, and the high levels of the drug in other (peripheral) tissues may be responsible for some of the observed adverse side effects. As a point in case, long before having been approved for the treatment of AD, Galantamine has primarily been used for the treatment of a number of neuromuscular disorders, including Myasthenia gravis and poliomyelitis.

EP-A 648 771, EP-A 649 846 and EP-A 653 427 all describe Galantamine derivatives, a process for their preparation and their use as medicaments, however none of these applications considers ways and means of enhancing penetration through the blood-brain barrier and brain-to-plasma ratio of base compounds and derivatives.

U.S. Pat. No. 6,150,354 refers to several Galantamine analogues for the treatment of Alzheimer's disease. However, selective chemical modification for the purpose of increasing penetration through the blood-brain barrier is not considered.

WO 01/74820, WO 00/32199 and WO 2005030333 refer to derivatives and analogues of Galantamine for the treatment of a variety of human brain and other diseases, and acute functional brain damage. However, selective chemical modifications or other means of improving blood-brain barrier penetration are not considered.

WO 88/08708, WO 99/21561, WO 01/43697 and US 2003/0162770 refer to derivatives and analogues of Galantamine for the treatment of various cognitive symptoms. However, selective chemical modifications or other means of improving blood-brain barrier penetration are not considered.

WO 2005/030713 refers to a method for the synthesis of optical isomers of Galantamine from a Narwedine bromoamide derivative. However, it does not deal with other derivatives of Galantamine, or their use as medicaments, or chemical modifications aimed at enhancing blood-barrier penetration of said compounds.

WO 97/40049 describes several derivatives of benzazepines and related compounds that may be applied for the treatment of Alzheimer's disease. However, no concept is provided in this application for increasing the penetration of compounds through the blood-brain barrier.

SUMMARY OF THE INVENTION

Some embodiments provide compounds usable as pro-drugs or as a medicament having high pharmacodynamic effects in the brain's central nervous system and low peripheral side effects.

Compounds disclosed herein include those described by formula (III):

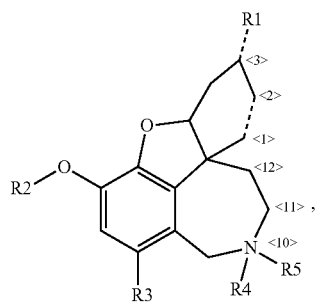

(III)

wherein the bond <1> to >2> is a single or a double bond and the bond between <3> and R1 is a single or a double bond and bond <10> to <11> is a single or no bond and residues are R1: OH, OCO-(3-pyridyl)(=nicotinic acid residue), OCO-(3-methyl-3-pyridyl), OCO—($C_1$-$C_6$ alkyl), OCO—($C_1$-$C_{21}$ alkenyl), OCO—NH—($C_1$-$C_6$ alkyl), OCO—($CH_2$)$_x$—NH—COO—($C_1$-$C_6$ alkyl), O—$CH_2$—O—($C_1$-$C_6$ alkyl), O—($CH_2$)$_x$—OCO—($C_1$-$C_6$ alkyl), O—($CH_2$)$_x$—OCO—($CH_2$)$_x$—N—COO—($C_1$-$C_6$ alkyl), O—($CH_2$)$_x$—OCO—($CH_2$)$_y$-aryl, OCOO—($C_1$-$C_6$ aminalkyl), OCOO—($CH_2$)$_x$-tetrahydrofuranyl, or a sugar, preferably glucuronic acid residue, wherein x=1, 2, 3 or 4 and y=0, 1, 2, 3 or 4;

wherein if bond <3> to R1 is a double bond, then R1=O, NH, NOH, NOR6, N—CO—$NH_2$, N—CS—$NH_2$, N—C(=NH)—$NH_2$, N—NH-phenyl, N—NHR6, N—N(R6)$_2$, N—N=($CH_2$)$_n$, with R6=$C_1$-$C_5$ unbranched or branched, saturated or unsaturated (ar)alkyl, phenyl or benzyl and n=2-8; and wherein if bond <3> to R1 is a single bond, then R1=OH, SH, $NH_2$, NHR6, N(R6)$_2$, OR7, O—CR8R9, O—CO—CHR10, NR11R12, or O—CO—R14, with R7=$C_1$-$C_{22}$ unbranched or branched, (poly-)unsaturated or saturated alkyl, optionally containing an additional (ar)alkoxy or di(ar)alkylamino group, a sugar or sugar derivative residue, preferably glucuronic acid residue, a phosphoryl, alkylphosphoryl or arylphosphoryl group, a sulfatyl or alkylsufatyl group, or COR13, where R13=R6 or R7 or pyridyl or dihydropyridyl or OR6, preferably methyl, 3-pyridyl, 4-pyridyl, 3-dihydropyridyl, 4-dihydropyridyl R8 and R9 are the same or different and any of H, Me, Ph or they together form a spiro-ring —($CH_2$)n- with n=4-6

R10=H or the side chain of a natural amino acid including R10, R11 together are forming a proline or hydroxy-proline derivative R11 either is together with R10 forming a proline or hydroxy-proline derivative or is H R12 is a carbamate protecting group including t-butoxycarbonyl, benzyloxycarbonyl and other N-protecting groups;

R14 is an aromatic or heteroaromatic 5- or 6-membered ring, selected from substituted benzene with the proviso that it is not 2-fluorobenzene or 3-nitro-4-fluorobenzene, optionally substituted naphthaline, thiophene, pyrrole, imidazole, pyrazole, oxazole, thiazole; or CH($C_2H_5$)$CH_3$, $CH_2$—C($CH_3$)$_3$, or cyclopropane;

R2: R7, or O—CR8R9, O—CO—CHR10, or NR11R12 with the same definitions of R7-R12 as above, H, $CH_3$, CO—($C_1$-$C_6$ alkyl), $CH_2$—OCO—($CH_2$)$_x$-aryl, or a sugar, preferably glucuronic acid residue;

R3: H, F, Cl, Br, I, $NH_2$, $NO_2$, CN, $CH_3$;

R4: H, $C_1$-$C_6$ alkyl, preferably $CH_3$, CO—($C_1$-$C_6$ alkyl), CO-(3-pyridyl)(=nicotinic acid residue), CO-(3-methyl-3-pyridyl), CO—(CH-mercaptoalkyl)-($CH_2$)$_x$-aryl, ($CH_2$)$_x$—OCO—($CH_2$)$_x$—N—COO—($C_1$-$C_6$ alkyl), ($CH_2$)$_x$—OCO—(CH-arylalkyl)-N—COO—($C_1$-$C_6$ alkyl), wherein x=1, 2, 3 or 4;

R5: if R4=H, then R5 is an electron pair;

if R4=$CH_3$ then R5 is an electron pair, hydrogen or a $C_1$-$C_5$ (ar)alkyl group, $CH_2$—O—$CH_3$, $CH_2$—O—CO—R6, $CH_2$—O—CR8R9, O—CO—CHR10, or NR11R12 with the same definitions of R6 and R8-R12 as above, and wherein the nitrogen at position <10> has an additional positive charge as well as a counterion, selected from chloride, bromide, iodide, sulphate, nitrate, hydrogensulfate, phosphate, methanesulphonate, tosylate or any other pharmaceutically acceptable anion, with the proviso that the resulting compound is not Galantamine, Norgalantamine, Sanguinine, Norsanguinine, Lycoramine, Norlycoramine, Lycoraminone, Narwedine, Nornarwedine,3-Amino-3-deoxy-galantamine or 3-amino-3-deoxy-1,2-dihydro-galantamine;

or R5=$(CH_2)_x$—O—$(C_1$-$C_6$ alkyl), $(CH_2)_x$—OCO—$(C_1$-$C_6$ alkyl), $(CH_2)_x$—OCO—$(CH_2)$-aryl, $(CH_2)_x$—OCO—$(CH_2)$—N—COO—$(C_1$-$C_6$ alkyl), wherein x=1, 2, 3 or 4; wherein when bond <10> to <11> is a single bond the nitrogen at position <10> has a positive charge and the counterion is chloride, with the proviso that the compound is not Galantamine, Norgalantamine, Sanguinine, Norsanguinine, Lycoramine, Norlycoramine, Lycoraminone, Narwedine, Nornarwedine,3-Amino-3-deoxy-galantamine or 3-amino-3-deoxy-1,2-dihydro-galantamine as a pro-drug or medicament with improved blood-brain barrier permeability compared to Galantamine.

Other embodiments relate to procedures for achieving a favorable distribution ratio of brain to periphery for antidementia drugs of various kinds, including cholinergic receptor sensitizing agents, cholinesterase inhibitors and neuroprotective drugs.

In this way the therapeutic effect-to-dose ratio can be increased and adverse side-effects can be reduced when the drugs are administered as medicaments for the diseases mentioned in the present application. This object is particularly met e.g., by site-specific chemical modification (derivatization) of said compounds.

BRIEF DESCRIPTION OF THE DRAWINGS

FIG. 8. Extraction Procedure. (A) Preparation of STD, QC and Study Samples. (B) Preparation of Calibration Curve Standards for Recovery.

DETAILED DESCRIPTION OF THE PREFERRED EMBODIMENT

Figure 1:
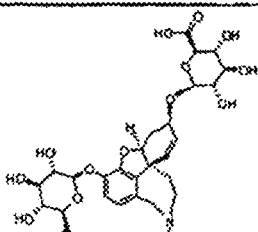
FIG. 1: 125 chemical structures and log P values of new compounds that (i) act as cholinergic enhancers, and/or (ii) have higher log P-values than Galantamine (Galantamine included in Table 4 for comparison).
Figure 1:
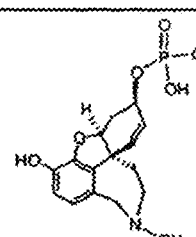
Figure 1:
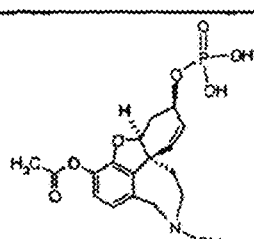
Figure 1:
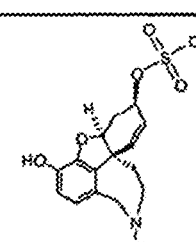
Figure 1:
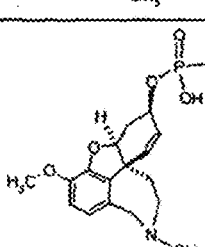
Figure 1:
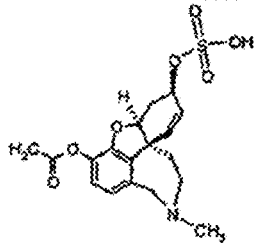
Figure 1:
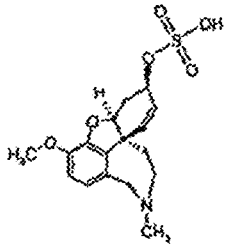
Figure 1:
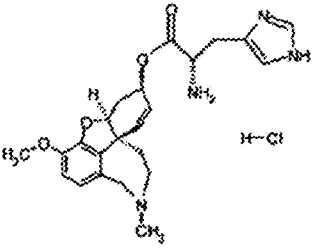
Figure 1:
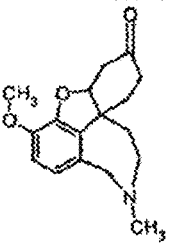
Figure 1:
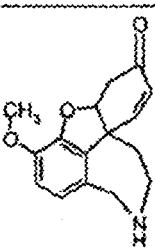
Figure 1:
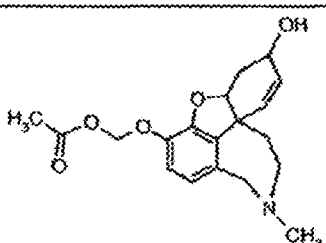
Figure 1:
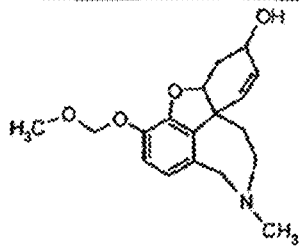
Figure 1:
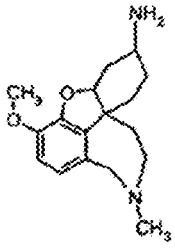
Figure 1:
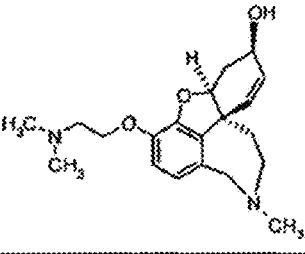
Figure 1:
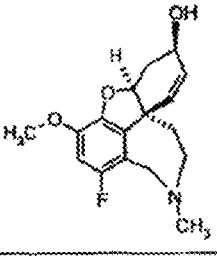
Figure 1:
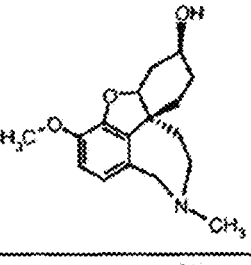
Figure 1:
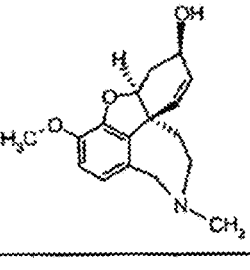
Figure 1:
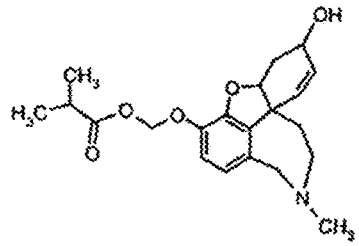
Figure 1:
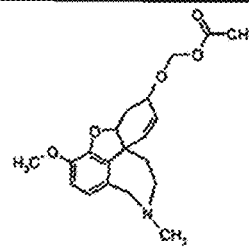
Figure 1:
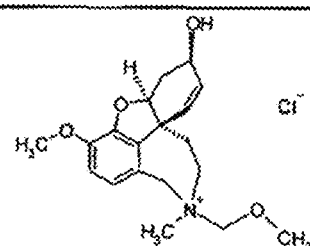
Figure 1:
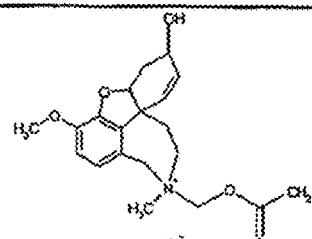
Figure 1:
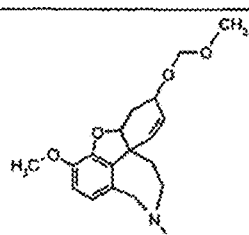
Figure 1:
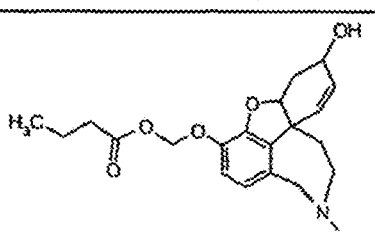
Figure 1:
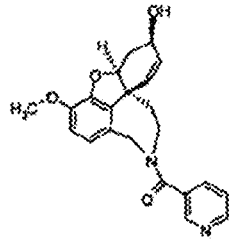
Figure 1:
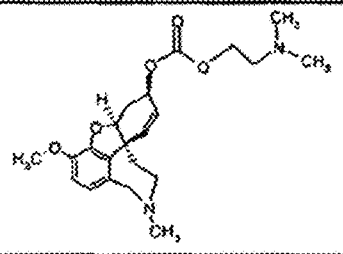
Figure 1:
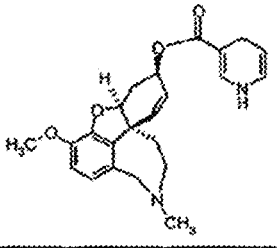
Figure 1:
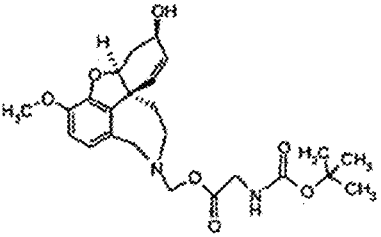
Figure 1:
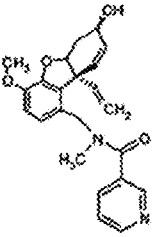
Figure 1:
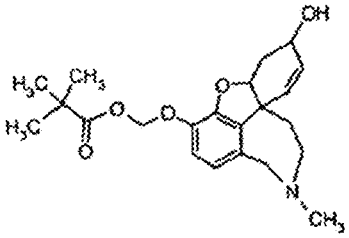
Figure 1:
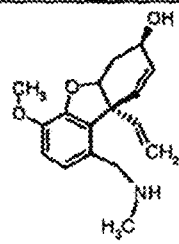
Figure 1:
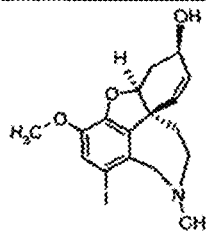
Figure 1:
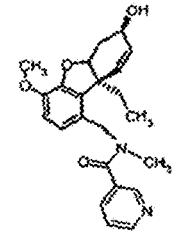
Figure 1:
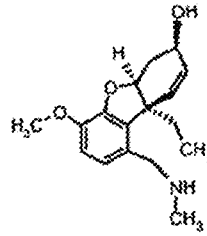
Figure 1:
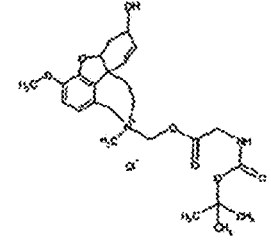
Figure 1:
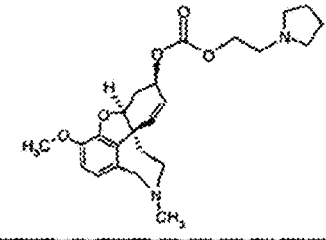
Figure 1:
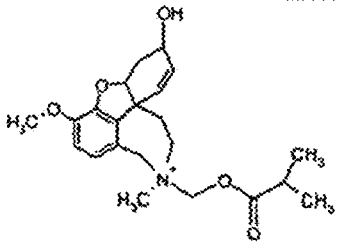
Figure 1:
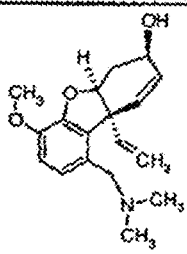
Figure 1:
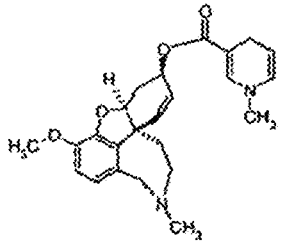
Figure 1:
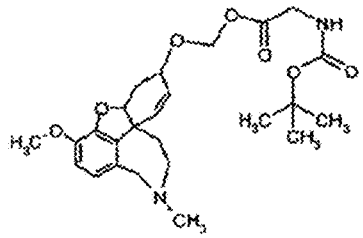
Figure 1:
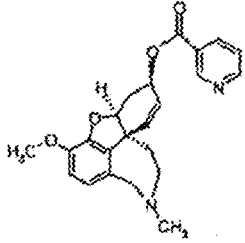
Figure 1:
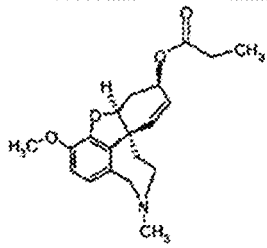
Figure 1:
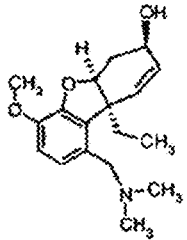
Figure 1:
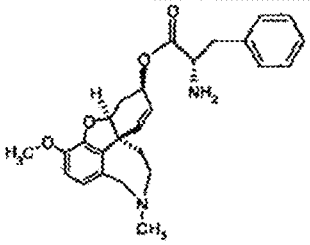
Figure 1:
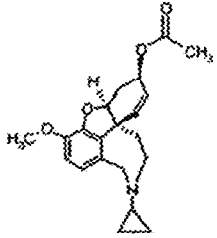
Figure 1:
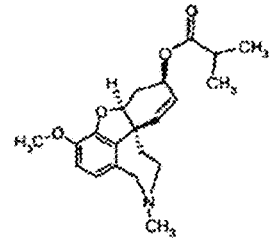
Figure 1:
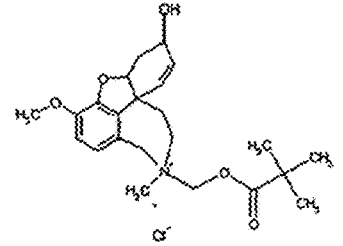
Figure 1:
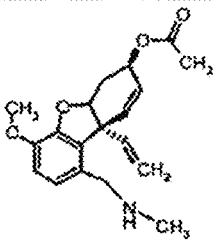
Figure 1:
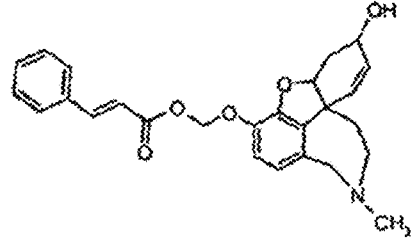
Figure 1:
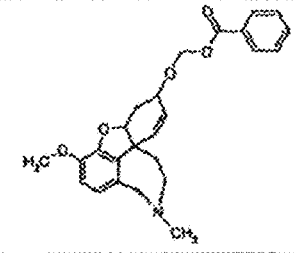
Figure 1:
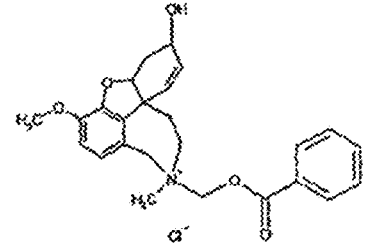
Figure 1:
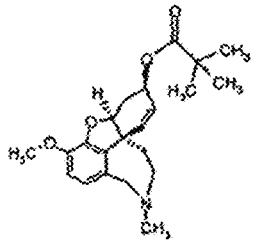
Figure 1:
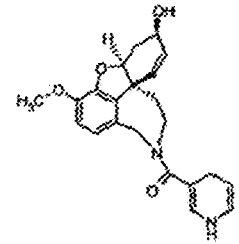
Figure 1:
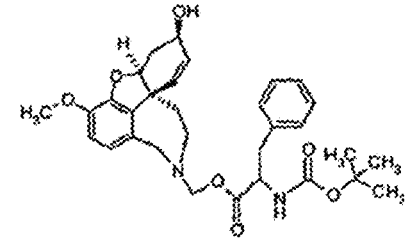
Figure 1:
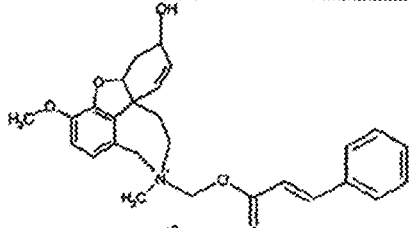
Figure 1:
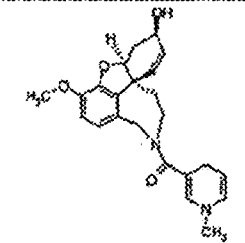
Figure 1:
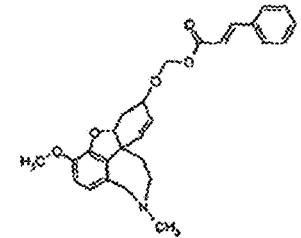
Figure 1:
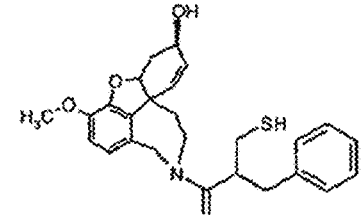
Figure 1:
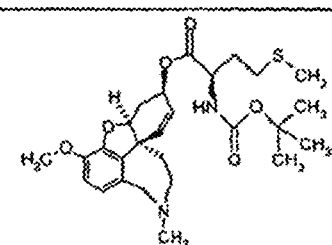
Figure 1:
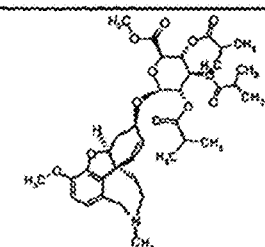
Figure 1:
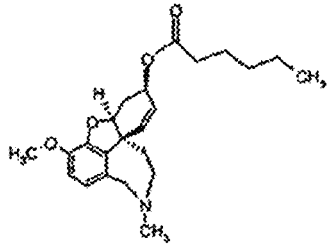
Figure 1:
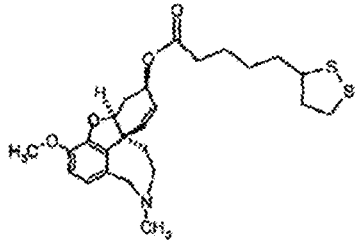
Figure 1:
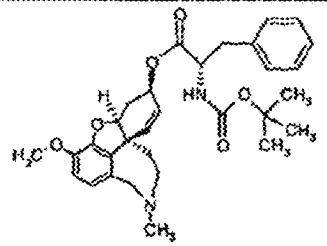
Figure 1:
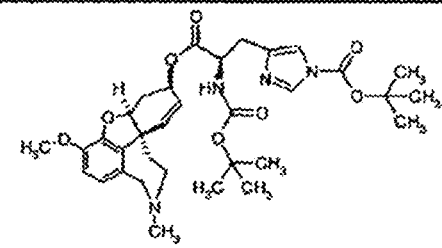
Figure 1:
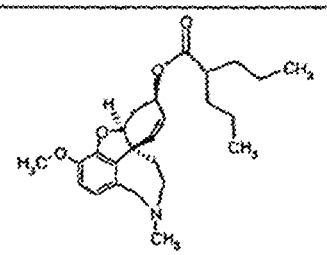
Figure 1:
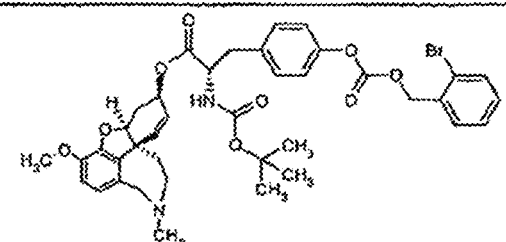
Figure 1:
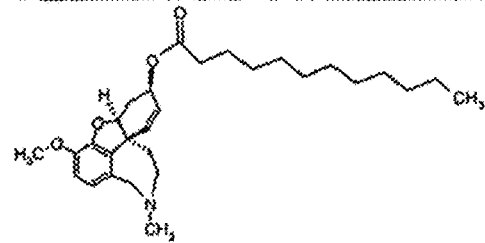
Figure 1:
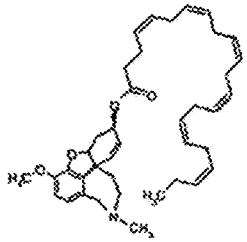
Figure 1:
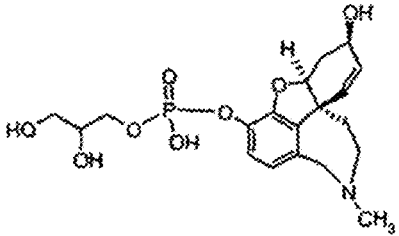
Figure 1:
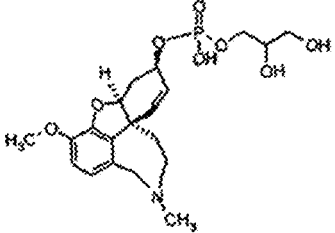
Figure 1:
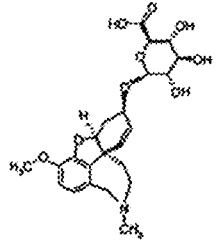
Figure 1:
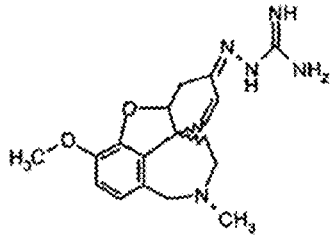
Figure 1:
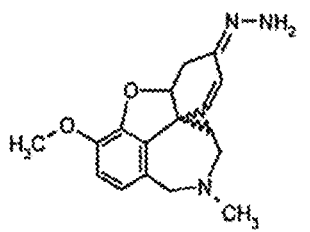
Figure 1:
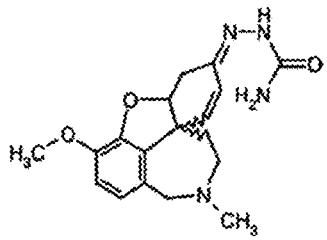
Figure 1:
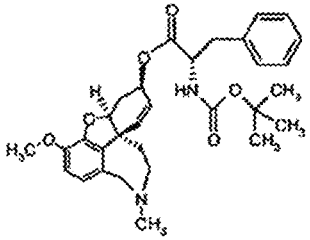
Figure 1:
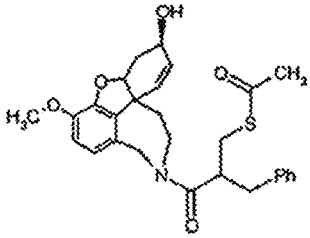
Figure 1:
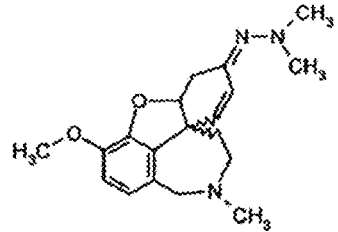
Figure 1:
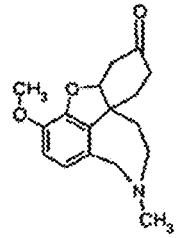
Figure 1:
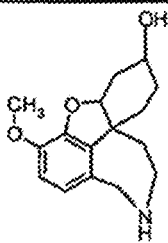
Figure 1:
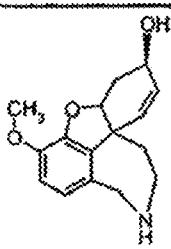
Figure 1:
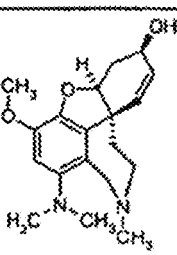
Figure 1:
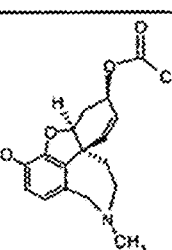
Figure 1:
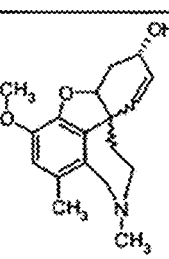
Figure 1:
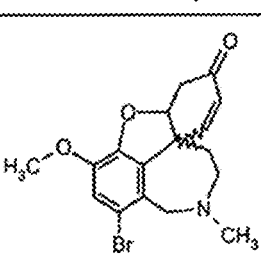
Figure 1:
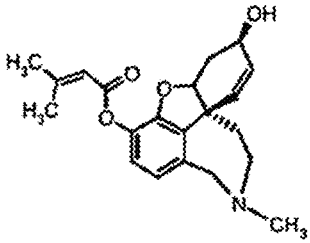
Figure 1:
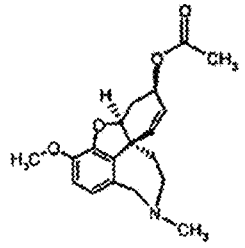
Figure 1:
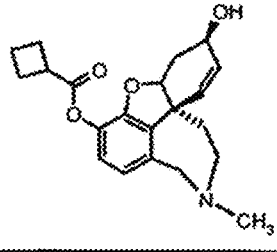
Figure 1:
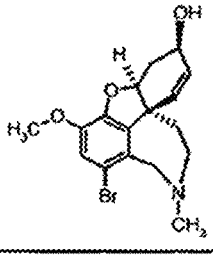
Figure 1:
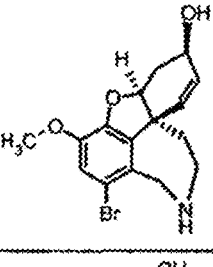
Figure 1:
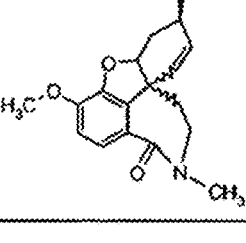
Figure 1:
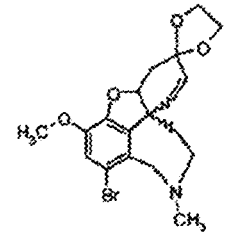
Figure 1:
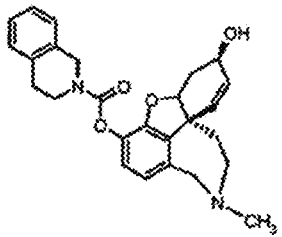
Figure 1:
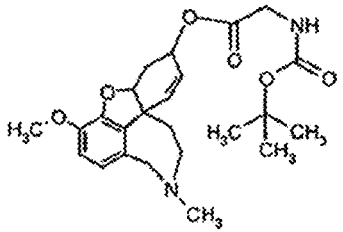
Figure 1:
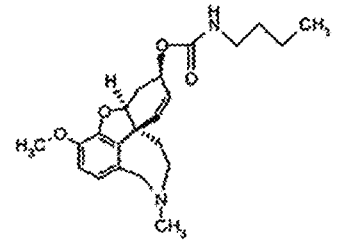
Figure 1:
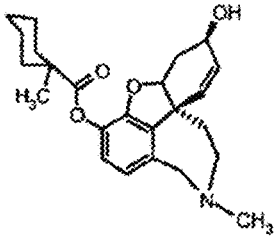
Figure 1:
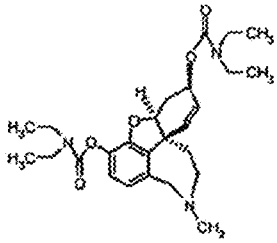
Figure 1:
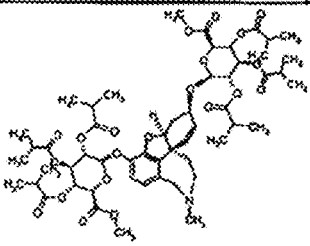
Figure 1:
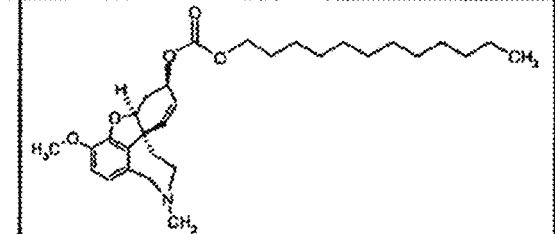
Figure 1:
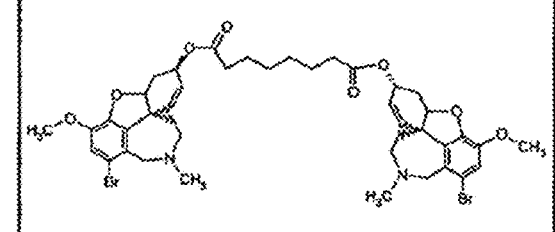
Figure 1:
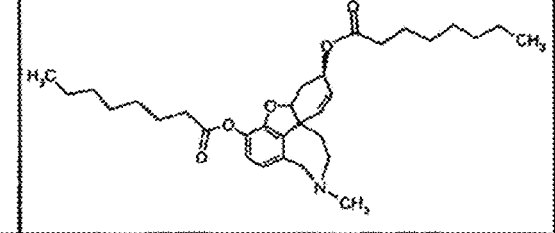
Figure 1:
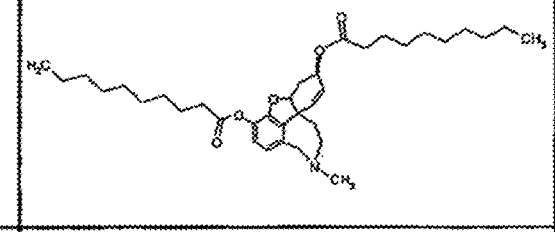
Figure 1:
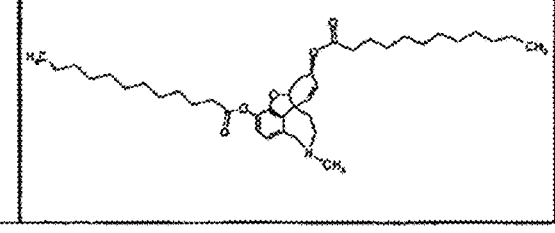

The present disclosure relates to significant enhancement in the brain-to-plasma ratio of cholinergic receptor sensitizing agents, such as the APL Galantamine (and related compounds), which is achieved by administering not the drug itself but a "pro-drug" that is converted (back) to the drug itself inside the brain of the patient. As another means for improving penetration through the blood-brain barrier (BBB) and thereby the therapeutic efficacy of the drug, the compounds themselves have been chemically modified so as to not only having larger efficacy as nicotinic APL and/or as neuroprotective agent, but in addition having enhanced lipophilicity (higher log P) or otherwise improved BBB transport properties. Due to these improvements, the pro-drugs and other compounds addressed in this application should be significantly more potent as medicaments for the treatment of cognitive disorders than is, for example, Galantamine. The invention applies to the compounds, selected pro-drugs and pharmaceutically acceptable salts thereof, which might be administered via the mouth, blood, skin, by nasal application, or any other suitable application route.

Herein the term "pro-drug" refers to a derivative of a base compound wherein the group(s) added or replaced on said base compound are cleaved or returned to the group originally contained in the base compound when the derivative has reached the area or site of action. Thus, in case of a "pro-drug", an effective agent is administered as a derivative (which is said pro-drug), however, the compound mainly or exclusively effective at the target site within the brain is the agent itself, not the derivatized compound or metabolites thereof.

The term "derivative" refers to any change of a base compound defined in the present application. The term "derivative" is used to describe a compound which either can be a pro-drug, or can be an effective agent itself/in its own right or in the derivatized form.

The terms "sensitizing agent" and "allosterically potentiating ligand, APL" refer to effectors that enhance cholinergic neurotransmission by direct interaction via an allosteric site with cholinergic receptors.

The terms "cholinergic enhancer" and "cholinergic agent" refer to compounds that enhance/modulate cholinergic neurotransmission by inhibition of cholinesterases, by allosteric sensitization and/or direct activation of cholinergic receptors and/or by activating/modulating relevant intracellular pathways via second messenger cascades.

A derivative or pro-drug has an "enhanced blood-brain barrier permeability "according to the present invention or an "enhanced blood-brain barrier penetration" if, after administration of a pro-drug or derivative thereof to a living organism, a higher amount of said compound penetrates through the BBB, resulting in a higher level of effective agent in the brain, as compared to administration of the base compound without derivatization. The enhanced BBB penetration should result in an increased brain-to-tissue ratio of the effective agent compared to the ratio of the base compound. Methods for determination of an enhanced BBB permeability are disclosed in this application (see supra).

The "base compound" according to the present invention preferably is Galantamine, Norgalantamine, Narwedine, N-Demethylnarwedine, Lycoramine, Lycoraminone, Sanguinine, Norsanguinine, and others (see table 1).

"log P" is defined as the decadic logarithm of the partition coefficient P which is the ratio of the concentration of a compound in aqueous phase to the concentration of a compound in immiscible solvent, as the neutral molecule.

The term "alkyl" shall mean a straight, branched or cyclic alkyl group of the stated number of carbon atoms. Examples include, but are not limited to methyl, ethyl, n-propyl, iso-propyl, n-butyl, isobutyl, sec-butyl, t-butyl, and straight and branched chain pentyl, hexyl, heptyl, octyl, nonyl, decyl, undecyl, dodecyl, pentadecyl etc. . . . or the according cyclic alkyls.

The term "halo" shall mean chloro, fluoro, bromo and iodo.

The term "aryl" shall mean phenyl having 0, 1, 2 or 3 substituents independently selected from the group of alkyl, alkoxy, alkylcarbonyl, halo- or trihalomethyl.

The term "cycloalkyl" shall mean a cycloalkyl group of from 3 to 12 carbon atoms and including multiple ring alkyls such as for example, adamantyl, camphoryl, and 3-noradamantyl.

In any case when a range between two limits is described it is meant that any value or integer in this range is disclosed. For example "$C_1$-$C_8$" means $C_1$, $C_2$, $C_3$, $C_4$, $C_5$, $C_6$, $C_7$ or $C_8$; or "between 0,1 and 1" means 0,1, 0,2, 0,3, 0,4, 0,5, 0,6, 0,7, 0,8, 0,9 or 1.

A "natural amino acid" is any amino acid naturally occurring in biochemical pathways or in peptides/proteins. These are particularly alanine, asparagine, cysteine, glutamine, phenylalanine, glycine, histidine, isoleucine, methionine, proline, glutamate, arginine, serine, threonine, valine, thryptophane, tyrosine, their methylated forms or the according salts.

With "sugar" is meant any suitable sugar, either an aldose or ketose, a pyranose or furanose, heptose or hexose, mono- or polysaccharide, like e.g., glucuronic acid, glucose, fructose, galactose, mannose, saccharose, lactose, maltose etc., however, glucuronic acid is preferred.

The main focus of the present invention is to improve blood-brain barrier permeability, by increasing the lipophilicity or the transport properties, or the ability of passing the blood-brain barrier, of compounds that are known to act as effective agents in correcting a cholinergic deficit, e.g., APL of nicotinic receptors or inhibitors of cholinesterases.

In one preferred embodiment the present invention refers to a method for increasing blood-brain barrier penetration of a cholinergic enhancer by preparing derivatives (either formally by their chemical structure or directly by chemical synthesis) of a molecule with a base structure of the general formula (I):

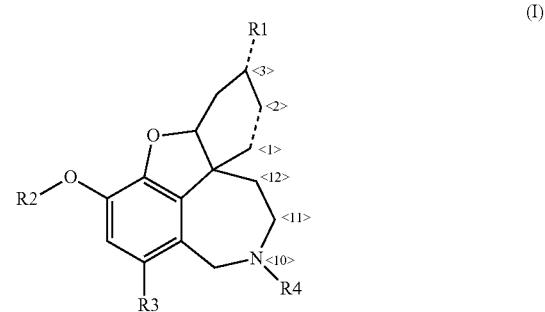

wherein the bond between positions <1> and <2> as well as <11> and <12> denotes a single- or double bond, and the bond between <10> and <11> is either a single bond or no bond.

R1=O, =NOH, =NH—NHCH₃, —OH, —OCOCH₃, —NH₂, or a (substituted) derivative of the ketone, like semicarbazone, thiosemicarbazone, aminoguanidine etc.

R2=H, CH₃, acetyl

R3=H, CH₃, F, Cl, Br, I

R4=H, CH₃.

In Table 1, compounds are exemplified with a base structure of the general formula (II)

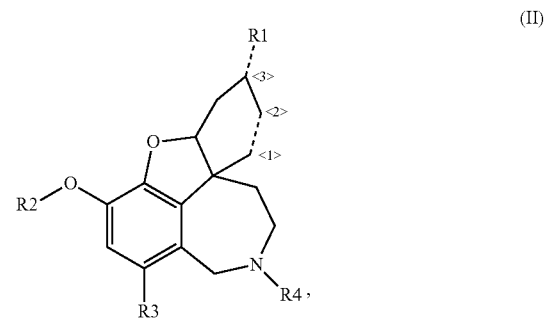

that belong to the structures summarized in formula (I):

TABLE 1

| R1 | R2 | R3 | R4 | Bond <1>—<2> | Bond <3>—R1 | Name | logP calcd.(1) |
|---|---|---|---|---|---|---|---|
| OH | CH₃ | H | CH₃ | Double | Single | Galantamine | 1.30 |
| OH | CH₃ | H | H | Double | Single | Norgalantamine | 1.38 |
| OH | H | H | CH₃ | Double | Single | Sanguinine | 0.83 |

TABLE 1-continued

| R1 | R2 | R3 | R4 | Bond <1>—<2> | Bond <3>—R1 | Name | logP calcd.(1) |
|---|---|---|---|---|---|---|---|
| OH | H | H | H | Double | Single | Norsanguinine | 0.91 |
| MeCH(OH) | H | H | CH₃ | Double | Single | Leucotamine | 1.23 |
| CH₂—CO | | | | | | | |
| OH | CH₃ | H | CH₃ | Single | Single | Lycoramine | 1.28 |
| OH | CH₃ | H | H | Single | Single | Norlycoramine | 1.36 |
| O | CH₃ | H | CH₃ | Single | Double | Lycoraminone | 0.85 |
| O | CH₃ | H | CH₃ | Double | Double | Narwedine | 0.74 |
| O | CH₃ | H | H | Double | Double | Nornarwedine | 0.82 |
| NH2 | CH₃ | H | CH₃ | Double | Single | 3-Amino-3-deoxy-galantamine | 1.05 |
| NH2 | CH₃ | H | CH₃ | Single | Single | 3-amino-3-deoxy-1,2-dihydro-galantamine | 0.89 |

(1)Calculated using Advanced Pharma Algorithms Software ToxBoxes V1.0.2

The compounds listed in Table 1, and other compounds to be used as a base compound for derivatization according to the present invention, can be obtained either by isolation from natural sources or by total chemical synthesis, or by chemical modification of natural or synthetic compounds.

The compounds to be used according to the present invention can be derivatives of the above listed molecules that can be demonstrated to act as cholinergic enhancers. This property of said derivatives may be manifested by one or more of the following properties; by their ability to sensitize cholinergic receptors, and/or inhibit brain cholinesterases, and/or modulate intracellular messenger levels, and/or act neuroprotective. The ability to act as sensitizing agent on nicotinic receptors can be determined by electrophysiological and Ca-imaging methods, as described in Schrattenholz A et al. (1996) Mol Pharmacol 49, 1-6 and Samochocki M et al (2000) Acta Neuro Scand Suppl 176, 68-73; Samochocki M et al. (2003) J Pharmacol Exp Therap 305, 1024-1036. The ability to inhibit cholinesterases can be determined by the photometric method of Ellman et al., Biochem. Pharmacol. 7, 88 (1961). The ability to modulate intracellular messenger levels can be determined by Ca-imaging methods (Samochocki M et al. (2003) J Pharmacol Exp Therap 305, 1024-1036) and other means of recording changes in intracellular messenger levels or effects resulting thereof (Kihara T et al (2004) Biochem Biophys Res Commun 325, 976-982). The ability to act neuroprotective can be determined by a variety of in vitro and in vivo test systems, including in cell culture (Arias E et al (2003) Neuropharmacol 46, 103-1S 14; Kihara T et al (2004) Biochem Biophys Res Commun 325, 976-982) and in animal models of neurodegenerative diseases (Capsoni et al (2002) Proc Natl Acad Sci USA 99, 12432-12437).

As specific examples, Table 2 exemplifies compounds that are derivatives of a base structure of the following general formula (III)

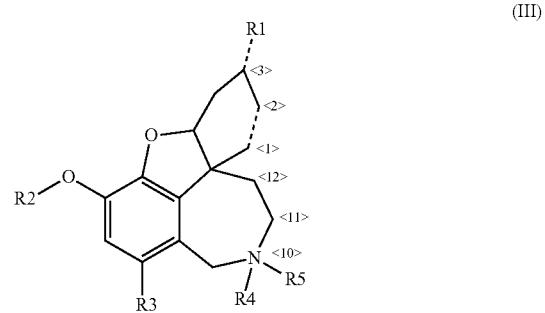

(III)

and act in any way as cholinergic enhancers:

TABLE 2

| R1 | R2 | R3 | R4 | R5 | Bond 1-2 | Bond 3-R1 | Bond 10-11 | Bond 11-12 | Name | logP calcd(1) |
|---|---|---|---|---|---|---|---|---|---|---|
| OH | CH₃ | H | CH₃ | CH₃ | D | S | n | S | 10,11-Seco-10-methyl-galantamine | 2.67 |
| OH | CH₃ | H | CH₃ | H | D | S | n | D | 10,11-Seco-11,12-dehydro-galantamine | 2.09 |
| NOH | CH₃ | H | CH₃ | e | D | D | S | S | Narwedinoxim | 1.15 |
| NNHCH₃ | CH₃ | H | CH₃ | e | D | D | S | S | Narwedin-N-methyl-hydrazone | 0.34 |
| OH | CH₃ | F | CH₃ | e | D | S | S | S | 8-Fluoro-galantamine | 1.25 |
| OH | CH₃ | Br | CH₃ | e | D | S | S | S | 8-Bromo-galantamine | 2.27 |
| OH | CH₃ | I | CH₃ | e | D | S | S | S | 8-Iodo-galantamine | 2.26 |
| OH | CH₃ | Br | CH₃ | O | D | S | S | S | 8-Bromo-galantamine-N-oxide | 2.68 |
| OH | H | H | CH3 | E | D | S | S | S | Sanguinine | 0.83 |
| O | CH₃ | H | CH₃ | e | D | D | S | S | Narwedin | 0.74 |
| O | CH₃ | CH₃ | CH₃ | e | D | D | S | S | 8-Methyl-narwedine | 1.15 |
| O—CO—(CH₂)11—CH₃ | CH₃ | H | CH₃ | e | D | S | S | S | GLN-0962 | 7.42 |

TABLE 2-continued

| R1 | R2 | R3 | R4 | R5 | Bond 1-2 | Bond 3-R1 | Bond 10-11 | Bond 11-12 | Name | logP calcd(1) |
|---|---|---|---|---|---|---|---|---|---|---|
| O—CO—(CH2)6—CO—gal-6-yl | CH₃ | H | CH₃ | e | D | S | S | S | GLN-0971 | 7.80 |
| O—CO—(CH₂)₁₁—CH₃ | CO—(CH₂)₁₁—CH₃ | H | CH₃ | e | D | S | S | S | GLN-0935 | 11.7 |

(1)Calculated using Advanced Pharma Algorithms Software ToxBoxes V1.0.2.
Abbreviations: s: single bond; d: double bond; n: no bond; e: electron pair Most of the compounds listed in Table 2 are not only efficacious agents in one or more of the tests cited above, but most of them also have more favourable log P and/or transport properties than the base compounds from which they are derived.

To further improve BBB permeability and brain/plasma distribution ratio, modifications of the following kinds can be performed so as to make the compounds exemplified in Tables 1 and 2 more lipophilic or enhance otherwise their transport into the CNS, in comparison to the base compound:

1. Conjugations to groups or molecules that are known to occur in the course of metabolic conversions, e.g., carbohydrate conjugates such as glycosyls, glucuronides and natural metabolites, or are otherwise known to readily pass the blood-brain barrier, e.g., amino acids, vitamins, various messenger molecules and drugs.
2. Conjugations to groups leading to quaternary ammonium salts with a labile nitrogen-carbon bond (see e.g., Example 1).
3. Conjugations to groups leading to esters, e.g., acylderivates with enhanced lipophilicity and BBB penetration properties. For example, such compounds may be esters of the oxygen function in position 3 and/or 6 of the following base structure (IV):

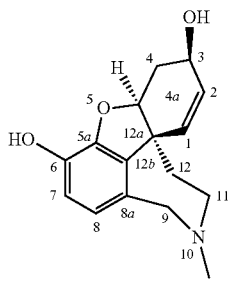

(IV)

a) Esters with saturated or unsaturated fatty acids containing 1-22 carbon atoms optionally containing an additional (ar)alkoxy or di(ar)alkylamino group
b) Esters with carbonic acid where one acidic function of carbonic acid is esterified with the 3- and/or 6-position of galantamine and the other represents an ester as defined in 3a.
c) Esters with (substituted) pyridine- or (substituted) dihydropyridine-carboxylic acids (see e.g., Example 2)
d) Esters with phosphoric and sulfonic acids 4. Formation of ketals or aminals of substituents in positions 3, 6, and 10 that increase the lipophilicity and are hydrolyzed to the desired derivatives, e.g., (nor) galantamine derivatives (see e.g., Examples 3 and 4)
5. Formation of basic and/or quaternary carbamates of said compounds that are chemically or metabolically unstable.
6. Conjugation to a lipophilic dihydropyridinium carrier, e.g., as 1,4-dihydro-1-methyl-3-pyridinecarboxylate, that in the brain is enzymatically oxidised to the corresponding ionic pyrimidinium salt.
7. Conjugation with nicotinic acid, nicotinic acid amide, various cofactors, messenger molecules and other chemical entities that enhance lipophilicity and transport through the BBB.

These modifications lead to compounds of the following general formula (III)

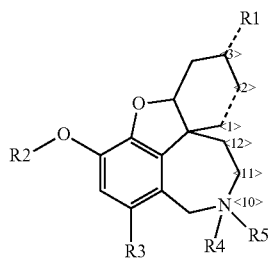

(III)

wherein the bond between positions <1> and <2> denotes a single- or double bond, with the proviso that the structure is not any of those listed in Table 1 and the bonds <1> to <2> and <11> to <12> can be either a single or a double bond, and the bond between <10> and <11> is either a single bond or no bond and the residues R1-R5 are defined as follows:

R1:
a) if bond <3> to R1 is a double bond, then
R1=O, NH, NOH, NOR6, N—CO—NH₂, N—CS—NH₂, N—C(=NH)—NH₂, N—NH-phenyl, N—NHR₆, N—N(R6)₂, N—N=(CH₂)ₙ
with R6=$C_1$-$C_5$ unbranched or branched, saturated or unsaturated (ar)alkyl, phenyl or benzyl and n=2-8
b) if bond <3> to R1 is a single bond, then
R1=OH, SH, NH₂, NHR6, N(R6)₂, OR7, O—CR8R9, O—CO—CHR10, or NR11R12
with R7=$C_1$-$C_{22}$ unbranched or branched, (poly-)unsaturated or saturated alkyl, optionally containing an additional (ar)alkoxy or di(ar)alkylamino group, a sugar or sugar derivative residue, preferably glucuronic acid, a phosphoryl, alkylphosphoryl or arylphosphoryl group, a sulfatyl or alkylsufatyl group
or COR13,
where R13=R6 or R7 or pyridyl or dihydropyridyl or OR6, preferably methyl, 3-pyridyl, 4-pyridyl, 3-dihydropyridyl, 4-dihydropyridyl
R8 and R9 are the same or different and any of H, Me, Ph or they together form spiro-ring —(CH$_2$)$_n$— with n=4-6
R10=H or the side chain of a natural amino acid including R10 and R11 together are forming a proline or hydroxy-proline derivative
R11 either is together with R10 forming a proline or hydroxy-proline derivative or is H
R12 is a carbamate protecting group including t-butoxycarbonyl, benzyloxycarbonyl and other N-protecting groups R2:
H, R7, or O—CR8R9, O—CO—CHR10, or NR11R12, with the same definitions of R7-R12 as above R3:
H, F, Cl, Br, I, NH$_2$, NO$_2$, CN, CH$_3$ R4:
H or CH$_3$ R5:
If R4=H, then R5 is an electron pair
if R4=CH$_3$ then R5 is an electron pair, hydrogen or a C$_1$-C$_5$ (ar)alkyl group, CH$_2$—O—CH$_3$, CH$_2$—O—CO—R6, CH$_2$—O—CR8R9, O—CO—CHR10, or NR11R12 with the same definitions of R6 and R8-R12 as above.

In all the latter cases, the nitrogen bears an additional positive charge as well as a counterion, selected from chloride, bromide, iodide, sulphate, nitrate, hydrogensulfate, phosphate, methanesulphonate, tosylate or other pharmaceutically acceptable anion.

Preferred derivatives of the main concept of the invention are quarternary ammonium salts with a labile nitrogen-carbon bond at R5; mono- or diacylderivatives (esters) of the hydroxyl groups of said base compounds (R1, R2); sugar derivatives, preferably glucuronides (R1, R2); derivatives coupled with nicotinic acid (R1, R2); and selected halogenides (R3).

Another preferred derivative of the main concept is a lipophilic dihydropyridinium carrier. This Redox Chemical Delivery System (RCDS; Misra A et al (2003) J Pharm Pharmaceut Sci 6, 252-273) is known to significantly enhance drug delivery through the BBB into the brain parenchyma. Once inside the brain, the dihydropyridinium moiety is enzymatically oxidized to the corresponding ionic pyridinium salt. Subsequent cleavage of the original compound from the carrier leads to liberation of the original compound and to sustained levels of it in the brain tissue.

Other preferred derivatives of the main concept are amino acids that are known to be transported into the brain by active amino acid carriers, e.g., tyrosine. Once inside the brain parenchyma, these derivatives can either directly act on their target molecules or are first enzymatically liberated before acting as the original aren't compound.

As a further aspect of the present invention, the derivatives obtained by chemical modification do not need to work as such as medicaments but rather may initially be pro-drugs that, after penetration though the blood-brain barrier, are converted (e.g., by brain enzymes) to the parent compound or a metabolite thereof and work as such as a medicament. Said pro-drug or derivative is used to prepare a medicament or pharmaceutical composition that preferably can be used for the treatment of brain diseases associated with a cholinergic deficit.

Of the derivatives contained in the general structure of formula (III) and with the proviso and definitions provided there, the following are of particular interest in regard to the present invention, as they have not yet been described or developed under the premise of having higher lipophilicity and/or better BBB transport properties and/or higher brain-to-plasma ratio than their parent compounds (Table 1) from which they are derived by chemical modification:

TABLE 3

Examples of compounds described in previous publications/patents presently shown that they (i) act as cholinergic enhancers, and/or (ii) have higher logP-values than Galantamine

| STRUCTURE | logP | Name |
|---|---|---|
| 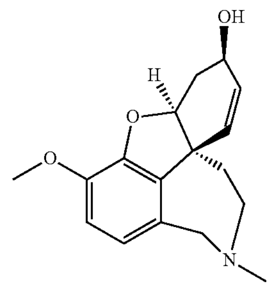 | 1.30 | Galantamine |
| 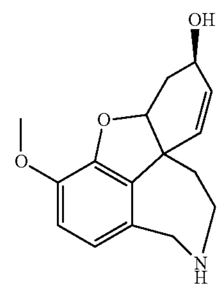 [SMILES: COc1ccc2c3c1OC1C[C@@H](O)C=CC31CCNC2] | 1.38 | Nor-galantamine |
| 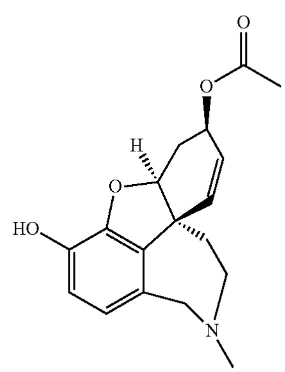 | 1.68 | 3-O-Acetyl-6-O-demethyl-galantamine |
| 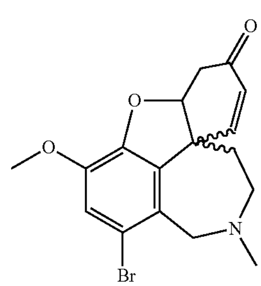 | 1.72 | 8-Bromo-narwedine |

TABLE 3-continued

Examples of compounds described in previous publications/patents presently shown that they (i) act as cholinergic enhancers, and/or (ii) have higher logP-values than Galantamine

| STRUCTURE | logP | Name |
|---|---|---|
| | 1.76 | Narcisine |
| | 1.99 | |
| | 2.15 | |
| | 2.27 | |
| 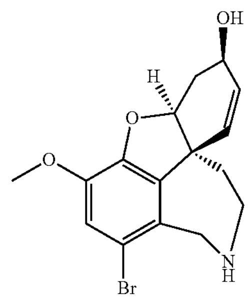 | 2.35 | |
| 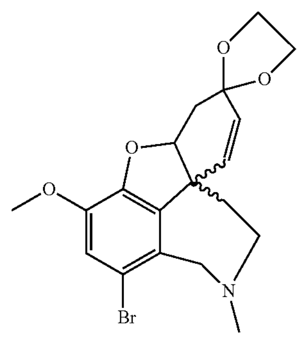 | 2.69 | |
| 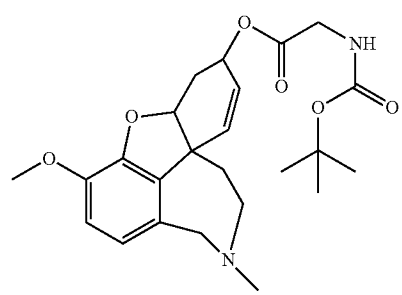 [SMILES: COc1ccc2c3c1OC1CC(OC(=O)CNC(=O)OC(C)(C)C)C=CC31CCN(C)C2] | 3.07 | |
| 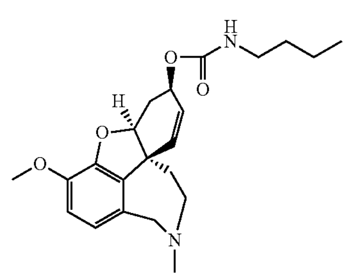 | 3.27 | |
| 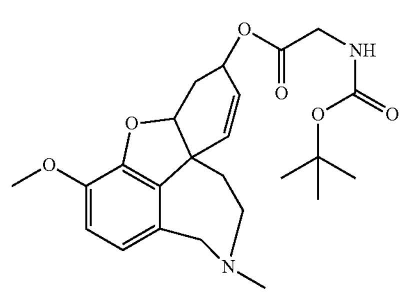 [SMILES: COc1ccc2c3c1OC1CC(OC(=O)CNC(=O)OC(C)(C)C)C=CC31CCN(C)C2] | 4.09 | |

TABLE 3-continued

Examples of compounds described in previous publications/patents presently shown that they (i) act as cholinergic enhancers, and/or (ii) have higher logP-values than Galantamine

| STRUCTURE | logP | Name |
|---|---|---|
| 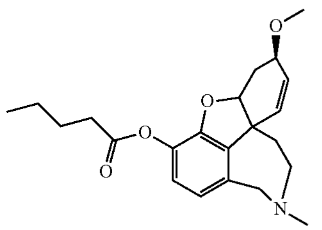 [SMILES: CCCCC(=O)Oc1ccc2c3c1OC1C[C@@H](OC)C=CC31CCN(C)C2] | 4.90 | |

Han, So Yeop; Mayer, Scott C.; Schweiger, Edwin J.; Davis, Bonnie M.; Joullie, Madeleine M. Synthesis and biological activity of galantamine derivatives as acetylcholinesterase (AChE) inhibitors. Bioorganic & Medicinal Chemistry Letters (1991), 1(11), 579-80.

The following derivatives covered by the general structure of formula (III) and with the proviso and definitions provided there are particularly preferred derivatives of the main concept of the invention in that they have not yet been mentioned or described in any other publication or patent.

Examples of new compounds that (i) act as cholinergic enhancers, and/or (ii) have higher log P-values than Galantamine (the latter for comparison only) are shown in FIG. 1.

The derivatives shown in Table 3 and FIG. 1 may be used to prepare a medicament or other pharmaceutical composition. Such medicament or pharmaceutical composition can be used for the treatment of a disease state associated with a cholinergic deficit.

The usefulness of the derivatives, before and/or after conversion to the parent compound, to act as effective pharmaceutical agents is manifested by their ability to sensitize cholinergic receptors, and/or inhibit brain cholinesterases, and/or modulate intracellular messenger levels, and/or act neuroprotective. The ability to act as sensitizing agent on nicotinic receptors can be determined by electrophysiological and Ca-imaging methods, as described in Schrattenholz A et al. (1996) Mol Pharmacol 49, 1-6 and Samochocki M et al (2000) Acta Neuro Scand Suppl 176, 68-73; Samochocki M et al. (2003) J Pharmacol Exp Therap 305, 1024-1036. The ability to inhibit cholinesterases can be determined by the photometric method of Ellman et al., Biochem. Pharmacol. 7, 88 (1961). The ability to modulate intracellular messenger levels can be determined by Ca-imaging methods (Samochocki M et al. (2003) J Pharmacol Exp Therap 305, 1024-1036) and other means of recording changes in intracellular messenger levels or effects resulting thereof (Kihara T et al (2004) Biochem Biophys Res Commun 325, 976-982). The ability to act neuroprotective can be determined by a variety of in vitro and in vivo test systems, including in cell culture (Arias E et al (2003) Neuropharmacol 46, 103-1S 14; Kihara T et al (2004) Biochem Biophys Res Commun 325, 976-982) and in animal models of neurodegenerative diseases (Capsoni et al (2002) Proc Natl Acad Sci USA 99, 12432-12437).

This usefulness can also be ascertained by determining the ability of these compounds (1) to reduce neuronal cell death and amyloid plaque formation as well as cognitive impairment in animal models of Alzheimer's disease (Capsoni et al (2002) Proc Natl Acad Sci USA 99, 12432-12437) and (2) to enhance learning performance in various animal test systems. In one particular learning paradigm applied to old and young rabbits (Woodruff-Pak D et al (2001) Proc Natl Acad Sci USA, 98, 2089-2094), the classical eye blink conditioning is used to study the effect of cognition-enhancing drugs on the septohippocampal cholinergic system. An active test compound of the present invention will reduce the number of trials required to learn that the air blow applied onto the animal's eye does not require the animal to close the eye (eye blink) as a protective measure.

This usefulness can also be ascertained by determining the ability of these compounds to restore deficient memory due to a cholinergic deficit in the Dark Avoidance Assay (DAA). In this assay mice are tested for their ability to remember an unpleasant stimulus for a period of e.g., 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock administered in the dark compartment.

If a nicotinic or muscarinic antagonist, i.e., an anticholinergic drug that causes memory impairment, is administered before an animal's initial exposure to the test chamber, the animal tends to re-enter the dark compartment much sooner than in the absence of the anticholinergic drug when being placed in the test chamber 24 hours later. This effect of an anticholinergic drug is blocked by an active test compound, resulting in a greater interval before re-entry into the dark compartment.

The test results may be expressed as the percent of a group of animals in which the effect of the anticholinergic drug is blocked or reduced, as manifested by an increased time interval between being placed in the test chamber and re-entering the dark compartment.

According to the present intention and approach, the brain disease that can be treated with the pro-drugs and derivatives provided herewith can be any psychiatric, neurological and neurodegenerative disease associated with a cholinergic deficit of any kind, including a neurodegenerative loss of cholinergic neurotransmitters and/or receptors, ACh-synthesizing and metabolizing enzymes, transport proteins and the like. Such diseases are exemplified by Alzheimer's and Parkinson's disease, other types of dementia, schizophrenia, epilepsy, stroke, poliomyelitis, neuritis, myopathy, oxygen and nutrient deficiencies in the brain after hypoxia, anoxia, asphyxia, cardiac arrest, chronic fatique syndrome, various types of poisoning, anesthesia, particularly neuroleptic anesthesia, spinal cord disorders, inflammation, particularly central inflammatory disorders, postoperative delirium and/or subsyndronal postoperative delirium, neuropathic pain, subsequences of the abuse of alcohol and drugs, addictive alcohol and nicotine craving, and subsequences of radiotherapy, and more. The effect of Galantamine or other cholinesterase inhibitors in treatment of such diseases are described e.g., in WO2005/74535, WO2005/72713, WO2005/41979, WO2005/30332, WO2005/27975, US2004/266659 and WO2004/14393.

All the derivatives described in the general (base) structure of formula (III) and Tables 2 and 3 and FIG. 1 either have an effect as a pro-drug, which means that the derivative, after entering the brain, is "converted back" into an effective agent, e.g., Galantamine, Narwedine, Lycoramine, or the other said base compounds, or they are effective (i.e., as cholinergic enhancers or agents according to the definition) as derivatives themselves, meaning that they are not necessarily converted or metabolised before they act as agents at their target molecules, e.g., cholinergic receptors or cholinesterases. The common feature of the derivatives of the present application is that they all penetrate more effectively through the blood-brain barrier than the base compound, which according to the present invention preferably is Galantamine and related compounds. As a result of their improved BBB penetration properties, these compounds should have higher therapeutic efficacy and lower adverse side effects than e.g., Galantamine.

The compounds of the present invention whether pro-drugs or otherwise effective agents can be administered as such or as a pharmaceutically acceptable salt thereof.

The derivatives of the common formulae as defined above can be prepared by any known method, however, it is preferred that the derivatives are prepared with proper use by the methods described for derivatization of according compounds in EP-A 649 846 with reference to scheme I and in the examples; EP-A648 771 with reference to scheme I and in the examples; EP-A 653 427 with reference to scheme I and in the examples; U.S. Pat. No. 6,150,354, paragraph "procedures" and examples; or U.S. Pat. No. 6,638,925, paragraph "experimental section", respectively. A further reference is WO 01/74820, wherein combinatory and/or parallel synthesis is disclosed and synthesis of several compounds is described in the examples. Further the method can be used as described in Gomes, P. et al., Rui. Centro de Investigacao em Quimica da Universidade do Porto, Oporto, Port. Synthetic Communications (2003), 33(10), 1683-1693. A skilled person clearly will understand that in any case an appropriate educt/appropriate educts has/have to be used to obtain the desired derivatization of the base structure. The preparation method is not limiting the invention as long as the compounds presently described are obtained.

The compounds of the invention preferably are prepared from the appropriate optical isomer of Galantamine or Narwedine via the intermediate 6-demethylgalantamine, a known therapeutically effective compound, or 6-demethyl-narwedine, respectively.

The pro-drugs and derivatives of this invention are selected by the following tests, which shall be considered as examples not limiting the invention:
1. Activity as nicotinic "allosterically potentiating ligand (APL), preferentially determined by electrophysiological methods and, Ca-imaging, using human cell lines that express individual subtypes of human neuronal nicotinic acetylcholine receptors (nAChR).
   In the case of a compound acting as such: The activation of nAChR by ACh or agonist is enhanced in the presence of said compound, with the APL activity being selectively blocked by antibody FK1.
   In the case of a pro-drug: Enhanced activity as a centrally acting APL after the pro-drug has been converted to the base compound by treatment with a rat brain or human brain homogenate extract.
   Kinetics of conversion from pro-drug to drug when incubated with a rat or human brain extract.
2. Activity as centrally acting cholinesterase inhibitor, as tested by various in-vitro, cell culture and in-vivo test systems.
   In the case of a pro-drug: Enhanced cholinesterase inhibition—or the same level of inhibition at a significantly reduced dose—is observed when the pro-drug is administered instead of the original base compound.
   Kinetics of conversion from pro-drug to drug when incubated with a rat or human brain extract.
3. Neuroprotective activity in acute toxicity protection tests (organophosphate poisoning of animals, in-vitro poisoning by Aß and/or glutamate) and in animal models of neurodegeneraton.
   In the case of a pro-drug: Enhanced neuroprotective activity—or the same level of neuroprotection at a significantly reduced dose—is observed when the pro-drug is administered instead of the original base compound.
4. Accumulation of the derivatives in the brain of mammals as compared to unmodified Galantamine or other base compound.
5. Lipophilicity, as measured by shake-flask (e.g., octanol/buffer), HPLC-retention and nanobeads absorption methods.
6. Bioconversion $t_{1/2}$ in the brain as compared to blood (systemic).
7. Theoretical/empirical estimates of distribution and log P values.
8. Other miscellaneous tests.

As one way of estimating improved lipophilicity of the derivatized compounds, log P-values are provided in some of the tables. Improved lipophilicity, as characterized by an increased log P-value, can either be determined experimentally including HPLC methods or by predictive computational methods. Although such calculations cannot replace the experiment, the data are strongly suggestive as to whether a certain modification of the base compound will result in an improved lipophilicity. Computer programs that allow such calculations include e.g., ToxBoxes from Pharma Algorithms, ACD-Lab, Molecule Evaluator from Cidrux, and others.

Another means of estimating the readiness of a compound to transverse the BBB is by experimental comparison of the membrane affinity of said compound to its binding affinity to serum albumin, both determined by the NIMBUS Biotechnology assay (Willmann, S. et al. (2005) J Med Chem, in print).

Effective quantities of the compounds of the invention may be administered to a patient by any of various methods, including orally as in capsules or tablets, via the skin or by nasal application. The free base final products, while effective by themselves, may be formulated and administered in the form of a pharmaceutically acceptable salt, e.g., for purposes of stability, convenience of crystallization, increased solubility, release retardation, and the like.

Since the pro-drugs/compounds of the present invention pass the blood-brain-barrier easier than the base compounds, there are two advantageous aspects: first is the fast uptake of the pro-drug and therefore a fast onset of effect, second is that the dosage of application can be decreased compared to known medicaments resulting in lower peripheral side effects with high efficacy of the compounds at their effect site (brain). Further the pro-drugs after passage through the blood-brain-barrier are converted in the base compound which has a lower permeability through the blood-brain-barrier, thus the effective compound remains in the brain, resulting in a longer time period of effectiveness.

As a representative case, the active compounds of the present invention may be orally administered, for example, with an inert diluent or with an edible carrier, or they may be enclosed in gelatine capsules, or they may be compressed into tablets. Furthermore, the active compounds of the invention may be incorporated with excipients and used in the form of tablets, troches, capsules, elixirs, suspensions, syrups, wafers, chewing gum and the like. Preferred compositions and preparations according to the present invention are prepared so that an oral dosage unit form contains between 0.1 and 50 milligrams of active compound.

Because BBB penetration and brain-to-plasma ratio of the compounds modified according to this invention are significantly enhanced, the dosages of administered drug may be dramatically reduced, as compared to previous applications, clinical studies and estimates.

Selected Aromatic and Heterocyclic Derivatives of Galantamine as Pro-Drugs for the Treatment of Human Brain Diseases The proposed derivatives were designed as pro-drugs, in the sense that they are able to effectively pass the blood brain barrier (BBB) and, after passing the BBB, they are substrates of endogenous enzymes and, upon enzymatic cleavage, produce galantamine. As a result of enzymatic cleavage to galantamine of such pro-galantamines in the brain, a significantly higher local concentration of galantamine is achieved in the brain than by administration of the same dose of original galantamine. The relatively higher drug concentration in the brain achieved by pro-galantamine administration will then result in higher efficacy at a given dose, and the better brain-to-peripheral tissues distribution will result in fewer or less significant side effects of treatment. These effects are significant improvements of present treatment regimens because the efficacy as treatment for brain diseases of unmodified galantamine (and all other ChE-I presently approved for this purpose) is rather limited, albeit statistically significant, possibly due to low dosing. Thus, efficacy is usually reached only after careful (months-long) up-titration of daily dose, so as to maintain sufficient compliance of patients to the largely gastro-intestinal side effects associated with ChE-I treatment.

According to some embodiments, it was found that careful selection concerning the type of substituent and the position of substitution using galantamine as base structure result in highly efficacious compounds. Such very efficacious compounds having good blood brain barrier passing properties and being efficiently cleaved by an esterase after passage through the BBB are obtained with compounds having the general formula V

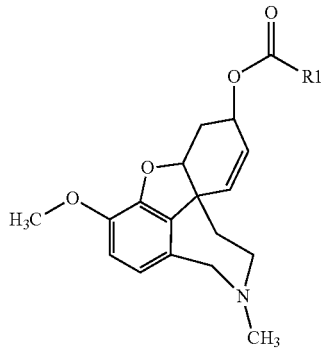

with R1 being a substituent having particular sterical and hydrophobic properties.

These embodiments focus on esters of galantamine that, as such, have little or no activity as ChE-I and APL compared to galantamine. Therefore, as long as these compounds remain uncleaved, they do not interact with the usual target molecules of galantamine and hence are largely inactive in producing therapeutic and/or side effects. The reduced reactivity of pro-galantamines is demonstrated by the following results:

1. Significantly reduced activity as ChE-I, as compared to galantamine.
2. Reduced activity as nicotinic APL, as compared to galantamine.
3. Reduced gastro-intestinal side effects, as compared to galantamine.

All these approaches were investigated and are explained in the examples and shown in the figures.

According to the invention it has been discovered that a particular group of esters of galantamine display unexpectedly high brain-to-blood concentration ratios ($R_{BB}$-pro-Gal>6, as compared to $R_{BB}$-Gal ~1.3) and in the brain they are relatively slowly enzymatically cleaved to galantamine. Therefore, as is discussed below in more detail, these pro-galantamines are exceptionally well suited for the treatment of human diseases associated with cholinergic deficits, such as Alzheimer's disease, Parkinson's disease, Schizophrenia and a variety of other psychiatric disorders.

The esters of galantamine to which the present invention refers to have the following general structure:

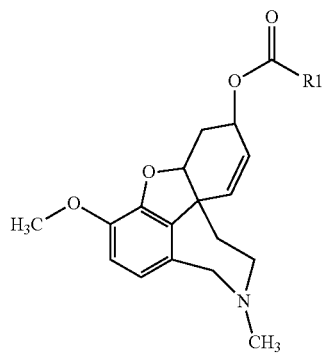

Formula V wherein R1 either is $CH(C_2H_5)CH_3$, $CH_2-C(CH_3)_3$, or cyclopropane or being an optionally substituted aromatic or hetero-aromatic 5- or 6-membered ring. Specifically, such aromatic and hetero-aromatic rings include benzene, naphthalene, thiophene, pyrrole, imidazole, pyrazole, oxazole and thiazole, in case that they are used as medicaments or pro-drugs for the treatment of neurodegenerative or psychiatric or neurological disease associated with a cholinergic deficit.

Such a disease preferably is selected from Alzheimer's and Parkinson's disease, other types of dementia, schizophrenia, epilepsy, neuritis, various types of poisoning, anesthesia, particularly neuroleptic anesthesia, autism, spinal cord disorders, inflammation, particularly central inflammatory disorders, postoperative delirium and/or subsyndromal postoperative delirium, neuropathic pain, subsequences of the abuse of alcohol and drugs, addictive alcohol and nicotine craving, and subsequences of radiotherapy.

The above mentioned compounds were not yet described for the treatment of such diseases. Furthermore, compounds of formula I having aromatic or hetero-aromatic 5- or 6-membered ring, selected from substituted benzene with the proviso that it is not 2-fluorobenzene or 3-nitro-4-fluorobenzene, optionally substituted naphthalene, thiophene, pyrrole, imidazole, pyrazole, oxazole, thiazole; or $CH(C_2H_5)CH_3$, $CH_2-C(CH_3)_3$, or cyclopropane are according to the knowledge of the inventor not yet described at all.

In one preferred embodiment the compounds of the present invention are selected from

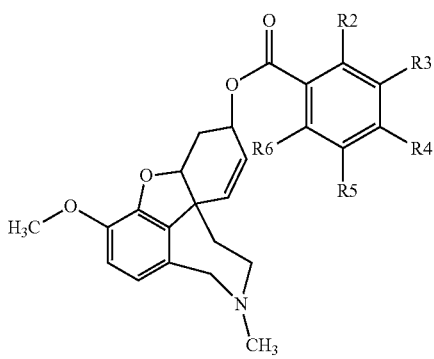

Formula VI wherein R2-R6 comprising any substituent selected from H, halogen, optionally substituted $C_1$-$C_3$ alkyl or cyclopropyl, OH, O-alkyl, SH, S-alkyl, $NH_2$, NH-alkyl, N-dialkyl, optionally substituted aryl or hetero-aryl, whereby neighbouring substitutents can cooperate to form an additional ring.

In another preferred embodiment of the present invention the compounds are selected from the group consisting of the compounds as shown in table A, which is attached below.

Herein the term "pro-drug" refers to a derivative of galantamine (base compound) wherein the group(s) added or replaced on said base compound are cleaved or returned to the hydroxyl group originally contained in the base compound, when the derivative has reached the area or site of action. Thus, in case of a "pro-drug", an effective agent is administrated as a derivative (which is said pro-drug), however, the compound mainly or exclusively effective at the target site within the brain is the agent itself, not the derivatized compound or metabolites other than the base compound thereof.

The term "derivative" refers to any change of a base compound defined in the present application. The term "derivative" is used to describe a compound which either can be a pro-drug, or can be an effective agent itself/in its own right or in the derivatized form.

The term "pro-galantamine" is used for any derivative of galantamine described herein which can be cleaved by an enzyme (esterase) resulting in galantamine.

The terms "sensitizing agent" and "allosterically potentiating ligand, APL" refer to effectors that enhance cholinergic neurotransmission by interaction with an allosteric site at cholinergic receptors.

The terms "cholinergic enhancer" and "cholinergic agent" refer to compounds that enhance/modulate cholinergic neurotransmission by inhibition of cholinesterases, by allosteric sensitization and/or direct activation of cholinergic receptors and/or by activating/modulating relevant intracellular pathways via second messenger cascades.

A derivative or pro-drug has an "enhanced blood-brain barrier permeability "according to the present invention or an "enhanced blood-brain barrier penetration" if, after administration of a pro-drug or derivative thereof to a living organism, a higher amount of said compound penetrates through the BBB of that organism.

A compound of the present invention provides an increased "brain-to-blood concentration ratio" or "brain-to-tissue concentration ratio" resulting in a higher level of effective agent in the brain, as compared to administration of the base compound without derivatization. Methods for determination of an enhanced BBB permeability are disclosed in WO 2007/039138.

The "base compound" as well as the "effective agent" according to the present invention is galantamine. The effective agent is obtained by (local) enzymatic cleavage of the derivative.

"log P" is defined as the decadic logarithm of the partition coefficient P which is the ratio of the concentration of a compound in aqueous phase to the concentration of a compound in immiscible solvent, as the neutral molecule.

The term "alkyl" shall mean a straight, branched or cyclic alkyl group. As "alkyl" $C_1$ to $C_{10}$ alkyl groups are preferred, $C_2$ to $C_8$ groups are more preferred and $C_2$ to $C_6$ groups are most preferred. $C_1$ to $C_{10}$ means alkyl groups of the stated number of carbon atoms. Examples include, but are not limited to methyl, ethyl, n-propyl, iso-propyl, n-butyl, isobutyl, sec-butyl, t-butyl, and straight and branched chain pentyl, hexyl, heptyl, octyl, nonyl and decyl etc. . . . or the according cyclic alkyls.

The term "halo" shall mean chloro, fluoro, bromo and iodo.

The term "aryl" shall mean phenyl having 0, 1, 2, 3, 4 or 5 substituents independently selected from the group of alkyl, alkoxy, alkylcarbonyl, halo- or trihalomethyl.

The term "cycloalkyl" shall mean a cycloalkyl group of from 3 to 10 carbon atoms and including multiple ring alkyls such as for example, adamantyl, camphoryl, and 3-noradamantyl.

In any case when a range between two limits is described it is meant that any value or integer in this range is disclosed. For example "$C_1$-$C_{10}$" means $C_1$, $C_2$, $C_3$, $C_4$, $C_5$, $C_6$, $C_7$, $C_8$, $C_9$ or $C_{10}$; or "between 0,1 and 1" means 0,1, 0,2, 0,3, 0,4, 0,5, 0,6, 0,7, 0,8, 0,9 or 1.

The stereo chemistry of the described derivatives are the same as that of galantamine.

Benzoyl esters of galantamine were previously described in WO 9921561 A1 Davis, Bonnie M. for a method of treatment of disorders of attention with galantamine, lycoramine, and related compounds, but no syntheses or analytical or other data were provided for these compounds.

Substituted benzoyl esters were previously described in "Synthesis and biological activity of galantamine derivatives as acetylcholinesterase (AChE) inhibitors" by Han, So Yeop; Mayer, Scott C.; Schweiger, Edwin J.; Davis, Bonnie M.; Joullie, Madeleine M. Dep. Chem., Univ. Pennsylvania, Philadelphia, Pa., USA. Bioorganic & Medicinal Chemistry Letters (1991), 1(11), 579-80. CODEN: BMCLE8 ISSN: 0960-894X. Journal written in English. CAN 116:83569 AN 1992:83569 CAPLUS. In this document the synthesis of several ester and carbamate derivatives of galantamine are described as well as it was suggested that these compounds are potential therapeutic agents in the treatment of Alzheimer's disease, based on their properties as AChE inhibitors.

In contrast to the teaching of these documents, the galantamine esters of the present invention have little, if any, activity as acetylcholinesterase inhibitors but rather are substrates of said enzyme (see above).

Figure 2:
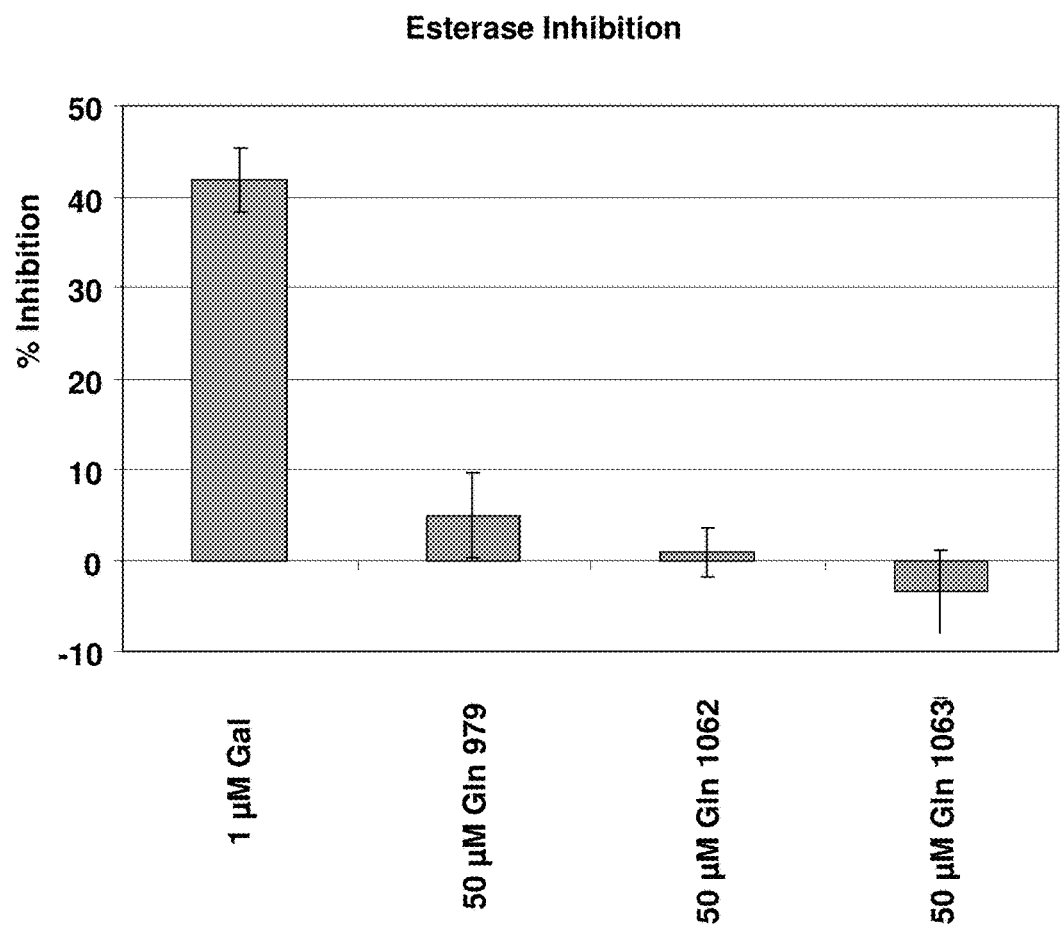
FIG. 2: Brain esterase inhibition by galantamine and several pro-galantamines. A 20% mouse brain homogenate was used, supplemented with 200 μM of acetylthiocholine as substrate, and the initial reaction kinetics were measured according to Riddles P W, Blakeley R L, Zerner B., "Reassessment of Ellman's reagent" Methods Enzymol. 1983, 91:49-60. As shown in the figure, even 50 μM of the respective pro-galantamines were unable to achieve a level of inhibition of brain cholinesterase that is comparable in size to that of 1 μM galantamine. A non-cleavable galantamine derivative (Gln 1063) leads to negative values. In derivative Gln 1063 R1 in Formula V is —O—Si$(CH_3)_2$—C$(CH_3)_2$—C$(CH_3)_2$H.

As representatively demonstrated for the benzoyl derivative in FIG. 2, these esters have little, if any cholinesterase inhibitory activity but rather are hydrolysed by cholinesterases to form galantamine and accordingly act as pro-drugs of galantamine. As soon as galantamine is generated from these compounds, it acts as ChE-I and APL, as has previously been described. The structures of the tested derivatives can be seen in Table 4. As a comparative derivative a non-cleavable galantamine ether is also tested. Such derivative results in negative values of inhibition. In derivative Gln 1063 R1 in formula V is —O—Si(CH$_3$)$_2$—C(CH$_3$)$_2$—C(CH$_3$)$_2$H.

TABLE 4

| Mol Reg. No. | Molecular structure | Abbreviation |
| --- | --- | --- |
| GLN-1062 | 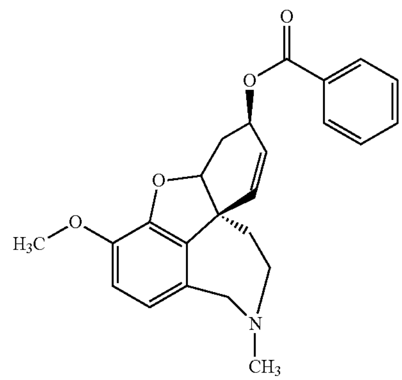 | Bz—Gal |
| GLN-1081 | 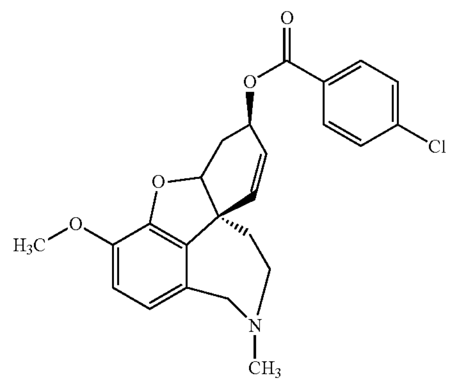 | 4-Cl—Bz—Gal |
| GLN-1082 | 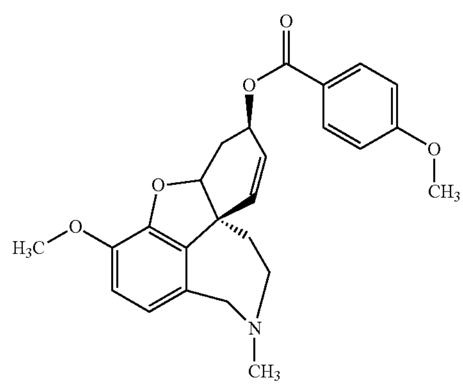 | 4-MeO—Bz—Gal |
| GLN-1083 | 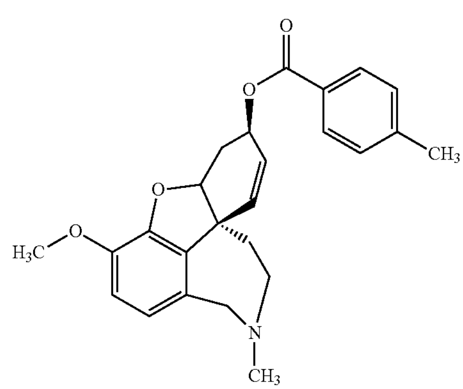 | 4-Me—Bz—Gal |

TABLE 4-continued

| Mol Reg. No. | Molecular structure | Abbreviation |
|---|---|---|
| GLN-1084 | 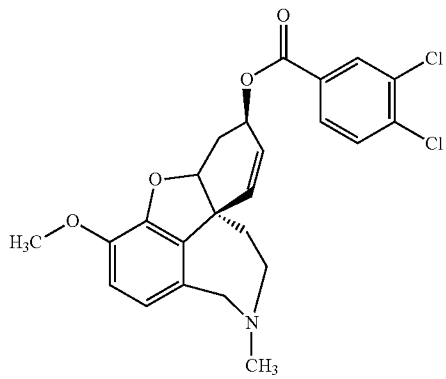 | 3,4-Cl2—Bz—Gal |
| GLN-1085 | 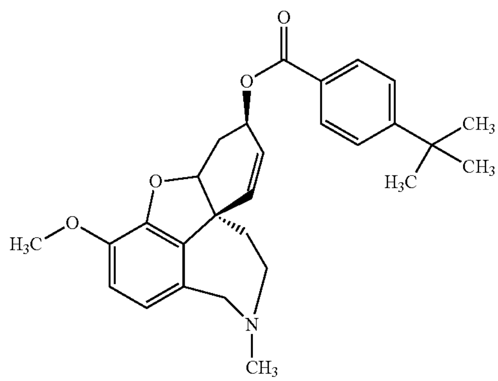 | 4-tBu—Bz—Gal |
| GLN-1086 | 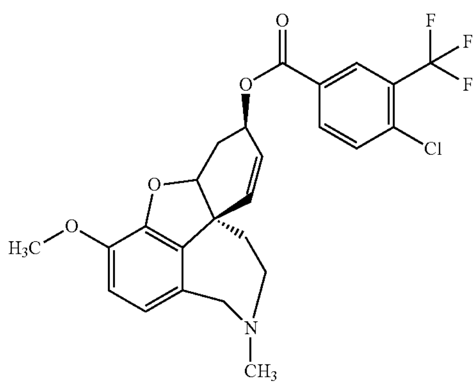 | 3-CF3-4-Cl—Bz—Gal |
| GLN-1088 | 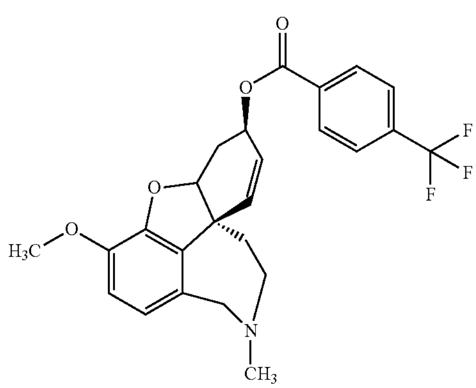 | 4-CF3—Bz—Gal |

TABLE 4-continued

| Mol Reg. No. | Molecular structure | Abbreviation |
|---|---|---|
| GLN-1089 | 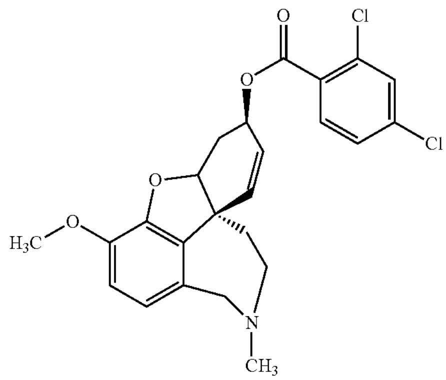 | 2,4-Cl2—Bz—Gal |
| GLN-1090 | 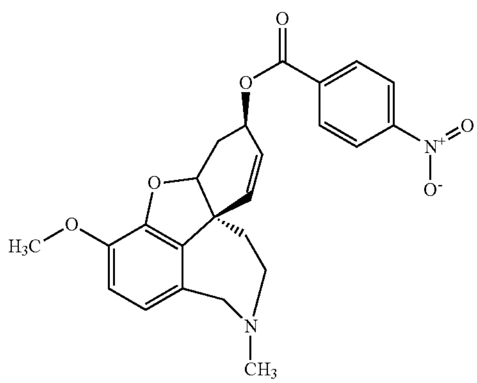 | 4-NO2—Bz—Gal |
| GLN-1091 | 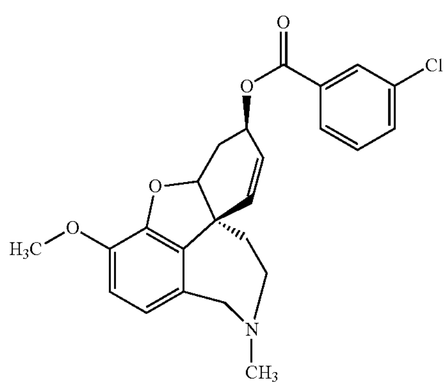 | 3-Cl—Bz—Gal |
| GLN-1092 | 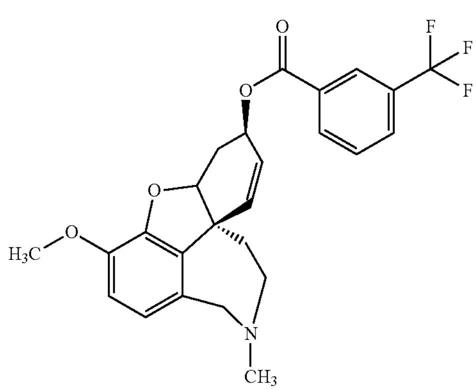 | 3-CF3—Bz—Gal |

TABLE 4-continued
| Mol Reg. No. | Molecular structure | Abbreviation |
|---|---|---|
| GLN-1093 | 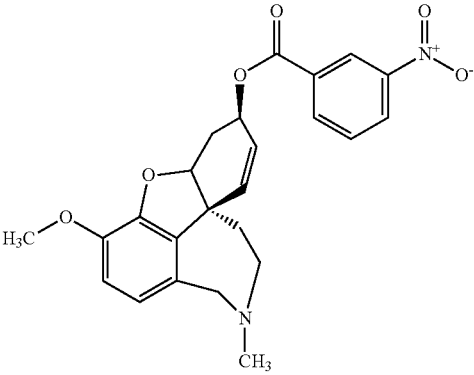 | 3-NO2—Bz—Gal |
| GLN-1094 | 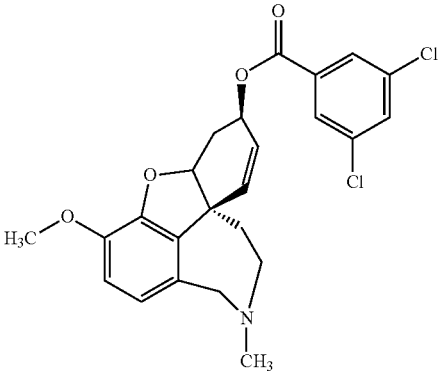 | 3,5-Cl2—Bz—Gal |
| GLN-1095 | 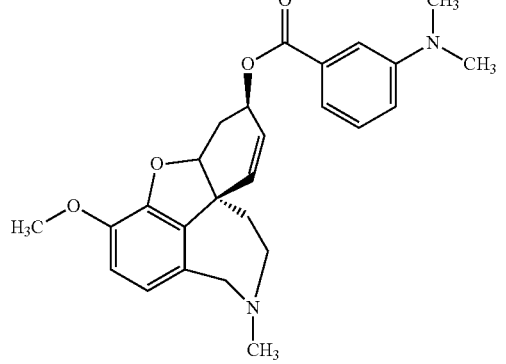 | 3-Me2N—Bz—Gal |
| GLN-1096 | 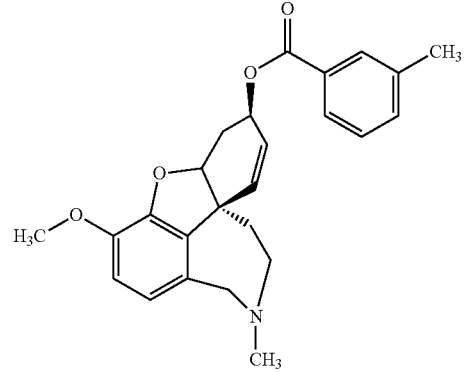 | 3-Me—Bz—Gal |

TABLE 4-continued

| Mol Reg. No. | Molecular structure | Abbreviation |
| --- | --- | --- |
| GLN-1097 | 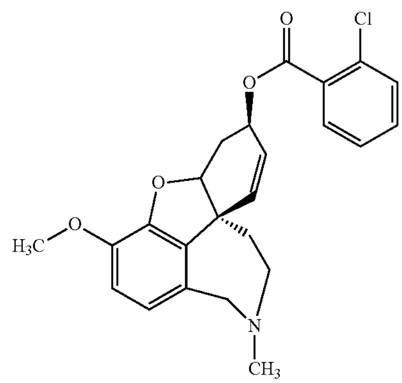 | 2-Cl—Bz—Gal |
| GLN-1098 | 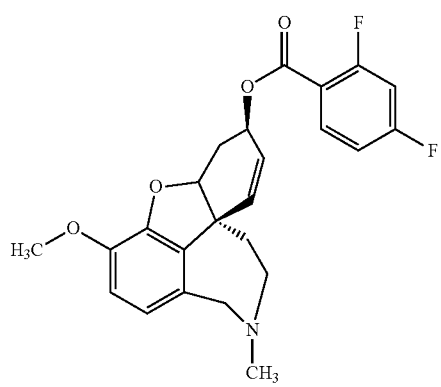 | 2,4-F2—Bz—Gal |
| GLN-1099 | 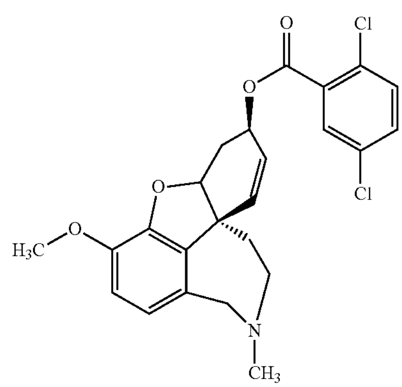 | 2,5-Cl2—Bz—Gal |
| GLN-1100 | 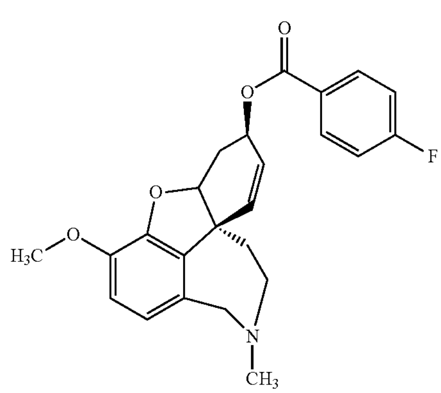 | 4-F—Bz—Gal |

TABLE 4-continued

| Mol Reg. No. | Molecular structure | Abbreviation |
| --- | --- | --- |
| GLN-1101 | 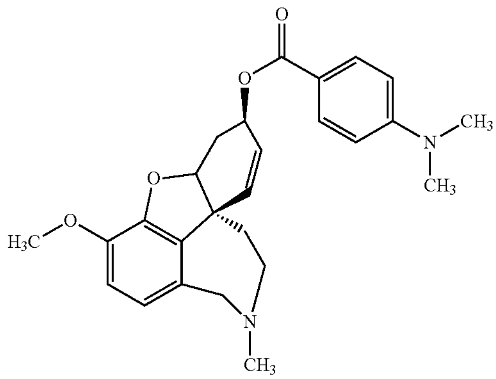 | 4-NMe2—Bz—Gal |
| GLN-1102 | 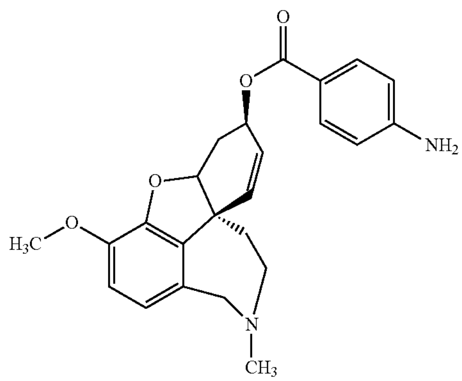 | 4-NH2—Bz—Gal |
| GLN-1103 | 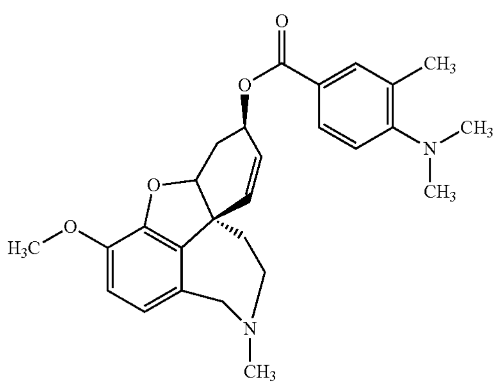 | 3-Me-4-NMe2—Bz—Gal |
| GLN-1104 | 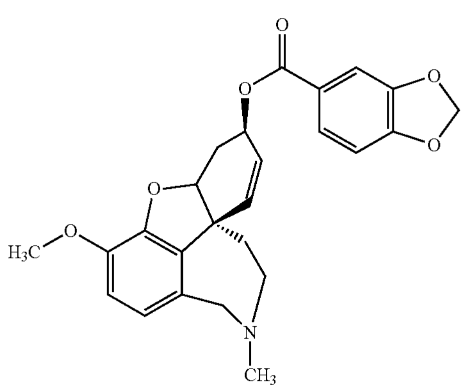 | 3,4-OCH2O—Bz—Gal |

TABLE 4-continued

| Mol Reg. No. | Molecular structure | Abbreviation |
| --- | --- | --- |
| GLN-1105 | 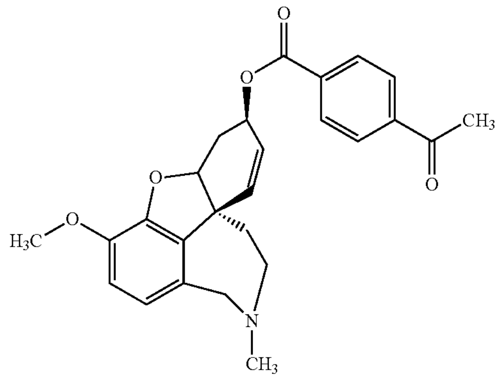 | 4-Ac—Bz—Gal |
| GLN-1113 | 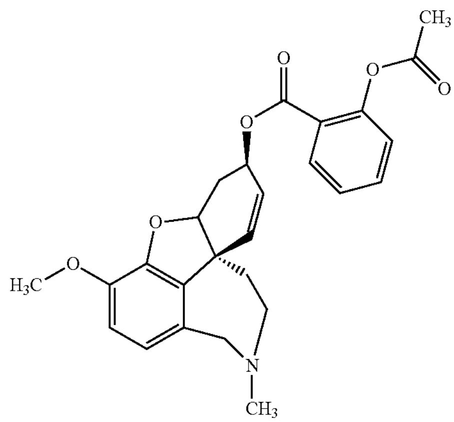 | 2-AcO—Bz—Gal |
| GLN-0978 | 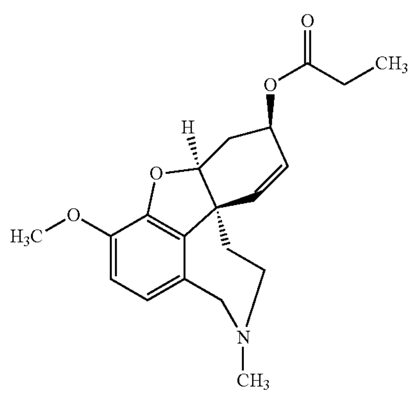 | n-prop-Gal |
| GLN-0979 | 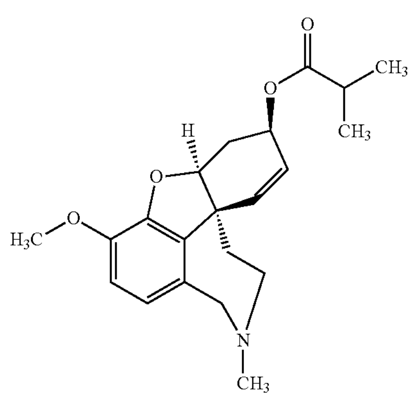 | i-but-Gal |

TABLE 4-continued

| Mol Reg. No. | Molecular structure | Abbreviation |
|---|---|---|
| GLN-0992 | 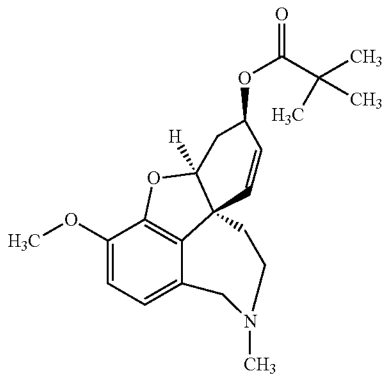 | |
| GLN-0993 | 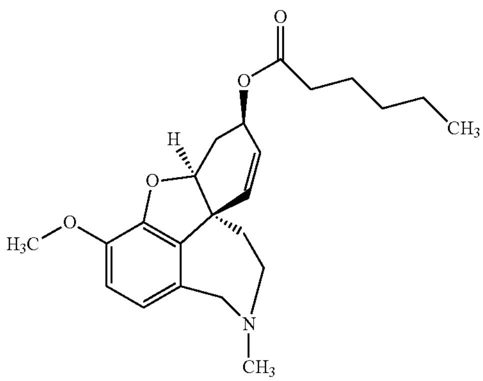 | n-Hex-Gal |
| GLN-1011 | 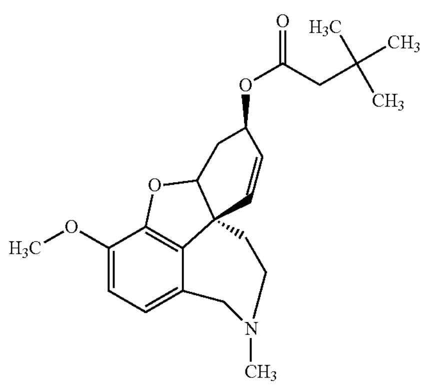 | neo-pent-Gal |
| GLN-1060 | 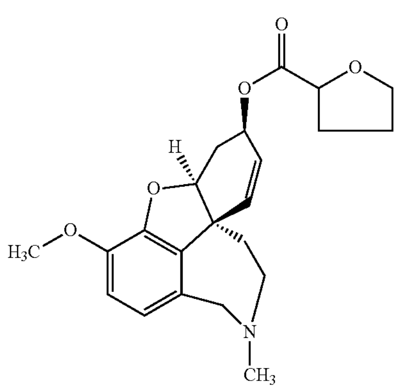 | |

TABLE 4-continued
| Mol Reg. No. | Molecular structure | Abbreviation |
|---|---|---|
| GLN-1061 | 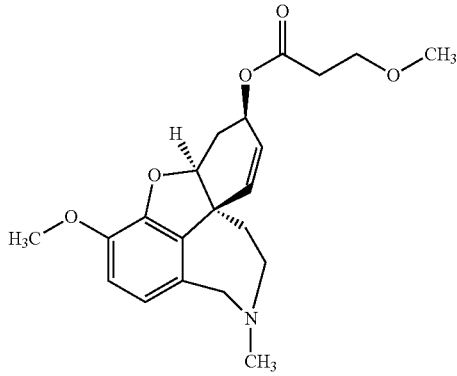 | |
| GLN-1067 | 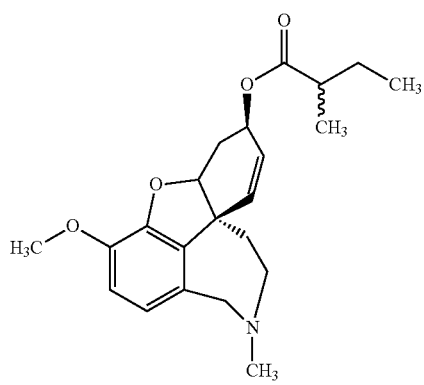 | R/S-i-pent-Gal |
| GLN-1069 | 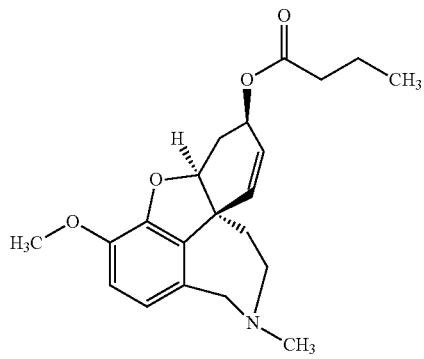 | |
| GLN-1070 | 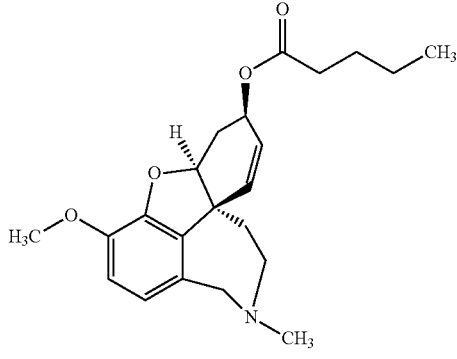 | |

TABLE 4-continued

| Mol Reg. No. | Molecular structure | Abbreviation |
|---|---|---|
| GLN-1071 | 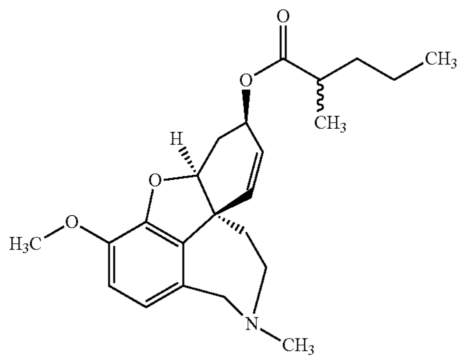 | |
| GLN-1076 | 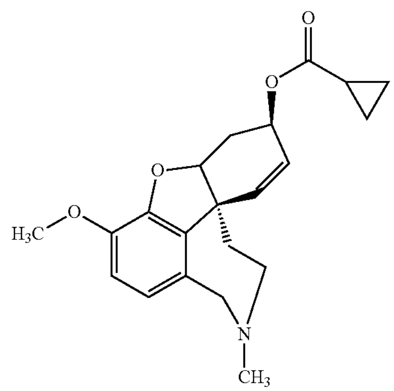 | CyBu—Gal |
| GLN-1077 | 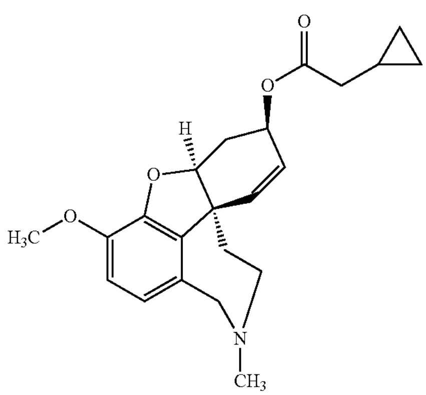 | |
| GLN-1080 | 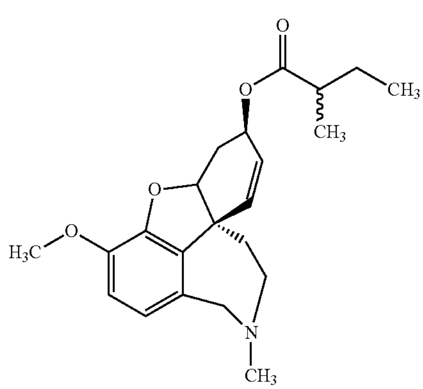 | R/S-i-pent-Gal |

TABLE 4-continued

| Mol Reg. No. | Molecular structure | Abbreviation |
| --- | --- | --- |
| GLN-1106 | 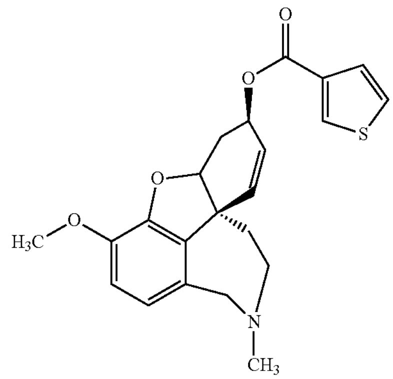 | 3-Th—Bz—Gal |
| GLN-1107 | 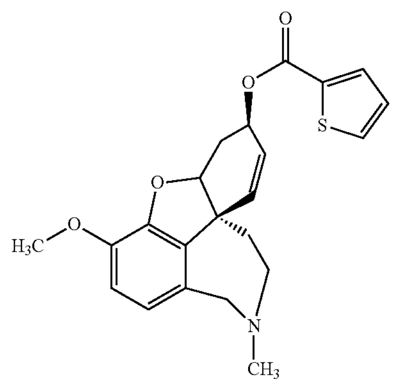 | 2-Th—Bz—Gal |
| GLN-1108 | 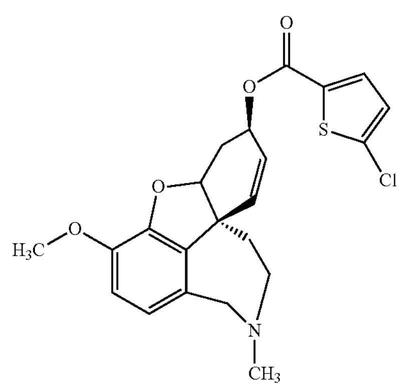 | 5-Cl-2-Th—Bz—Gal |
| GLN-1109 | 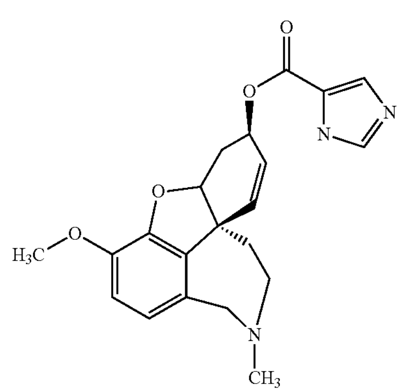 | 5-Im—Bz—Gal |

TABLE 4-continued

| Mol Reg. No. | Molecular structure | Abbreviation |
|---|---|---|
| GLN-1110 | 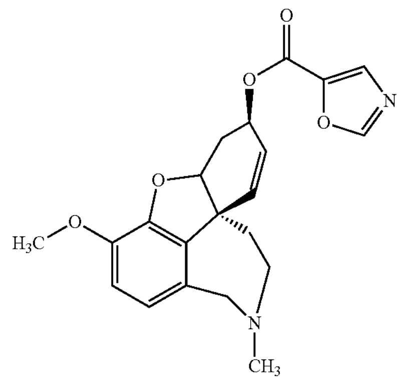 | 5-OA—Bz—Gal |
| GLN-1111 | 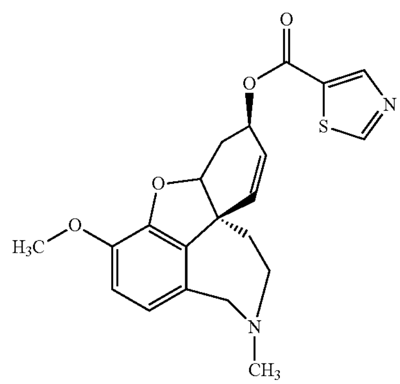 | 5-Th—Bz—Gal |
| GLN-0926 | 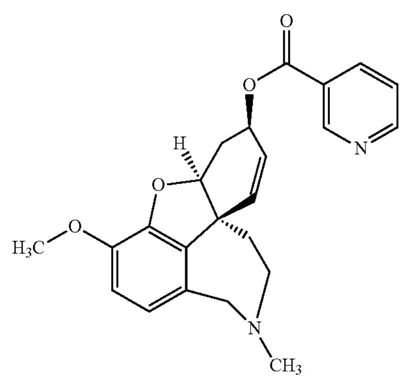 | Nic—Gal |
| GLN-1066 | 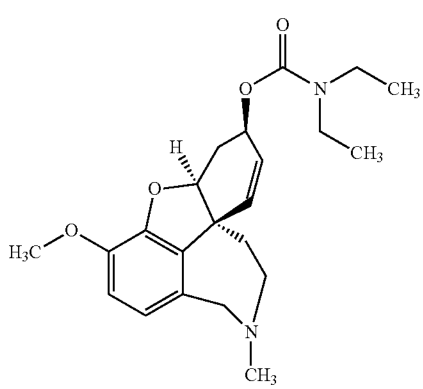 | |

Figure 3:
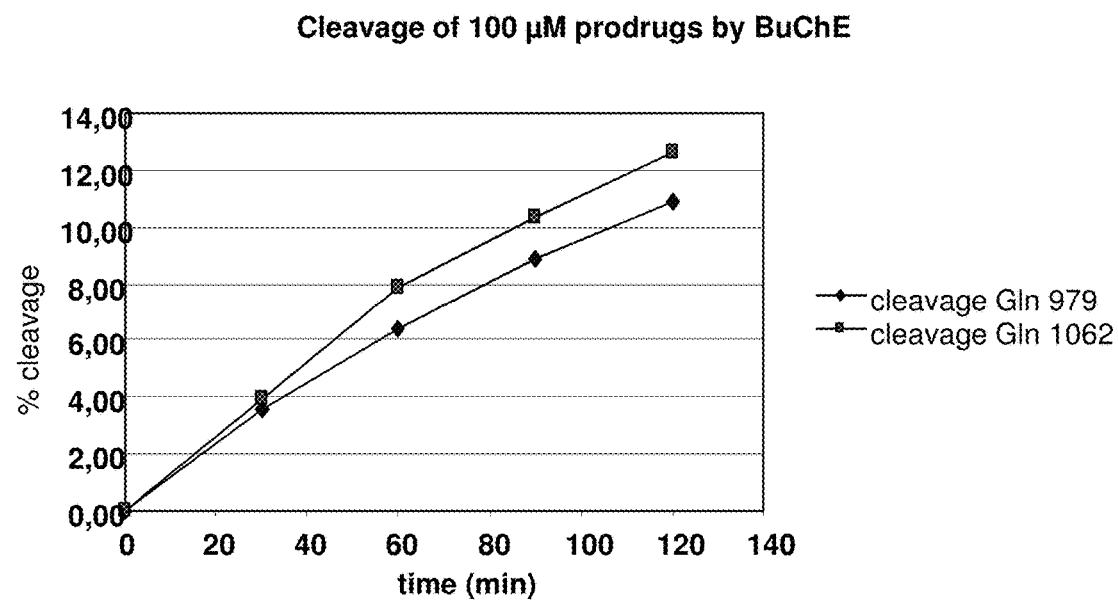
FIG. 3: Enzymatic cleavage of pro-galantamine to galantamine. Butyrylcholinesterase, 25 units/ml, was used. Reaction temperature was 37° C. Appearance of the fluorescent reaction product galantamine was determined by fluorescence detection.

Rather than inhibiting cholinesterases, the pro-galantamines referred to in the present document are substrates of the enzyme, as is exemplarily demonstrated in FIG. 3.

Figure 4:
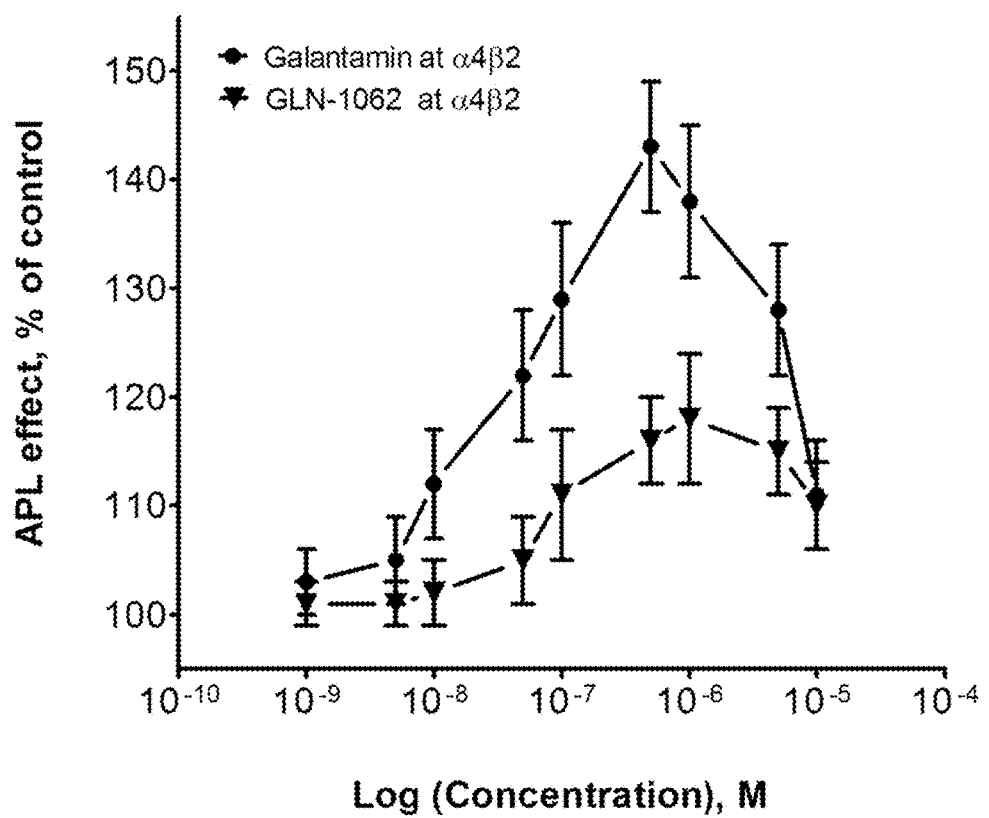
FIG. 4: Interaction of galantamine and pro-galantamine with a4ß2 neuronal nicotinic acetylcholine receptor ectopically expressed in HEK-293 cells. The increase in response to acetylcholine in the presence of galantamine and Gln-1062, respectively, was determined by whole-cell patch clamp recording. Galantamine achieved a maximal enhancement of response of ~40% whereas the pro-galantamine achieved a maximal enhancement of only ~17%.

The data of FIGS. 2 and 3 demonstrate that pro-galantamines of the present invention do not act as efficient inhibitors of cholinesterase, as was described in the earlier documents discussed above. Instead, they are substrates of these enzymes. Similarly, they also do not interact to the same extend as galantamine with neuronal nicotinic acetylcholine receptors (FIG. 4).

The pro-galantamines of the present invention therefore either do not interact, or only to a very limited extend, with the established target molecules of galantamine, in particular cholinesterases and neuronal nicotinic acetylcholine receptors. As pro-drugs they therefore have rather limited, if any, efficacy as cognition enhancers, and also produce only limited peripheral and central side effects, as compared to galantamine (see further below).

Figure 5:
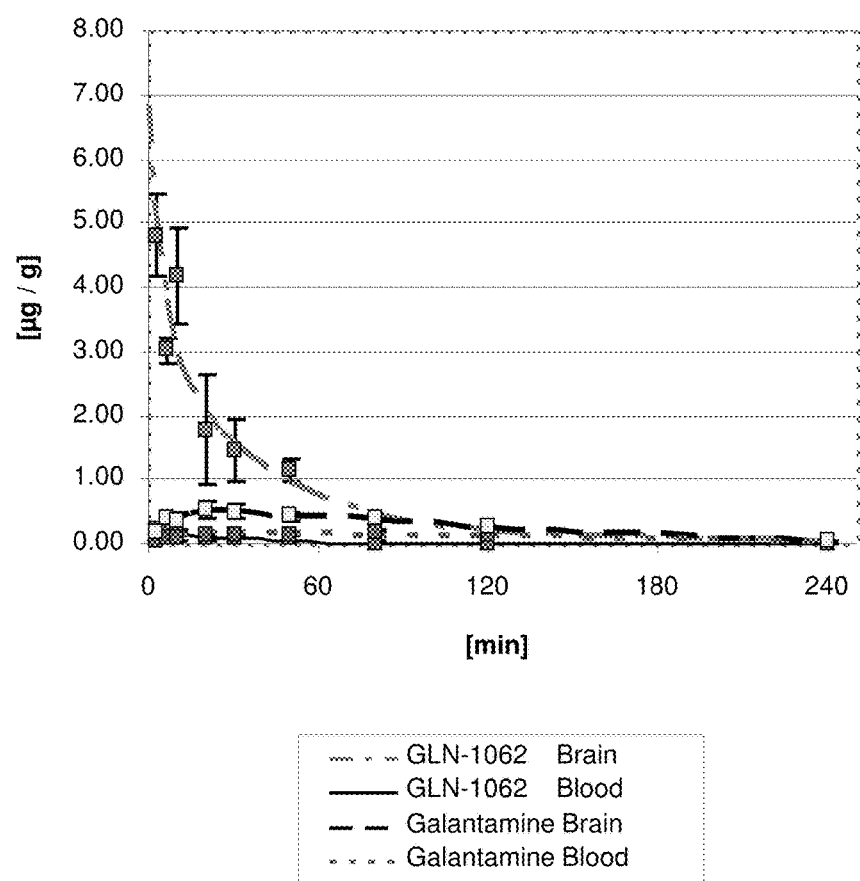
FIG. 5: Pharmacokinetics of pro-galantamine Gln-1062 (3 mg/kg) in the mouse. (A) shows the measurable concentration of applied pro-galantamine and the resulting concentration of galantamine by cleavage of the pro-galantamine in brain and blood. The curve starting with the highest concentration refers to derivative GLN-1062, which is benzoylgalantamine, in brain. (B) is an excerpt ("zoom") of (A), showing the concentration range between 0.00 and 1.00 μg/g (substance/body weight) more in detail. In (B), the curve above refers to the concentration of resulting galantamine in brain, the middle curve shows the concentration of galantamine in blood and the curve starting with a concentration of about 0.3 μg/g and decreasing refers to the concentration of GLN-1062 in blood.
Figure 5:
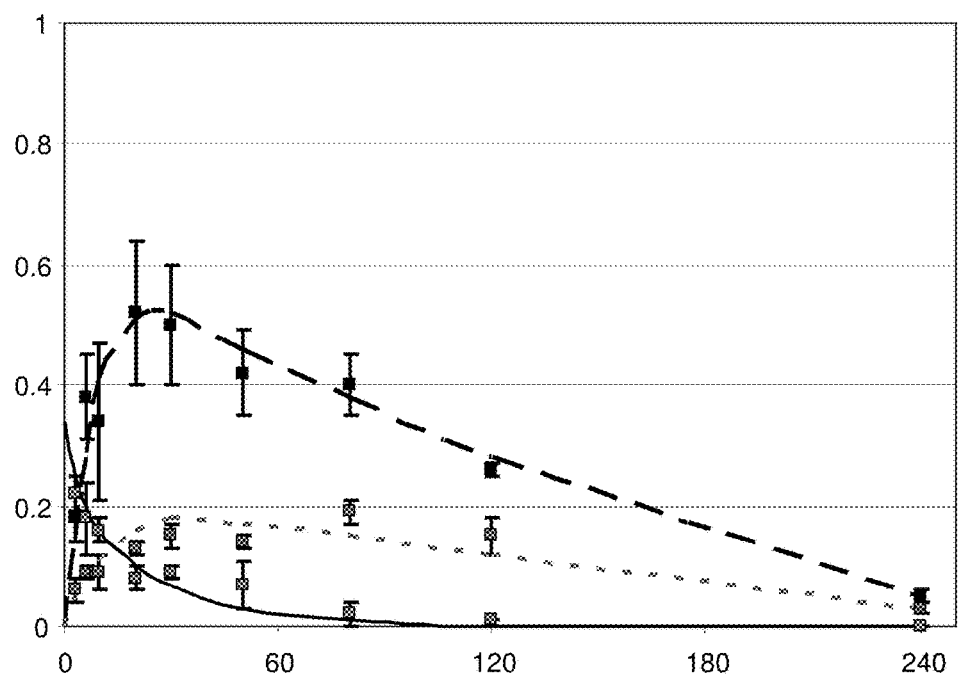

As is exemplified and demonstrated by pharmacokinetics in mice (FIGS. 5a and 5b, Table 5), R1-benzoyl-galantamine displays an unexpectedly high brain-to-blood concentration ratio ($R_{BB}$-proGal >19), a large initial concentration in the brain, and it is only slowly cleaved to galantamine, as seen in the delayed appearance of a galantamine peak in brain and blood. The $R_{BB}$-Value is significantly larger than what was expected from the log P value which probably is due to the slow cleavage of the pro-drug in the brain and a depot effect thereby produced.

In Table 5, the key pharmacokinetic data of benzoyl-galantamine, of several other R1-pro-galantamines and of galantamine (for comparison) are listed.

TABLE 5

Pharmacokinetic data of several R1-pro-galantamines in the mouse

| Gln number (for reference see table 4) | logP | Co (Brain) | R-Pro | R-Gal |
|---|---|---|---|---|
| 1062 | 3.0 | 4812 | 19.3 | 2.2 |
| 1067 | 2.8 | 4665 | 7.5 | 1.7 |
| 0979 | 2.5 | 3166 | 6.2 | 79.4 |
| 0993 | 3.7 | 2150 | 6.4 | 0.6 |
| 0978 | 7.2 | 1985 | 6.9 | 2.3 |
| 1076 | 7.4 | 1245 | 1.1 | 1.0 |
| Gal | 1.7 | 1741 |  | 1.2 |

Co is the highest pro-galantamine concentration (ng/ml) achieved in mouse brain after i.v. injection of 3 mg/kg of pro-galantamine. R-Pro ist he brain-to-blood concentration ratio of pro-galantamine, R-Gal that of galantamine under these experimental conditions. For comparison, Co and R-Gal are also provided for i.v. injection of the same amount of galantamine.

These data establish that only a particular selection of R1 substitutions is capable of producing the following advantageous properties of pro-galantamines: high initial concentration in the brain, large $R_{BB}$, and slow enzymatic conversion to galantamine. In addition (not shown in the table), the preferred R1-prodrugs display little, if any side effects, as they are only very slowly converted to galantamine, thereby largely protecting them from acting as galantamine while being transported from the site of administration to the sites of action in the brain.

These properties may have significant impact for the use of these compounds as drugs in Alzheimer's disease and other brain diseases. As is representatively shown in FIG. 5, R1-pro-galantamines of the present invention display in ferrets much less gastro-intestinal side effects than galantamine. Ferrets were used in these studies as they are known to be particularly sensitive to gastro-intestinal side effects. In addition to the classical emetic responses to galantamine and other ChE inhibitors, we recorded salivation (SA), shivering (SH), respiratory problems (RP) and diarrhea (DI) at the levels "none; 0", "moderate; 0.5" (behaviour observed at low frequency and/or at low intensity) and "intense; 1.0" (behaviour observed frequently and/or continuously and/or at high intensity), and summated the scores for the four animals each used per drug dose in these studies.

Figure 6:
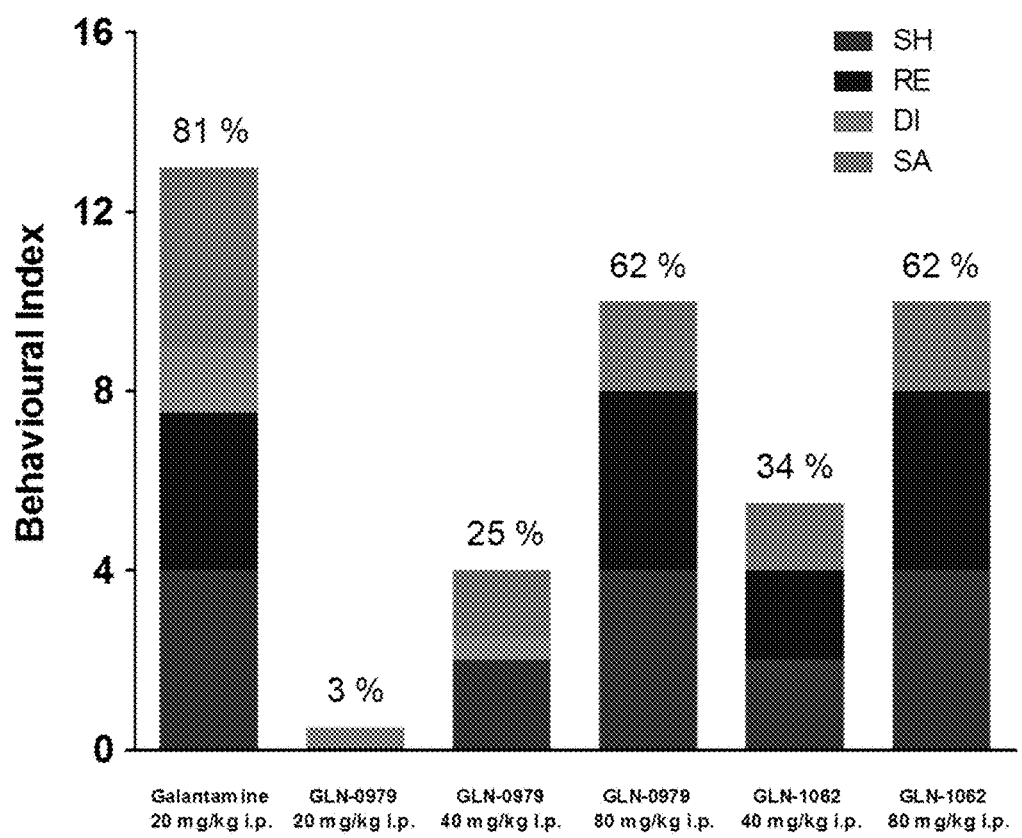
FIG. 6: Behavioral index for gastro-intestinal side effects in ferrets following application of galantamine and several R1-pro-galantamines, respectively.

The data depicted in FIG. 6 for the two pro-galantamines demonstrate that their side effects profile in ferrets is much less severe (5-6 times less) than that of the same dose of galantamine. The advantageous side effects profile is probably due to the reduced affinity of interaction of these R1-pro-galantamines with cholinesterases and neuronal nicotinic acetylcholine receptors (FIGS. 2, 4).

Figure 7:
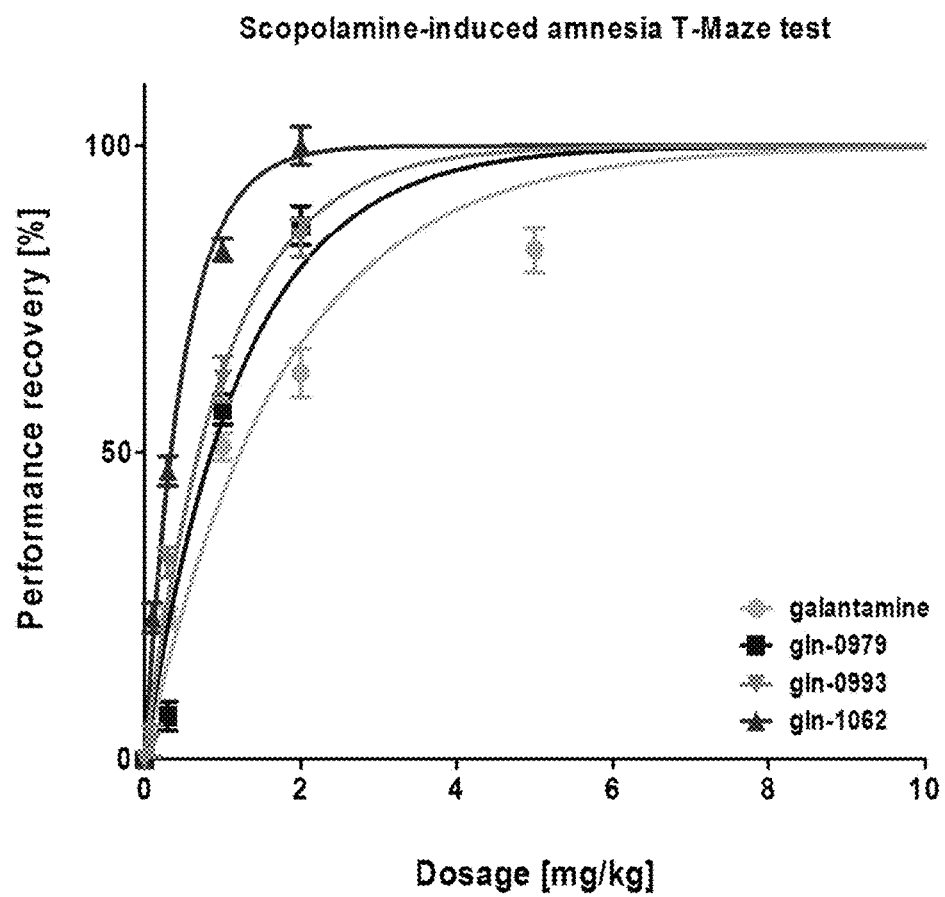
FIG. 7: Reversal from scopolamine-induced amnesia in mice, in the presence of galantamine and several R1-pro-galantamines, respectively. Scopolamine induces a memory deficit that can be measured by increased alternation in a T-maze trial. The cognition enhancing drugs were i.p. injected at several different doses together with scopolamine 20 min before a T-maze trial. Recovery was measured as a function of dose, and the $EC_{50}$ was determined for each drug.

The advantages of enhanced transport of selected R1-produgs through the blood-brain barrier into the brain, enzymatic conversion to galantamine close to target sites in the central nervous system, and interaction with such sites is producing enhanced reversal of drug-induced amnesia in mice, as is shown in FIG. 7 for three pro-glantamines (and for galantamine in comparison).

The data of FIG. 7 suggest that Gln-1062 is approximately 4-times more potent than galantamine in reversing scopolamine-induced amnesia in mice. It may be expected that a similar or larger increase in drug efficacy can be achieved in man when the particular R1-pro-galantamine is administered instead of galantamine. The advantageous drug properties of R1-pro-galantamines (higher efficacy, lesser or less intense side effects) were also shown in other animal models.

In summary, the compounds of this invention are particularly useful as medicaments for the treatment of human brain diseases associated with a cholinergic deficit, including the neurodegenerative diseases Alzheimer's and Parkinson's disease and the neurological/psychiatric diseases vascular dementia, schizophrenia and epilepsy. Based on preclinical studies using various animal models, the compounds have dramatically reduced side effects as compared to galantamine, including much fewer, if any, incidents of emetic responses, diarrhea and vomiting. Moreover, when enzymatically cleaved, the resulting galantamine displays an advantageous pharmacokinetic profile in the brain and, due to its enhanced concentration level in the brain, displays also enhanced efficacy in interaction with the target molecules located in the brain. Taken together, these properties make the administration of galantamine as a R1-prodrug a preferred medication in the diseases mentioned above.

Pharmaceutical Compositions and Administration

Acids useful for preparing the pharmaceutically acceptable acid addition salts according to the invention include inorganic acids and organic acids, such as sulfamic, amidosulfonic, 1,2-ethanedisulfonic, 2-ethylsuccinic, 2-hydroxyethanesulfonic, 3-hydroxynaphthoic, acetic, benzoic, benzenesulfonic acid, carboxylic, ethylenediamine tetraacetic acid, camphorsulfonic, citric, dodecylsulfonic, ethanesulfonic, ethenesulfonic, ethylenediamine tetraacetic, fumaric, glubionic, glucoheptonic, gluconic, glutamic, hexylresorcinic, hydrobromic, hydrochloric, isethionoc, (bi)carbonic, tartaric, hydriodic, lactic, lactobionic, laevulinic, laurylsulfuric, lipoic, malic, maleic, malonic, mandelic, methanesulfonic, mucic, naphthalenesulfonic, nitric, oxalic, pamoic, pantothenic, perchloric, phosphoric, polygalacturonic, pectic, propionic, salicylic, succinic or sulfuric acid, p-tuluenesulfonic, wherein hydrochloric, hydrobromic, sulfuric, nitric, phosphoric and perchloric acids, as well as tartaric, citric, acetic, succinic, maleic, fumaric and oxalic acids are preferred.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 0.1-50 milligrams of active compound.

The tablets, pills, capsules, troches and the like may also contain the following ingredients: a binder such as microcrystalline cellulose, gum tragacanth or gelatin: an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavouring agent such as peppermint, methyl salicylate, or orange flavouring. When the dosage unit form is a capsule, it may contain, in addition to materials of the above-type, a liquid carrier such as an oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colourings and flavours. Materials used in preparing these various compositions should be pharmaceutically pure and nontoxic in the amounts used.

For the purpose of nasal or parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a nasal or parenteral dosage unit contains between 0.1 to 20 milligrams of active compound.

Further the compounds of the present invention can be administered via intranasal delivery to the cerebral spinal fluid as disclosed in detail in WO2004/02404.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such as ethylene-diamine tetraacetic acid; buffers such as acetates; citrates or phosphates and agents for the adjustment of tonicity such as sodium chloride or dextrose. Parenteral multiple dose vials may be of glass or plastic.

Typical dosage rates in administration of the active ingredients depend on the nature of the compound that is used and in intravenous administration are in the range of 0.01 to 2.0 mg per day and per kilogram of body weight based on the physical condition and other medications of the patient.

The following specific formulations exemplify suitable applications: Tablets and capsules that contain 0.5 to 50 mg. Solution for parenteral administration that contains 0.1 to 30 mg of active ingredient/ml. Liquid formulations for oral administration at a concentration of 0.1 to 15 mg/ml. Liquid formulations for nasal or intra-cerebroventricular administration at a concentration of 0.1 to 5 mg of active ingredient/ml. The compounds according to the invention can also be administered by a transdermal system, in which 0.1 to 10 mg/day is released. A transdermal dosage system may consists of a storage layer that contains 0.1 to 30 mg of the active substance as a free base or salt, in case together with a penetration accelerator, e.g., dimethyl sulfoxide, or a carboxylic acid, e.g., octanoic acid, and a realistic-looking polyacrylate, e.g., hexylacrylate/vinyl acetate/acrylic acid copolymer including softeners, e.g., isopropylmyristate. As a covering, an active ingredient-impermeable outside layer, e.g., a metal-coated, siliconised polyethylene patch with a thickness of, for example, 0.35 mm, can be used. To produce an adhesive layer, e.g., a dimethylamino-methacrylate/methacrylate copolymer in an organic solvent can be used.

The invention also relates to pharmaceutical compositions that in a pharmaceutically acceptable adjuvant contain a therapeutically effective amount of at least one of the compounds that are proposed according to the invention.

Examples of chemical synthesis and properties of derivatives are given in the following examples. Abbreviations: DCM: dichloromethane; DMAP: 4-dimethylaminopyridine; DCC: dicyclohexylcarbodiimide; DCHU: dicyclohexylurea.

Example 1

N-Methoxymethyl-galanthaminiumchloride (=(4aS, 6R,8aS)-4a,5,9,10,11,12-Hexahydro-11-methoxymethyl-11-methyl-6H-6-hydroxy-3-methoxy-benzofuro[3a,3,2-ef][2]benzaze-pinium, chloride)

N-Methoxymethyl-galanthaminiumchloride is obtained from Galantamine via alkylation using chloromethylmethylether:

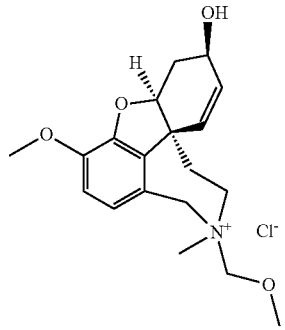

To a solution of (−)-Galantamine (5.00 g, 17.4 mmol) in dry dimethylformamide (12 mL) chloromethylmethylether (1.12 g, 13.9 mmol) is added at −5 bis 0° C. in the course of 15 min and stirred for 4 hrs. at room temperature. The reaction mixture is poured on ethyl acetatet (500 mL) and the precipitate obtained is filtered and washed using ethyl acetate (3×50 mL).

The crude product (4.20 g, 82%) has a purity of 96% (HPLC). For further purification the crude product is dissolved in dry ethanol, stirred after the addition of activated charcoal, filtered and added to ethyl acetate (500 mL). The precipitate is filtered and washed using ethyl acetate (3×50 mL) and dry diethylether (1×50 mL). The product is obtained in the form of colourless crystals (3.85 g, 75% d. Th.) melting at 126-127° C.

Opt. Rotation: $[\alpha]_D^{20}$=−113.9° (c=0.18 g/water) calcd. For $C_{19}H_{26}ClNO_4*0.33H_2O$ C, 61.04; H, 7.19; N, 3.75. found: C, 61.10; H, 7.07; N, 3.75.

$^1$H NMR (DMSO-d6) δ 6.86 (s, 2H), 6.29 (d, J=10 Hz, 1H), 5.88 (d, J=10 Hz, J=4 Hz, 1H), 5.13 (bs, 3H), 4.66 (s, 2H), 4.48 (d, J=14 Hz, 1H), 4.22-3.90 (m, 2H), 3.81 (s, 3H), 3.70 (s, 3H), 3.70-3.52 (m, 1H), 2.75 (s, 3H), 2.44-1.79 (m, 4H); 13C NMR (DMSO-d6) δ 146.4 (s), 145.2 (s), 132.8 (s), 130.2 (d), 125.3 (d), 123.7 (d), 117.8 (s), 112.1 (d), 94.8 (t), 86.4 (d), 61.7 (d), 60.3 (t), 59.4 (q), 56.2 (t), 55.6 (q), 46.2 (s), 40.2 (q), 31.1 (2 t);

The chemical and biological stability of this compound has been determined in various buffers (chemical stability), in rat blood serum, and in rat brain extract, suggesting that the derivative can act as a pro-drug.

Instead of chloromethyl or methyl ether the following reagents can be used alternatively: Methoxymethanolbenzenesulfonate, trifluoromethanesulfonic acid methoxymethyl ester, or methoxymethanol 4-methylbenzenesulfonate.

Example 2

Tert-Butoxycarbonylamino-acetic acid (N-norgalanthaminyl)-methyl ester

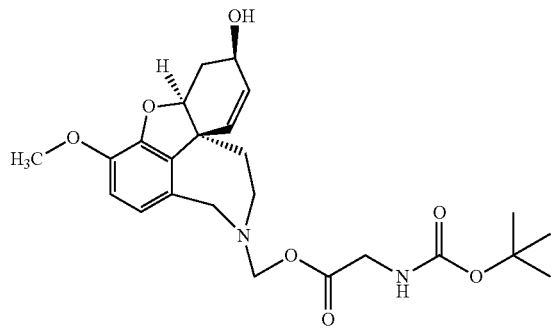

To a solution of N-Boc-glycine chloromethylester (1.0 mmol) and norgalantamine (1.0 mmol) in dry DMF (2.0 mL) triethylamine (3 mmol) was added dropwise and the reaction stirred under nitrogen for 3 days. The triethylammonium chloride formed was filtered and washed with dry ether and the filtrate rotoevaporated to dryness. The residue was redissolved in dry acetone (2 ml) upon heating and left to stand overnight at 4° C. for additional precipitation of the triethylammonium salt. After renewed filtration and rotoevaporation the mixture was chromatographed on silica using ethyl acetate/petrol ether. The target product was isolated as an oil.

$^{13}$H NMR (DMSO-d6) δ 28.5, 33.9, 37.9, 42.0, 48.2, 51.2, 56.2, 56.9, 61.9, 79.5, 79.9, 88.8, 111.8, 121.3, 126.6, 129.8, 130.8, 133.6, 145.8, 148.2, 156.3, 169.6.

Example 3

2-tert-Butoxycarbonylamino-3-phenylpropionic acetic acid (N-norgalantha-minyl)-methyl ester

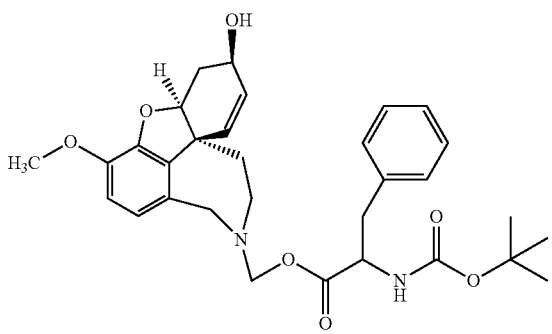

This compound was prepared using the procedure of example 2 with N-Boc-phenylalanine chloromethylester.

$^{13}$H NMR (DMSO-d6) δ 28.5, 33.9, 36.9, 37.9, 48.2, 51.2, 54.6, 56.2, 56.9, 61.9, 79.5, 80.2, 88.8, 111.8, 121.3, 126.0, 126.6, 127.8, 128.7, 129.8, 130.8, 133.6, 139.5, 145.8, 148.2, 156.0, 171.6.

Example 4

(3R,4aS,9bS)-9-Dimethylaminomethyl-6-methoxy-3,4,4a,9b-tetrahydro-9b-vinyl-dibenzofuran-3-ol; (=10,11-Seco-11,12-dehydro-10-methyl-galantamine)

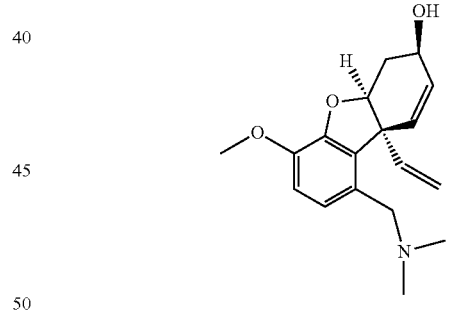

A solution of N-methylgalanthaminium iodide (5.0 g, 11.6 mmol) in 35% aqueous potassium hydroxide (150 mL) is heated under reflux for 48 hrs, diluted with water (200 mL) and acidified using conc. hydrochloric acid to pH=3-4 and extracted with dichloromethane (2×50 mL) to remove non-basic compounds. The aqueous phase is basified using conc. ammonia to pH 12 and extracted using dichloromethane (4×100 mL). The combined organic extracts are washed with brine (2×50 mL), dried using sodium sulfate and rotoevaporated to obtain the crude product which is purified by MPLC (200 g $SiO_2$, chloroform:methanol=99:1+1% conc. ammonia). The product is obtained as yellow oil (2.5 g, 71% d. Th.). The fumarate (colourless crystals) and oxalate salt (off-white crystals) where obtained in the usual way: m.p.: 151-153° C. (fumarate), 116-118° C. (oxalate). $[\alpha]_D^{20}$=−56.5° (0.212 g/100 mL $H_2O$) (fumarate).

| fumarate: | oxalate |
|---|---|
| $C_{18}H_{25}NO_3 * 1.0C_4H_4O_4$ | $C_{18}H_{25}NO_3 * 1.0C_2H_2O_4 * 0.75H_2O$ |
| Calcd.: C, 62.99; H, 6.97; N, 3.34 | Calcd.: C, 59.32; H, 6.60; N, 3.46 |
| Found: C, 62.89; H, 6.62; N, 3.32 | Found: C, 59.48; H, 6.31; N, 3.38 |

$^1$H-NMR (CDCl3): δ 6.83 (d, J=8.4 Hz, 1H), 6.72 (d, J=8.4 Hz, 1H), 6.13-5.95 (m, 3H), 5.32 (dd, J=10.3, 1.1 Hz, 1H), 5.25 (dd, J=18.3, 1.1 Hz), 4.63 (b, 1H), 4.15 (b, 1H), 3.85 (s, 3H), 3.58 (d, J=12.8 Hz, 1H), 3.07 (d, J=12.8 Hz, 1H), 2.56 (m, 1H), 2.15 (s, 6H), 1.96 (ddd, J=16.2, 4.9, 2.3 Hz, 1H); $^{13}$C-NMR (CDCl3): δ 146.6 (s), 144.1 (s), 139.0 (t), 132.2 (s), 128.6 (s), 128.1 (d), 127.8 (d), 123.6 (d), 117.3 (t), 111.1 (d), 86.0 (d), 62.0 (t), 59.7 (t), 55.7 (q), 52.9 (s), 44.7 (q), 28.6 (t)

Example 5

(3R,4aS,9bS)-6-Methoxy-9-methylaminomethyl-3,4,4a,9b-tetrahydro-9b-vinyl-dibenzofuran-3-ol; (=10,11-Seco-11,12-dehydro-galantamine)

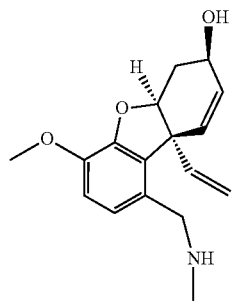 [SMILES: C=C[C@@]12C=C[C@H](O)C[C@@H]1Oc1c(OC)ccc(CNC)c12]

3-Chloroperbenzoic acid (0.38 g, 75% ig, 1.66 mmol) is added to a solution of (3R,4aS,9bS)-9-dimethylaminomethyl-6-methoxy-3,4,4a,9b-tetrahydro-9b-vinyl-dibenzofuran-3-ol (0.50 g, 1.66 mmol) in dichloromethane (35 mL) and then stirred for 30 minutes at room temperature. After adding a solution of iron(II)sulfate-heptahydrate (0.23 g, 0.83 mmol) in methanol (5 mL) it is then stirred for another 20 minutes at room temperature. Then 2N hydrochloric acid (30 mL) is added, stirred for 5 minutes and most of the dichloromethane is removed by rotoevaporation. The remaining aqueous phase is washed with diethyl ether (4×20 mL), basified to pH 12 using concentrated ammonia and then extracted with dichloromethane (4×40 mL). The combined organic phases are washed with saturated sodium chloride solution (30 mL), dried using sodium sulphate, filtered and the solvent is again removed by rotoevaporation to obtain the crude product which is then further purified using MPLC (Büchi, 110 g SiO$_2$, chloroform:methanol 97:3+1% concentrated ammonia) and obtained as a yellow oil (0.30 g, 63% d. Th.). The oxalate is prepared in the usual way and obtained as colourless crystals, 0.37 g, 59% d. Th., m.p. 127-129°. The purity is checked by TLC (chloroform:methanol=9:1+1% conc. ammonia, Rf=0.35). $[α]_D^{20}$= -41.8° (0.220 g/100 mL H$_2$O) (Oxalate)

$C_{17}H_{21}NO_3*1.0C_2H_2O_4*0.5H_2O$
Calcd.: C, 59.06; H, 6.26; N, 3.62.
Found: C, 59.35; H, 6.00; N, 3.56.

$^1$H-NMR (CDCl3): δ 6.88 (d, J=8.4 Hz, 1H), 6.75 (d, J=8.4 Hz, 1H), 6.15-5.82 (m, 3H), 4.67 (b, 1H), 4.09-4.20 (m, 1H), 3.85 (s, 3H), 3.68 (s, 2H), 2.52-2.49 (m, 1H), 2.42 (s, 3H), 1.97 (ddd, J=16.2, 4.9, 2.3 Hz, 1H); 13C-NMR (CDCl3): δ 146.6 (s), 144.0 (s), 139.4 (d), 131.6 (s), 129.5 (s), 128.9 (d), 127.2 (d), 122.7 (d), 117.6 (t), 111.8 (d), 86.0 (d), 62.0 (d), 55.9 (q), 52.8 (t), 51.1 (s), 36.0 (q), 28.8 (t)

Example 6

(3R,4aS,9bS)-9-Dimethylaminomethyl-9b-ethyl-6-methoxy-3,4,4a,9b-tetrahydro-dibenzofuran-3-ol; (=10,11-Seco-10-methyl-galantamine)

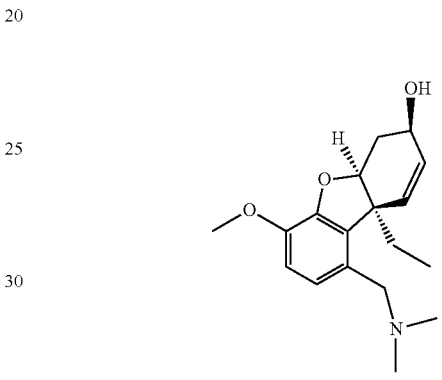

Palladium (10%) on active carbon (90 mg) is pre-hydrogenated in methanol (40 mL) and conc. acetic acid (2 mL) in the Parr-apparatus at 10 psi and room temperature for 45 minutes. After adding (3R,4aS,9bS)-9-dimethylaminomethyl-6-methoxy-3,4,4a,9b-tetrahydro-9b-vinyl-dibenzofuran-3-ol (0.90 g, 2.99 mmol) it is then hydrated for 8 hrs. at 15-20 psi and room temperature. The catalyst is then filtered and the solvent is removed by rotoevaporation. The residue is then dissolved in water (100 mL), basified using conc. ammonia and extracted using dichloromethane (5×40 mL). The combined aqueous phases are washed with a saturated sodium chloride solution (2×20 mL), dried using sodium sulphate and the solvent is removed by rotoevaporation. It is then further purified using MPLC (Büchi, 110 g SiO$_2$, chloroform:methanol=98:2+1% conc. ammonia), obtained as a colourless oil (0.80 g, 88%) and converted to the hydrochloride m.p. 248-249°. $[α]_D^{20}$=−47.3° (0.220 g/100 mL H$_2$O). TLC chloroform:methanol=9:1+1% conc. ammonia, Rf=0.45.

$C_{18}H_{25}NO_3*2.0$ HCl
Calcd.: C, 57.45; H, 7.23; N, 3.72.
Found: C, 57.95; H, 6.85; N, 3.48.

$^1$H-NMR (CDCl3): δ 6.78 (d, J=8.3 Hz, 1H), 6.67 (d, J=8.3 Hz, 1H), 6.12 (d, J=10.2 Hz, 1H), 5.89 (dd, J=10.2, 4.3 Hz, 1H), 4.74 (b, 1H), 4.19-4.09 (m, 1H), 3.84 (s, 3H), 3.54 (d, J=12.9 Hz, 1H), 3.19 (d, J=12.9 Hz, 1H), 2.53-2.32 (m, 1H), 1.94-2.13 (m, 2H), 1.69 (ddd, J=16.2, 4.9, 2.3 Hz, 1H), 0.85 (t, J=7.6 Hz, 3H); $^{13}$C-NMR (CDCl3): δ 146.8 (s), 144.4 (s), 131.6 (d), 128.2 (s), 127.7 (d), 123.6 (d), 110.6 (d), 83.8 (d), 62.7 (d), 61.6 (s), 55.7 (q), 51.1 (s), 45.2 (q), 31.6 (t), 27.5 (t),

Example 7

3.3.4. (3R,4aS,9bS)-9b-Ethyl-9-methylaminomethyl-6-methoxy-3,4,4a,9b-tetrahydro-dibenzofuran-3-ol; (=10,11-Seco-galantamine)

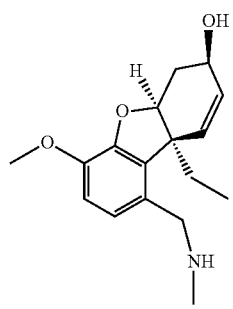 [SMILES: CC[C@@]12C=C[C@H](O)C[C@@H]1Oc1c(OC)ccc(CNC)c12]

Following the procedure of example 6 using (3R,4aS,9bS)-9-Dimethylaminomethyl-9b-ethyl-6-methoxy-3,4,4a,9b-tetrahydro-dibenzofuran-3-ol the pure product is obtained as a yellow oil (0.17 g, 59% d. Th.) and converted to the oxalate and fumarate.

M.p. (oxalate) 162-164°, $[\alpha]_D^{20}$=−51.2° (0.146 g/100 mL H$_2$O) (oxalate).

TLC chloroform:Methanol=9:1+1% conc. ammonia, Rf=0.39

| fumarate: | oxalate |
|---|---|
| C$_{17}$H$_{23}$NO$_3$ * 1C$_4$H$_4$O$_4$ * 0.33H$_2$O | C$_{17}$H$_{23}$NO$_3$ * 1C$_2$H$_2$O$_4$ * 0.25H$_2$O |
| Calcd.: C, 61.31; H, 6.78; N, 3.40 | Calcd.: C, 59.44; H, 6.69; N, 3.65 |
| Found: C, 61.22; H, 6.67; N, 3.22 | Found: C, 59.53; H, 6.78; N, 3.65 |

$^1$H-NMR (CDCl3): δ 6.85 (d, J=8.4 Hz, 1H), 6.73 (d, J=8.4 Hz, 1H), 5.97-5.92 (m, 2H), 4.74 (dd, J=5.8, 3.5 Hz, 1H), 4.22-4.12 (m, 1H), 3.84 (s, 3H), 3.74 (d, J=7.2 Hz, 2H), 2.48 (s, 3H), 2.45-2.28 (m, 2H), 2.20-1.62 (m, 5H), 0.85 (t, J=7.46, 3H); $^{13}$C-NMR (CDCl3): δ 146.6 (s), 144.2 (s), 131.1 (s), 131.0 (d), 128.9 (s), 128.8 (d), 122.3 (d), 111.1 (d), 83.8 (d), 62.8 (d), 55.8 (q), 51.0 (s), 36.3 (q), 32.5 (t), 29.1 (t),

Example 8

(4aS,6R,8as)-4a,5,9,10,11,12-Hexahydro-3-methoxy-11-methyl-6H-benzofuro[3a,3,2-ef][2]benzazepin-6-yl-β-D-glucopyranosiduronic acid (=Galantamine-3-glucuronide)

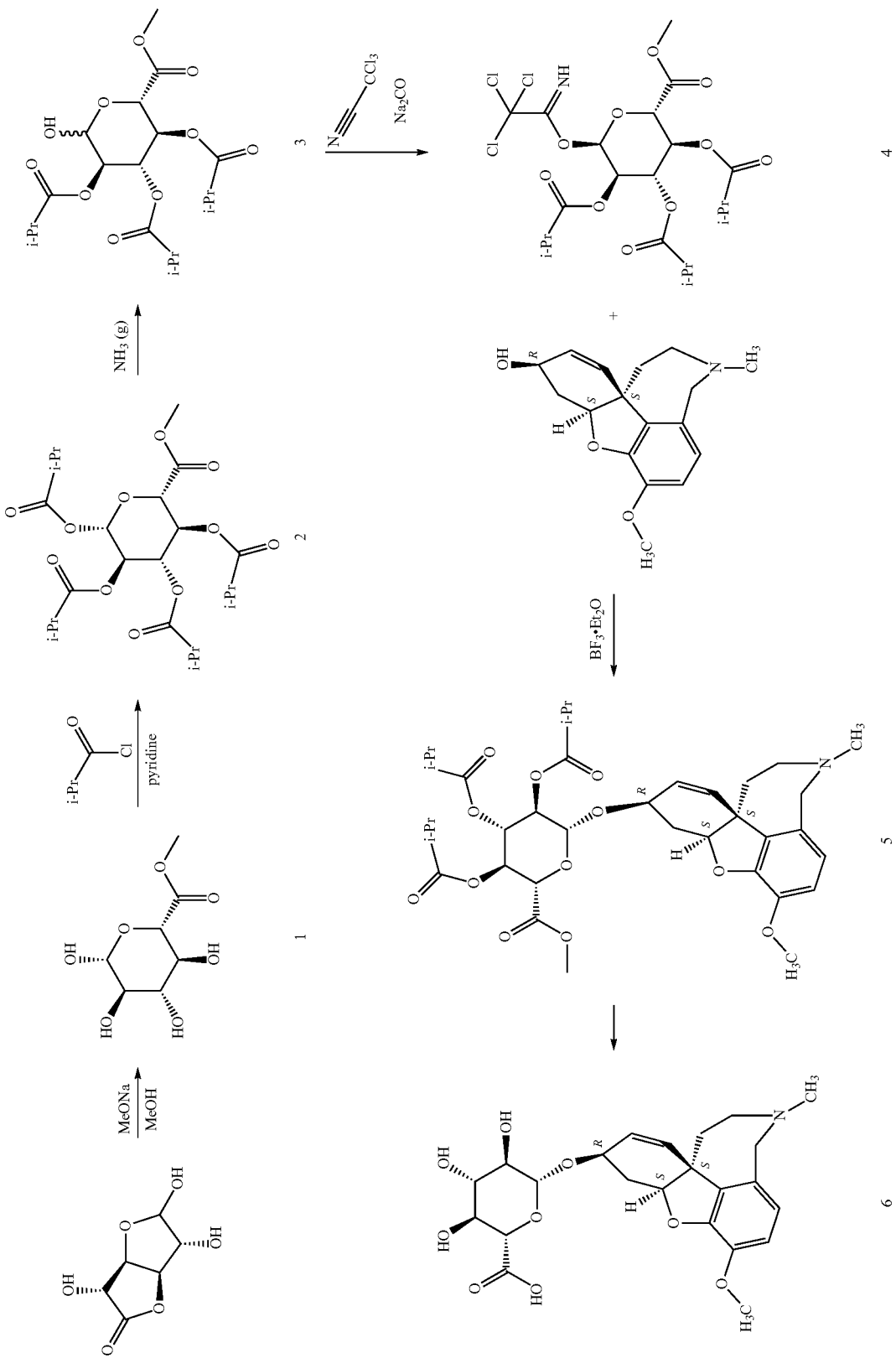

Step 1: Methyl 1,2,3,4-tetra-O-isobutyryl-β-D-glucopyranuronate (2)

To a solution of NaOMe (26 mg, 0.48 mmol) in MeOH (150 mL) was added glucurono-6,3-lactone (20.6 g, 154 mmol) in portions with stirring until dissolved. The solvent was then removed in vacuo, the residue taken up in pyridine (85 mL, 1.08 mol) and the solution cooled to 0° C. Isobutyryl chloride (110 mL, 1.06 mol) in CH$_2$Cl$_2$ (70 mL) was then added with strong mechanical stirring at a rate that kept the temperature below 10° C., and the reaction mixture was left at room temperature overnight. More CH$_2$Cl$_2$ (100 mL) was then added and the solution washed with water (400 mL), 2 M HCl (3×50 mL), saturated sodium bicarbonate (5×50 mL) and brine (50 mL). After drying, filtering and evaporating in vacuo, a gum was obtained which crystallized on trituration with petroleum ether (40-60° C.). Filtration and drying at 40° C. in a vacuum oven yielded the title product. Recrystallisation from MeOH or petrol ether afforded the pure β isomer 2 as needles, mp 127° C., (21.6 g, 37%, from mother liquid some more product could be isolated) [α]$_D$=+11.12 (c 1.7 CHCl3); δ$_H$ (300 MHz, CDCl3): 5.78 (d, J=8 Hz), 5.39 (t, J=9.5 Hz), 5.25 (t, J=9.5 Hz), 5.23 (dd, J=9.5, 8 Hz), 4.19 (d, J=9.5 Hz),3.75 (s, OMe), 2.65-2.45 (m, 4×CHMe$_2$), 1.17-1.07 (m, 4×CHMe$_2$).

An alternative procedure with pivaloyl chloride was also used to prepare methyl 1,2,3,4-tetra-O-pivaloyl-β-D-glucopyranuronate in 21% (the isolation and crystallization of compound 2 was easier).

Step 2: Methyl 2,3,4-tri-O-isobutyryl-D-glucopyranuronate (3)

Ammonia gas pre-dried by passing it through a bed of sodium hydroxide was bubbled through CH$_2$Cl$_2$ (200 mL) at −4° C. over 1 h at a rate which kept the temperature below 0° C. The above methyl 1,2,3,4-tetra-O-isobutyryl-β-D-glucopyranuronate (3.0 g, 8 mmol) was added and the solution stirred at 0° C. for 3 h and then left at room temperature for 20 h. Nitrogen gas was bubbled through the solution for 30 min. and it was extracted with ice-cold 10% aqueous HCl, then water. The organic phase was dried over Na$_2$SO$_4$ filtered and solvent removed in vacuo to leave the crude product. Recrystallization from CHCl$_3$:PE afforded the pure microcrystalline α-epimer, mp 89° C. δH (300 MHz, CDCl3): 5.65 (t, J=10 Hz), 5.54 (d, J=3.5 Hz), 4.92 (dd, J=10, 3.5 Hz), 4.60 (d, J=10 Hz), 3.75 (s, OMe), 2.61-2.43 (m, 4×CHMe$_2$), 1.20-1.05 (m, 4×CHMe$_2$).

Step 3: Methyl 2,3,4-tri-O-isobutyryl-1-O-trichloroacetimidoyl-α-D-glucopyranuronate (4)

To a stirred solution of methyl 2,3,4-tri-O-isobutyryl-D-glucopyranuronate 3 (418 g, 1 mmol) in CH$_2$Cl$_2$ (5 mL) was added trichloroacetonitrile (0.4 mL, 3.7 mmol), followed by anhydrous potassium carbonate (83 mg, 0.6 mmol), and the mixture stirred for 40 h. It was filtered through a short pad of silica and eluted with ether. Filtration and evaporation in vacuo then yielded the title product 4 as a semi crystalline gum which crystallized from dry isopropanol as white prisms, mp 108° C. (422 mg, 75%). δH (300 MHz, CDCl3): 8.72 (s, NH), 6.66 (d, J=3.5 Hz), 5.70 (t, J=10 Hz), 5.30 70 (t, J=10 Hz), 5.20 (dd, J=10, 3.5 Hz), 4.51 (d, J=10 Hz), 3.75 (s, OMe), 2.60-2.43 (m, 3×CHMe$_2$), 1.17-1.06 (m, 3×CHMe$_2$).

Step 4: Galantamine-6-methyl 2,3,4-tri-O-isobutyryl-β-D-glucopyranuronate (5)

A suspension of dried galantamine hydrobromide (92 mg, 0.25 mmol) and the above methyl 2,3,4-tri-O-isobutyryl-1-O-trichloroacetimidoyl-β-D-glucopyranuronate 4 (282 mg, 0.5 mmol) in dry CH$_2$Cl$_2$ (10 mL) containing 4 Å molecular sieves was stirred under argon at room temperature, while BF$_3$.Et$_2$O (0.1 mL, 0.5 mmol) was added. After 1 h, virtually all of the starting materials had dissolved and stirring was continued for 2 days. More CH$_2$Cl$_2$ (20 mL) was added, the solution washed with saturated aq. sodium bicarbonate (10 mL), water and brine before being dried. Filtration and evaporation in vacuo afforded a semisolid residue, which was purified with MPLC on silica. Elution with CHCl$_3$/MeOH 97:3-20 gave 75 mg of the glucuronide. Trituration with EtOH yielded 30 mg of pure 5.

Step 5: (4aS,6R,8aS)-4a,5,9,10,11,12-Hexahydro-3-methoxy-11-methyl-6H-benzofuro[3a,3,2-ef][2]benzazepin-6-yl-β-D-glucopyranosiduronic acid (Galantamine-3-glucuronide) (6)

2M-NaOH (2.0 mL) was added to a stirred suspension of the glucuronate 5 (30 mg) in MeOH (4 mL), and the mixture left overnight. The solution was then acidified with glacial acetic acid to pH 5.5, the solvent evaporated and purified over silica with CHCl$_3$: MeOH (saturated with dry NH$_3$) 95:5. The product-fraction was freeze-dried to afford 14 mg of 6 as a white powder, m.p. 238° (dec.).

$^1$H NMR (MeOD, 200 MHz): 1.63-1.73 (m, 1H), 2.02-2.21 (m, 2H), 2.38 (s, 3H), 2.43-2.53 (m, 1H), 2.99-3.06 (m, 1H), 3.19-3.33 (m, 1H), 3.47-3.49 (m, 1H), 3.65-3.71 (d, 1H, J=14.9 Hz), 3.78 (s, 3H), 4.05-4.13 (d, 1H, J=14.9 Hz), 4.58 (m, 1H), 5.85-5.94 (dd, 1H, J2=4.8 Hz, J2=10.2 Hz), 6.15-6.21 (d, 1H, J2=10.2 Hz), 6.63-6.77 (m, 2H)

$^{13}$C NMR (MeOD, 200 MHz): 23.22, 28.65, 34.57, 42.02, 43.33, 48.09, 54.03, 55.64, 60.43, 88.54, 112.18, 122.30, 127.16, 127.70, 128.64, 133.49, 144.65, 146.39

Example 9

Galantamine-3,6-di-β-D-glucuronide

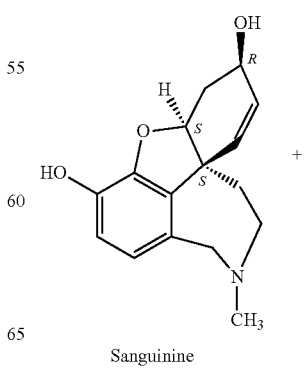

Sanguinine

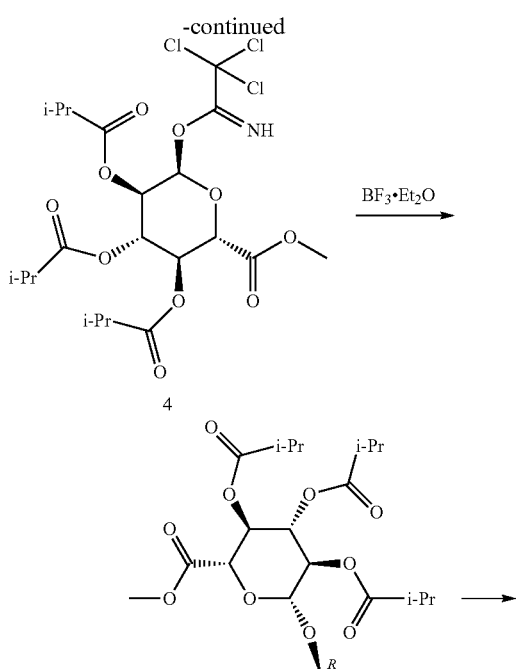

4

7

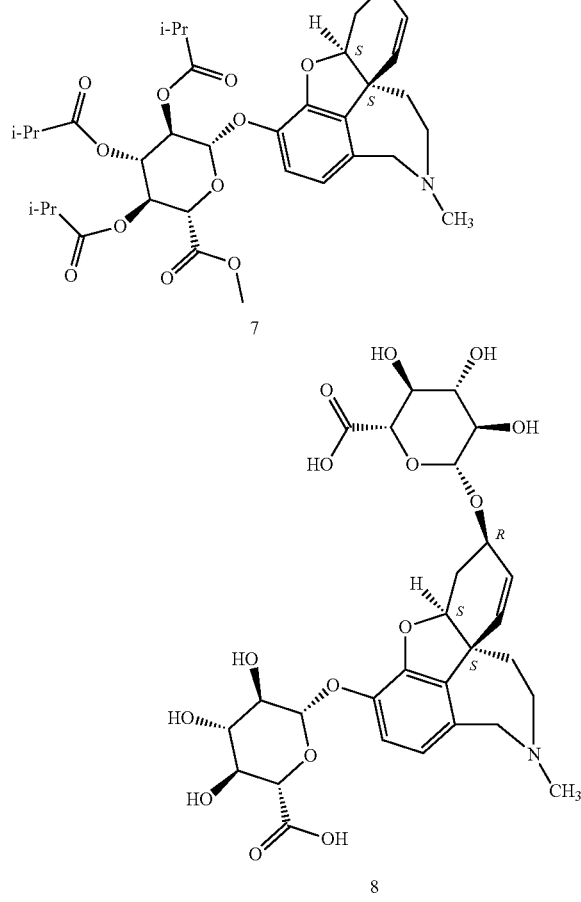

8

Step 1: Galantamine-3,6-di(methyl 2,3,4-tri-O-isobutyryl-3-D-glucopyranuronate) (7)

Following the procedure for the preparation of Galantamine-6-methyl 2,3,4-tri-O-isobutyryl-β-D-glucopyranuro-nate but using sanguinine (137 mg, 0.5 mmol) and the above imidate 4 (1.12 g, 2 mmol) in dry $CH_2Cl_2$ (10 mL) afforded, after analogous workup a semisolid residue, that was purified with MPLC on silica. Elution with $CHCl_3$/MeOH 97:3-20 gave the crude product (180 mg). Trituration with EtOH yielded 130 mg of the pure product 7.

Step 2: Galantamine-3,6-β-D-diglucuronide (8)

2M-NaOH (2.0 mL) was added to a stirred suspension of the above glucuronate 7 (130 mg) in MeOH (4 mL), and the mixture left overnight. The solution was then acidified with glacial acetic acid to pH 5.5, the solvents removed by freeze drying and the product chromatographed on silica using $CHCl_3$: MeOH (saturated with dry $NH_3$) 95:5. gave 48 mg (63.5%) of the product 8.

$^1$H NMR (CDCl3, 200 MHz): 1.60-1.72 (m, 2H), 1.82-2.6 (m, 10H), 2.88-3.30 (m, 3H), 3.50-3.67 (m, 6H), 3.80-4.20 (m, 3H), 4.30-4.70 (m, 1H), 4.94-5.30 (m, 6H), 5.76-6.21 (m, 2H), 6.42-6.56 (m, 1H), 6.74-6.86 (m, 1H)

Example 10

3-Nicotinoyl-galantamine

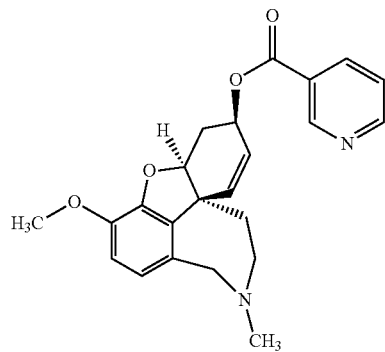

A solution of galantamine (431 mg, 1.5 mmol) in dry pyridine (25 mL) was treated with nicotinoyl chloride (240 mg, 1.7 mmol) and 4-N,N-dimethylaminepyridine (5 mg) at 0° and the solution stirred to room temp. for 2 hrs. followed by heating to 450 for 1 hr. The reaction mixture was poured on water (150 mL) and the pH adjusted to 8.0 followed by extraction with dichloromethane. The organic extract was washed with water and brine, dried (sodium sulphate) and evaporated to give the crude product (480 mg, 81.5%)

$^{13}$H NMR (DMSO-d6) δ 27.7, 34.3, 41.7, 47.8, 53.6, 55.9, 60.3, 63.2, 86.2, 111.5, 121.3, 122.1, 122.7, 126.0, 129.2, 130.6, 131.9, 136.4, 143.9, 146.5, 150.4, 151.5, 166.0.

This product was converted to the dihydrobromide salt by dissolution in a minimum amount of warm 40% hydrobromic acid followed by cooling and obtained as colorless crystals.

Anal. calcd. for $C_{23}H_{24}N_2O_4 \cdot 2HBr \cdot 0.33H_2O$ C, 49.31; H, 4.80; N, 5.00. Found C, 49.10; H, 5.05; N, 4.85.

Example 11
(+−)-8-fluorogalantamine
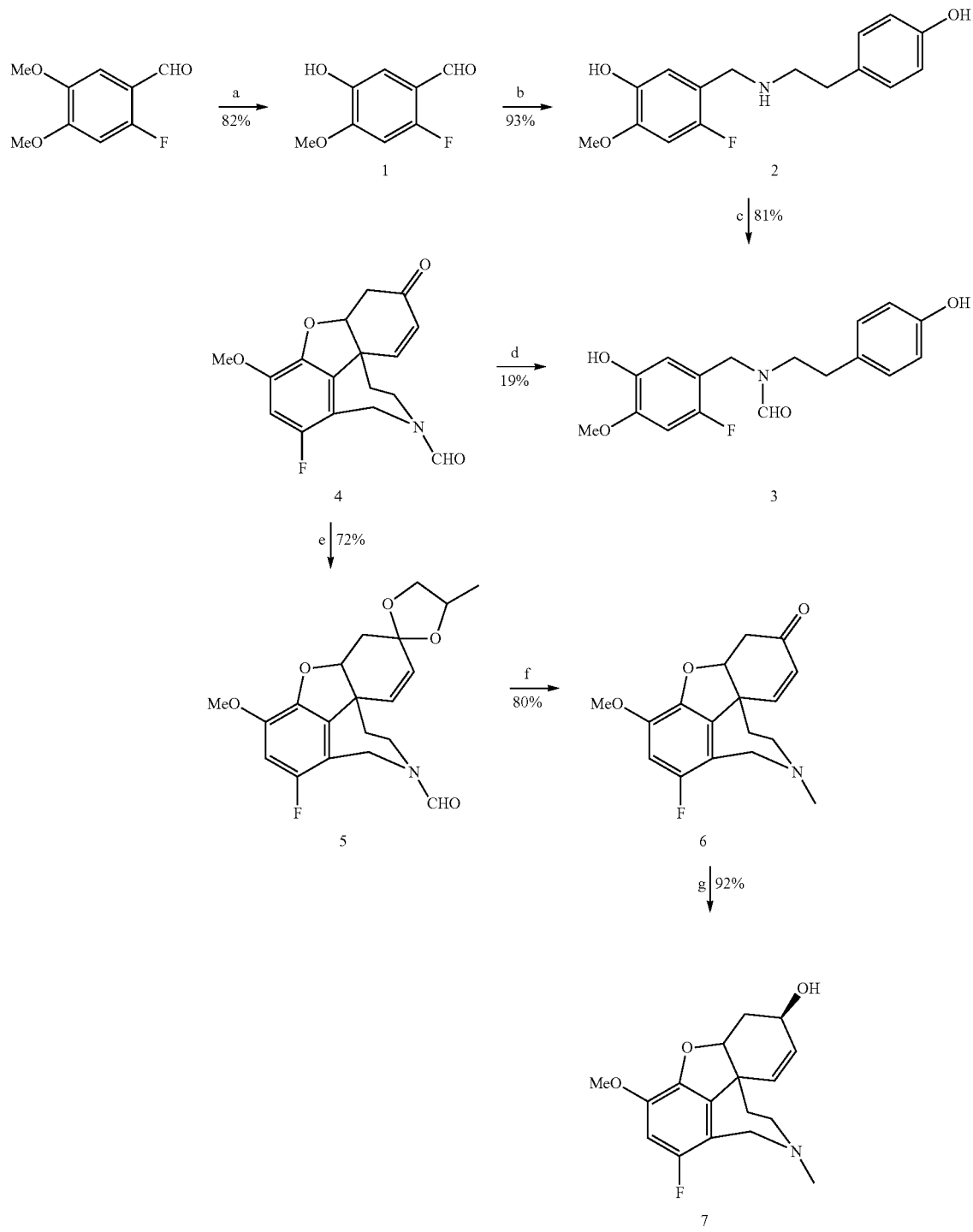
a H₂SO₄, 90° C.
b 1. 4-hydroxy-phenylethyl amine, toluol/n-buthanol, reflux 2. methanol, NaBH₄
c ethylformiat, formic acide, DMF, dioxan, reflux
d K₃[Fe(CN)₆], K₂CO₃, toluol/water, 50° C.
e 1,2-propanediol, PTSA, toluene, reflux
f LiAlH₄, THF, 2N HCl
g L-selectride, THF

Step 1: 2-Fluoro-5-hydroxy-4-methoxy benzaldehyde (1)

Sulphuric acid (50 ml, 95-98%) was heated with stirring to the 90-95° C. under a dry nitrogen and 4,5-dimethoxy-2-fluoro benzaldehyde (10.1 g, 54.8 mmol) added quickly and this mixture was stirred at the same temperature for 3.5 h. Reaction was followed by HPLC and found to be complete after this time. The reaction mixture was poured on crushed ice (150 g) and the white slurry obtained was heated to 65° C. and allowed to cool in the fridge overnight. The white precipitate was filtered and washed with water (2×100 ml). The wet cake was dried in the desiccator under reduced pressure to afford the product (7.6 g, 82%, HPLC 95%, m.p.: 146-148) as off white crystals.

Step 2: 4-Fluoro-5-{[2-(4-hydroxyphenyl)ethyl-amino]-methyl}-2-methoxy-phenol (2)

A solution of 1 (7.6 g, 45 mmol) and tyramine (6.7 g, 49 mmol) in dry toluene (250 ml) and n-butanol (250 ml) was heated and stirred to reflux for 5 h on the Dean-Stark apparatus to remove the water. Reaction development was controlled by TLC (MeOH:CH$_2$Cl$_2$ 1:9) and reaction was found to be complete after this time. Solvents were roto-evaporated and residue was dissolved in dry methanol (500 ml). NaBH$_4$ (1.8 g, 45 mmol) was added at the temperature 0-5° C. and this mixture was stirred overnight while the temperature was raised to room temperature and a white solid precipitated from the reaction mixture. The solid was filtered and washed with cold methanol (2×50 ml). The white, wet cake was dried in the desiccator at reduced pressure to give the product (9.6 g, 74%, HPLC >99%) as a white powder. The filtrate was rotaevaporated to give a brown slurry (3.6 g), which was chromatographed on silica (dichloromathane/methanol, gradient 0-10%) to give another (2.5 g, 19%, HPLC >99%) of product as a off white powder (total yield 93%, m.p.: 160-162° C.).

$^1$H NMR (MeOD, 200 MHz): 2.69 (s, broad, 4H), 3.66 (s, 2H), 3.80 (s, 3H), 6.66-6.77 (m, 4H), 6.96-7.00 (m, 2H).

Step 3: N-[(2-fluoro-5-hydroxy-4-methoxyphenyl)methyl]-N-[2-(4-hydroxyphenyl)ethyl]-formamide (3)

To a suspension of 2 (7.63 g, 26.1 mmol) in dioxane (50 ml) a solution of ethyl formiate (3.1 ml, 37.7 mmol), DMF (1.5 ml) and formic acid (0.25 ml, 6.62 mmol) was added dropwise and the reaction mixture was heated under argon to reflux for 10 h. The reaction development was controlled by HPLC and showed complete conversion after this time. Volatiles were removed under reduced pressure, the residue was dissolved in methanol (32 ml) and poured on crushed ice (160 ml), the white precipitate formed was stirred magnetically for 1 h, filtered, washed with water (3×100 ml) and dried to weight to afford the product (6.8 g, 81.3%, HPLC >99%, m.p.: 153-168° C.) as a white powder.

$^1$H NMR (DMSO, 200 MHz): 2.49-2.67 (m, 2H), 3.15-3.29 (m, 2H), 3.75 (s, 3H), 4.28-4.35 (d, 2H, J$_2$=13.89 Hz), 6.64-6.95 (m, 6H), 7.84 (s, 0.5H), 8.20 (s, 0.5H), 8.95-9.00 (d, 1H, 10.17 Hz), 9.18-9.20 (d, 1H, J=2.44 Hz).

Step 4: 4α,5,9,10,11,12-Hexahydro-1-fluoro-3-methoxy-11-formyl-6H-benzofuro[3a,3,2-ef]benzazepine-6-one (4)

To the vigorously stirred biphasic mixture of potassium carbonate (13.2 g, 95.5 mmol) and potassium hexacyanoferrate (28 g, 85.4 mmol) in toluene (580 ml) and water (120 ml), preheated to 50° C., finely pulverized 3 (6.83 g, 21.4 mmol) was added in one portion and this suspension was heated at 50-60° C. with intense stirring for 1 h. After this time the reaction mixture was filtered trough the pad of celite, the toluene phase separated and the water phase was extracted with toluene (2×100 ml). The combined organic phases were dried (Na$_2$SO$_4$) and roto-evaporated under reduced pressure to afford the product (1.3 g, 19%, HPLC 98%) as a white powder.

$^1$H NMR (DMSO, 200 MHz): 1.75-1.93 (m, 1H), 2.15-2.30 (m, 1H), 2.73-2.83 (m, 1H), 3.00-3.12 (m, 1H), 3.40 (s, 4H), 3.98-4.13 (m, 1H), 4.28-4.35 (m, 0.5H), 4.51-4.97 (m, 2H), 5.27-5.34 (d, 0.5H, J=15.45 Hz), 5.94-6.00 (d, 1H, J=10.37 Hz), 6.77-6.86 (m, 1H), 7.15-7.26 (m, 1H), 8.10-8.15 (d, 1H, J=8.99 Hz)

$^{13}$C NMR (DMSO, 200 MHz): 34.02, 37.21, 37.32, 45.45, 49.33, 49.53, 56.05, 87.29, 100.20, 100.34, 100.77, 100.90, 114.55, 114.93, 115.08, 126.66, 130.83, 130.93, 143.12, 143.43, 143.64, 143.76, 144.29, 144.52, 162.39, 162.62, 194.77.

Step 5: 1-Bromo-4a,5,9,10-tetrahydro-3-methoxy-spiro[6H-benzofuro[3a,3,2-ef][2]benzazepine-6,2'-[1,3]dioxolane]-11(12H)-carboxaldehyde (5)

To the solution of 4 (1.084 g, 3.42 mmol) in toluene (10 ml) a solution of 4-toluene sulphonic acid (0.02 g, 0.116 mmol) in 1,2-propane-diol (1.13 ml) was added and the mixture heated to the reflux for 1 h while the water was removed using a Dean-Stark apparatus. Another portion of 4-toluene sulphonic acid (0.05 g) in 1,2-propanediol (0.65 ml) was added and heating continued for another 5 h. Reaction development was controlled by HPLC and the reaction found to be complete after this time. The reaction mixture was cooled to room temperature and extracted with acetic acid (2×25 ml, 10% in water), sodium hydrogen carbonate (2×25 ml, 10% in water) and brine (1×25 ml). The toluene solution was dried (Na$_2$SO$_4$) and evaporated to give a crude product (1.32 g) as an amber oil. This was crystallized using i-propanol and ligroin to give product (0.92 g, 72%), as a colourless crystals.

$^1$H NMR (CDCl$_3$, 200 MHz): 0.74-2.66 (m, 10H), 2.98-4.86 (m, 8H), 5.44-5.74 (m, 1H), 6.34-6.39 (m, 1H), 7.98-8.03 (m, 1H).

(+−)-8-Fluoro-Narwedin (6)

To the solution of 5 (0.91 g, 2.43 mmol) in dry THF (15 ml) lithium aluminium hydride (1.21 ml, 2.3 mol suspension in THF) was added at 0-5° C. under a continuous stream of dry nitrogen and this mixture was stirred for 1 h. Another portion of lithium aluminium hydride (0.605 ml, 2.3 mmol suspension in THF) was added and stirring continued for additional 1 h while the temperature raised slowly to room temperature. Reaction development was controlled by HPLC and no starting material was detected after this time. The reaction mixture was quenched with water/THF 1:1 (20 ml) and volatiles removed under reduced pressure. The residue was dissolved in 2N-hydrochloric acid (25 ml) and stirred at room temperature for 30 min. The clear solution was than treated with ammonia to pH 12 and extracted with ethyl acetate (3×50 ml). The combined organic phases were dried (Na$_2$SO$_4$), treated with charcoal, filtered and evaporated to dryness to give 720 mg of the crude product as an brown oil. Chromatography on silica using 7 N NH$_3$ in MeOH:CH$_2$Cl$_2$ 5:95 as solvents afforded the product (590 mg, yield 80%, HPLC 97%) as an amber oil.

$^1$H NMR (CDCl$_3$, 200 MHz): 1.77-1.84 (m, 1H), 2.09-2.24 (m, 1H), 2.38 (s, 3H), 2.60-2.71 (m, 1H), 2.98-3.11 (m, 3H), 3.64-3.72 (m, 4H), 4.03-4.11 (d, 1H, J=15.65 Hz), 4.65 (s, 1H), 5.93-5.98 (d, 1H, J=10.56 Hz), 6.40-6.46 (d, 1H, J=11.34 Hz), 6.84-6.89 (m, 1H)

$^{13}$C NMR (CDCl$_3$, 200 MHz): 33.41, 37.22, 43.18, 49.42, 49.46, 51.91, 51.99, 54.13, 56.20, 88.12, 99.99, 100.58, 114.98, 115.34, 127.31, 131.33, 131.43, 142.84, 143.51, 143.71, 144.11, 152.42, 157.18, 194.13.

(+−)-8-fluorogalantamine (7)

To the solution of 6 (500 mg, 1.64 mmol) in dry THF (30 ml) L-Selectride (1.50 ml, 1 M solution in THF) was added dropwise at −5 to 0° C. under dry nitrogen and this mixture was stirred at the same temperature for 30 min. The reaction was monitored by HPLC and no starting material was detected after this time. The reaction was quenched using water/THF 2:1 (50 ml) and solvents were removed under reduced pressure. The residue was dissolved in 2N-hydrochloric acid (100 ml) and kept overnight in the fridge. The aqueous solution was than washed with diethyl ether (2×30 ml) and ammonia was added to pH 12. The aqueous phase was extracted using ethyl acetate (3×100 ml), the combined organic phases were washed with brine (50 ml), dried (Na$_2$SO$_4$) and evaporated to afford the crude product (515 mg) as a clear, slightly yellow oil which was purified by chromatography on silica using MeOH:CH$_2$Cl$_2$ 9:1 to afford the product (0.46 g, 92%, HPLC >99%) as a white powder.

$^1$H NMR (CDCl$_3$, 400 MHz): 1.25 (s, 1H), 1.55-1.67 (m, 1H), 1.92-2.10 (m, 2H), 2.41 (s, 4H), 2.62-2.70 (m, 1H), 2.98-3.29 (m, 2H), 3.72-3.78 (d, 1H), 3.81 (s, 3H), 4.07-4.20 (m, 2H), 4.60 (s, 1H), 6.03 (s, 2H), 6.47-6.49 (d, 1H), $^{13}$C NMR (CDCl$_3$, 400 MHz): 30.11 (C-5), 34.31 (C-9), 43.10 (N—CH$_3$), 49.21 (C-8a), 52.15 (C-10), 54.32 (OCH$_3$), 56.55 (C-12), 62.37 (C-6), 89.29 (C-4a), 99.86 (C-2), 100.16 (C-12a), 126.89 (C-12b), 134.25 (C-8), 134.30 (C-7), 142.09 (C-3a), 144.23 (C-3), 154.31 (C-1), 156.69 (C-1).

(−)-8-fluorogalantamine

The enantiomers of (+−)-8-fluorogalantamine were separated using chiral preparative column chromatography (Chiracel OD, 5 μm, 5 □ 50 cm, 80% n-heptane/20% i-PrOH) to afford two isomers which were converted to the corresponding hydrobromide salts. The progress and the result of this chiral separation was analyzed by chiral HPLC (Chiracel I OD-H, 80% n-heptane+0.1% diethyl amine/20% i-PrOH). The crystal structure of (−) 2.HBr was determined thus confirming the expectation, that (−)-8-fluoro¬ga¬lanth¬¬iamine has the same absolute configuration as (−)galantamine.

Example 12

Galantamine, 2-propylpentanoate (ester)

(−)Galantamine (287 mg, 1 mmol), 2-propyl-pentanoic acid (216 mg, 1.5 mmol), 4-dimethylaminopyridine (244 mg, 2 mmoles) are added to dry CH$_2$Cl$_2$ and stirred for 5 min. A solution of dicyclohexylcarbodiimide (DCC, 2 ml of a 1M solution in CH$_2$Cl$_2$) was added in increments and the mixture stirred for 20 h under argon. After completion of reaction (as determined by TLC, MeOH/CH$_2$Cl$_2$ 10:90, visualization with molybdato phosphoric acid) the precipitate was filtered using Hyflo (=diatomaceous earth) and the filtrate was washed with 10% NaHCO$_3$ and water. The organic phase was evaporated and the crude product obtained purified by preparative chromatography using a gradient of 0 to 8% methanol and methylene chloride with UV detection. The pure product was isolated by evaporation of the appropriate fractions as a white solid.

$^1$H NMR (CDCl$_3$): 0.84 (6H, m); 1.28 (6H, m); 1.57 (3H, m); 2.20 (6H, m); 2.52 (1H, m); 3.11 (1H, m); 3.42 (1H, m); 3.79 (4H, m); 4.28 (1H, m); 4.56 (1H, m); 5.31 (1H, m); 5.91 (1H, m); 6.32 (1H, m); 6.59 (2H, q).

Following the same procedure the following examples were prepared:

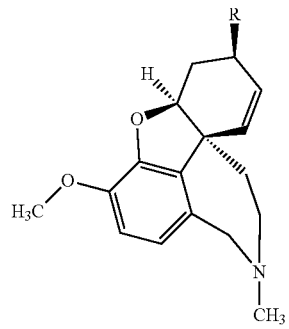

| Example No. | R | $^1$H NMR (CDCl$_3$) |
|---|---|---|
| 13 | 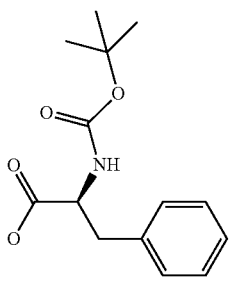 | 1.38 (9H, s); 1.67 (1H, m); 2.11 (2H, m); 2.48(3H, s); 2.59 (1H, m); 2.97 (2H, m); 3.29(2H, m); 3.78 (3H, s); 3.65 (2H, m); 4.10 (1H, m); 4.44 (1H, m); 5.31 (1H, m); 5.81 (1H, m); 6.34 (1H, m); 6.61 (2H, m); 7.19 (5H, m) |

-continued

| Example No. | R | ¹H NMR (CDCl₃) |
|---|---|---|
| 14 | 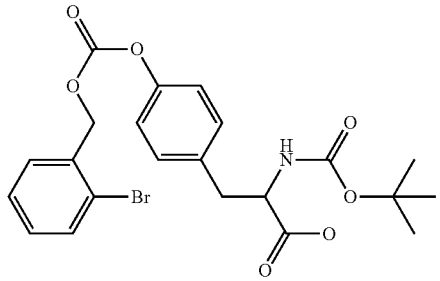 | 1.31 (9H, s); 1.54 (1H, m); 1.96(2H, m); 2.32(3H, s); 2.56 (1H, m); 3.01 (2H, m); 3.30(2H, m); 3.78 (3H, s); 3.65 (2H, m); 4.08 (1H, m); 4.42 (1H, m); 5.23 (1H, m); 5.38 (2H, m); 5.79 (1H, m); 6.28 (1H, m); 6.51 (2H, m); 7.13 (8H, m) |
| 15 | 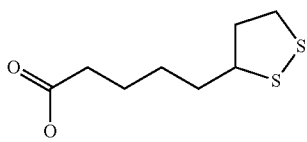 | 1.41 (2H, m); 1.61 (4H, m); 1.81 (1H, m); 2.03 (2H, m); 2.38 (6H, m); 2.69 (1H, m); 3.09 (3H, m); 3.30 (1H, m); 3.70 (1H, m); 3.83 (3H, s); 4.08 (1H, m); 4.55 (1H, m); 5.29 (1H, m); 5.90 (1H, q); 6.31 (1H, d), 6.63 (2H, m) |
| 16 | 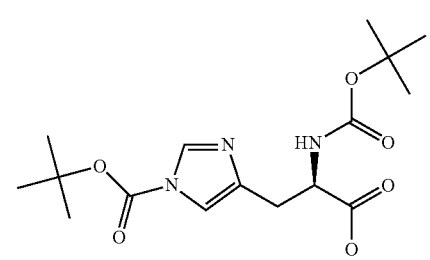 | 1.49 (9H, m): 1.54 (9H, m); 2.13 (2H, m); 2.49 (4H, m); 2.63 (1H, m); 3.17 (4H, m); 3.78 (5H, m); 4.57 (2H, m); 5.33 (1H, m); 6.07 (1H, m); 6.31 (1H, m); 6.63 (2H, q); 7.27 (2H, m) |
| 17 | 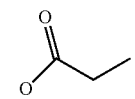 | 1.03 (3H, t); 1.54 (1H, m); 2.00 (2H, m); 2.25 (2H, m); 2.55 (3H, s); 2.64 (1H, m); 2.94 (1H, m); 3.02 (1H, m); 3.54 (1H, m); 3.76 (3H, s); 4.09 (1H, m); 4.48 (1H, m); 5.26 (1H, m); 5.76 (1H, m); 6.19 (1H, m); 6.56 (2H, q) |
| 18 | 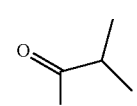 | 1.06 (6H, m); 1.41 (1H, m); 1.59 (1H, m); 2.05 (2H, m); 2.32 (3H, m); 2.53 (1H, m); 3.01 (1H, m); 3.23 (1H, m); 3.55 (1H, m); 3.78 (3H, s); 4.09 (1H, m); 4.48 (1H, m); 5.22 (1H, m); 5.83 (1H, m); 6.47 (1H, d); 6.60 (2H, q) |
| 19 | 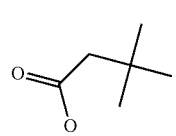 | 1.07 (9H, m); 1.51 (1H, m); 2.00 (2H, m); 2.26 (2H, m); 2.59 (3H, s); 2.54 (1H, m); 2.98 (1H, m); 3.02 (1H, m); 3.54 (1H, m); 3.76 (3H, s); 4.09 (1H, m); 4.48 (1H, m); 5.26 (1H, m); 5.81 (1H, m); 6.21 (1H, m); 6.62 (2H, q) |

Example 20

L-Phenylalanine, N-[(1,1-dimethylethoxy)carbonyl]-, (4aS,6S,8aS)-4a,5,9,10,11,12-hexahydro-3-methoxy-11-methyl-6H-benzofuro[3a,3,2-ef][2]benzazepin-6-yl ester To solution of (−) galantamine (287 mg, 1.0 mmol) in dry CH₂Cl₂ (30 mL) N-Boc-phenylalanine (400 mg, 1.5 mmol) and triphenyl phosphine (340 mg, 1.3 mmol) are added with magnetic stirring followed by the drop-wise addition of diisopropyl azodicarboxylate (DIAD) (270 mg, 1.34 mmoles.) to the reaction mixture at −10° C. The reaction was stirred overnight at room temperature under argon. After the completion of the reaction (TLC-MeOH/CH₂Cl₂ (10:90)) the reaction mixture was filtered and the filtrate was washed with 10% NaHCO₃ and water. The organic phase was evaporated and the crude product obtained purified by preparative chromatography using a gradient of 0 to 8% methanol and methylene chloride with UV detection. From the fractions containing the pure products these were isolated by evaporation of the solvents. This procedure results in the inversion of configuration on oxygen in position 6.

¹H NMR (CDCl₃) 1.35 (9H, s); 1.60 (1H, m); 2.05 (2H, m); 2.36 (3H, s); 2.59 (1H, m); 2.90 (2H, m); 3.30 (2H, m); 3.58 (3H, s); 3.65 (2H, m); 4.08 (1H, m); 4.42 (1H, m); 5.23 (1H, m); 5.79 (1H, m); 6.28 (1H, m); 6.54 (2H, m); 7.13 (5H, m)

Example 21

L-Phenylalanine, (4aS,6S,8aS)-4a,5,9,10,11,12-hexahydro-3-methoxy-11-methyl-6H-benzofuro[3a,3,2-ef][2]benzazepin-6-yl ester L-Phenylalanine, (4aS,6S,8aS)-4a,5,9,10,11,12-hexahydro-3-methoxy-11-methyl-6H-benzofuro[3a,3,2-ef][2]benzazepin-6-yl ester was prepared from the compound obtained in example 20 by Boc-deprotection using trifluoro acetic acid in methylene chloride followed by the usual workup and resulted in the product as a white powder.

$^1$H NMR (CDCl3) 1.82 (2H, m); 2.05 (2H, m); 2.36 (3H, s); 2.59 (1H, m); 2.90 (2H, m); 3.30 (2H, m); 3.58 (3H, s); 3.65 (2H, m); 4.08 (1H, m); 4.42 (1H, m); 5.23 (1H, m); 5.79 (1H, m); 6.28 (1H, m); 6.54 (2H, m); 7.13 (5H, m)

Example 22

L-tyrosine-(4aS,6R,8aS)-4a,5,9,10,11,12-hexahydro-3-methoxy-11-methyl-6H-benzofuro[3a,3,2-ef][2]benzazepin-6-yl ester L-tyrosine-(4aS,6R,8aS)-4a,5,9,10,11,12-hexahydro-3-methoxy-11-methyl-6H-benzofuro[3a,3,2-ef][2]benzazepin-6-yl ester was prepared from the compound of example 13 using the same deprotection method as in example 21.

$^1$H NMR (CDCl$_3$) 1.68 (2H, m); 1.96 (2H, m); 2.32 (3H, s); 2.56 (1H, m); 3.01 (2H, m); 3.30 (2H, m); 3.78 (3H, s); 3.65 (2H, m); 4.08 (1H, m); 4.42 (1H, m); 5.23 (1H, m); 5.79 (2H, m); 6.28 (1H, m); 6.51 (2H, m); 7.13 (4H, dd)

Example 23

L-histidine-(4aS,6R,8aS)-4a,5,9,10,11,12-hexahydro-3-methoxy-11-methyl-6H-benzofuro[3a,3,2-ef][2]benzazepin-6-yl ester hydrochloride L-histidine-(4aS,6R,8aS)-4a,5,9,10,11,12-hexahydro-3-methoxy-11-methyl-6H-benzofuro[3a,3,2-ef][2]benzazepin-6-yl ester hydrochloride was prepared from the compound of example 14 using HCl in ethyl acetate for deprotection and resulted in the isolation of the product as the hydrochloride.

$^1$H NMR (CDCl3) 2.34 (2H, m); 2.54 (4H, m); 2.78 (1H, m); 3.21 (4H, m); 3.79 (5H, m); 4.58 (2H, m); 5.41 (1H, m); 6.18 (1H, m); 6.48 (1H, m); 6.65 (2H, q); 7.38 (2H, m)

Example 24

(4aS,6R,8aS)-6H-Benzofuro[3a,3,2-ef][2]benzazepin-6-ol, 4a,5,9,10,11,12-hexahydro-3-methoxy-11-methyl-, hydrogen sulfate (ester)

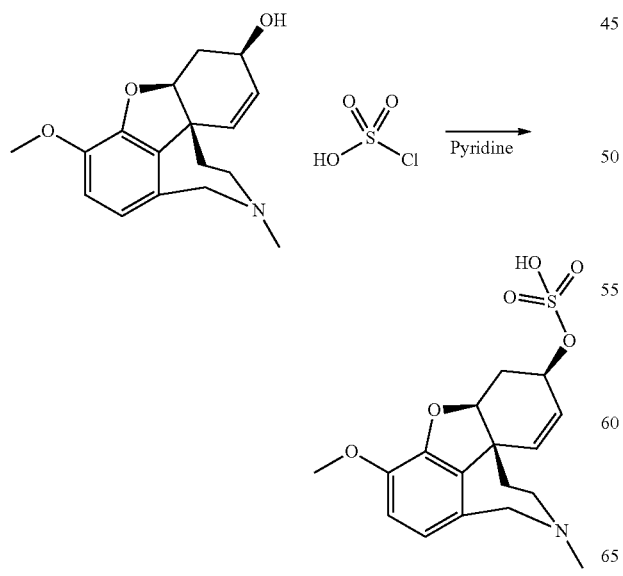

Chlorsulfonic acid (0.16 g, 1.39 mmol) was added to dry pyridine (1 ml) preheated to 70-80° C. and stirred at the same temperature for 30 min. A solution of galantamine (0.20 g, 0.70 mmol) in dry pyridine (1 ml) was added drop wise and the mixture was stirred overnight at room temperature with the formation of a precipitate. MeOH/H$_2$O 1:1 (5 ml) was added and the resulting clear solution was stirred for further 30 min. Volatiles were rotoevaporated and another portion of MeOH (5 ml) was added. The resulting fine precipitate was filtered to give (0.21 g, yield 82%, HPLC >99%) of product as a white powder.

IR: 1700.59, 1652.92, 1623.93, 1617.01, 1510.15, 1475.31, 1443.53, 1299.82, 1282.40, 1266.98, 1242.70, 1217.83, 1197.48, 1155.3, 1092.40, 1070.97, 1053.15, 1023.70, 1007.21, 984.45.

Example 25

General Procedure 1

To the solution of (−)-galantamine hydrobromide (1.0 mole) and triethyl amine (4.0 mol) in DCM (30 mL), DMAP (0.5 mol) was added followed by respective acid chloride or acid anhydride (1.2 mol). The mixture was stirred overnight at room temperature under argon. The reaction mixture was washed with 10% NaHCO$_3$ and brine, dried (Na$_2$SO$_4$) and concentrated. The crude compound obtained was purified by column chromatography or recrystallization to give the pure product.

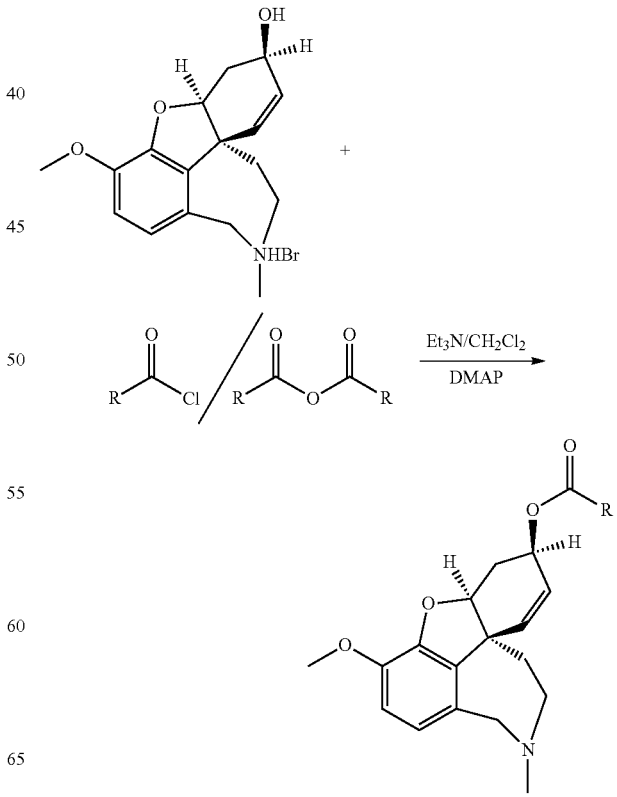

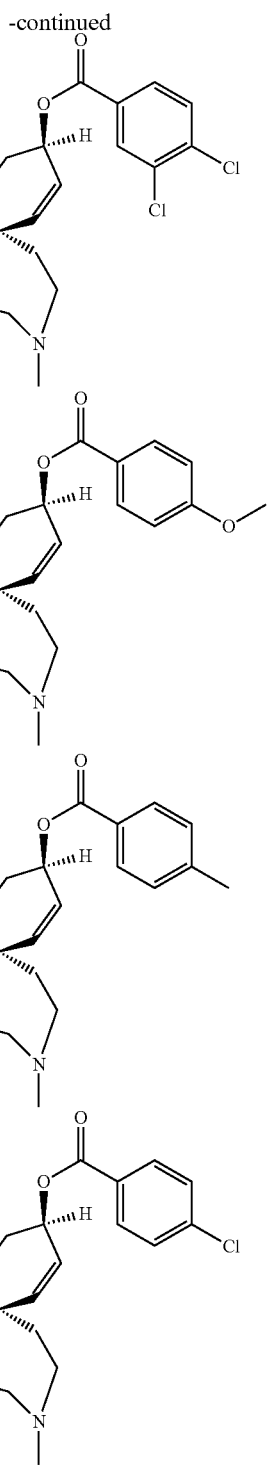

Using this procedure the following compounds were obtained:

O-Benzoyl-galantamine (=(4aS,6R,8aS)-4a,5,9,10,11,12-Hexahydro-3-methoxy-11-methyl-6H-benzofuro[3a,3,2-ef][2]benzazepin-6-ol, benzoate (ester)); yield: 78%

O-3,4-Dichlorobenzoyl-galantamine (=(4aS,6R,8aS)-4a,5,9,10,11,12-Hexahydro-3-methoxy-11-methyl-6H-benzofuro[3a,3,2-ef][2]benzazepin-6-ol, 3,4-dichlorobenzoate (ester)); off-white solid; mp. 69-70° C.

$^1$H NMR (200 MHz, CDCl$_3$) δ (ppm) 8.02 (d, J=1.88 Hz, 1H), 7.81 (dd, J=1.88 Hz, J=8.38 Hz, 1H), 7.38 (d, J=8.32 Hz, 1H), 6.62 (d, J=8.18 Hz, 1H), 6.52 (d, J=8.18 Hz, 1H), 6.32 (d, J=10.34 Hz, 1H), 5.89-5.97 (m, 1H), 5.51 (t, J=4.43 Hz, 1H), 4.58 (s, 1H), 4.07 (d, J=15.16 Hz, 1H), 3.18 (s, 3H), 3.61 (d, J=15.16 Hz, 1H), 3.21-3.45 (m, 1H), 2.96-3.05 (m, 1H), 2.66-2.76 (m, 1H), 2.34 (s, 3H), 2.0-2.19 (m, 2H), 1.51-1.59 (m, 1H).

O-4-Methoxybenzoyl-galantamine (=(4aS,6R,8aS)-4a,5,9,10,11,12-Hexahydro-3-methoxy-11-methyl-6H-benzofuro[3a,3,2-ef][2]benzazepin-6-ol, 4-methoxybenzoate (ester)); off-white solid; mp. 183-184° C.

$^1$H NMR (200 MHz, CDCl$_3$) δ (ppm) 8.01 (d, J=9.0 Hz, 2H), 8.56 (d, J=8.86 Hz, 2H), 6.69 (d, J=8.18 Hz, 1H), 6.58 (d, J=8.2 Hz, 1H), 6.35 (d, J=10.2 Hz, 1H), 6.0-6.07 (m, 1H), 5.56 (t, J=4.49 Hz, 1H), 4.66 (s, 1H), 4.15 (d, J=15.18 Hz, 1H), 3.89 (s, 3H), 3.84 (s, 3H), 3.68 (d, J=15.18 Hz, 1H), 3.29-3.53 (m, 1H), 3.04-3.12 (m, 1H), 2.73-2.81 (m, 1H), 2.41 (s, 3H), 2.08-2.26 (m, 2H), 1.58-1.66 (m, 1H).

O-4-Methylbenzoyl-galantamine (=(4aS,6R,8aS)-4a,5,9,10,11,12-Hexahydro-3-methoxy-11-methyl-6H-benzofuro[3a,3,2-ef][2]benzazepin-6-ol, 4-methylbenzoate (ester)); off-white solid; mp. 71-72° C.

$^1$H NMR (200 MHz, CDCl$_3$) δ (ppm) 7.94 (d, J=8.18 Hz, 2H), 7.17 (d, J=8.06 Hz, 2H), 6.69 (d, J=8.18 Hz, 1H), 6.58 (d, J=8.2 Hz, 1H), 6.35 (d, J=9.52 Hz, 1H), 6.0-6.08 (m, 1H), 5.57 (t, J=4.43 Hz, 1H), 4.66 (s, 1H), 4.17 (d, J=15.18 Hz, 1H), 3.89 (s, 3H), 3.70 (d, J=15.18 Hz, 1H), 3.31-3.43 (m, 1H), 3.06-3.13 (m, 1H), 2.74-2.83 (m, 1H), 2.42 (s, 3H), 2.38 (s, 3H), 2.08-2.26 (m, 2H), 1.59-1.67 (m, 1H).

O-4-Chlorobenzoyl-galantamine (=(4aS,6R,8aS)-4a,5,9,10,11,12-Hexahydro-3-methoxy-11-methyl-6H-benzofuro[3a,3,2-ef][2]benzazepin-6-ol, 4-chlorobenzoate (ester)); off-white solid; mp. 72-74° C.

$^1$H NMR (200 MHz, CDCl$_3$) δ (ppm) 7.91 (d, J=8.74 Hz, 2H), 7.27 (d, J=8.72 Hz, 2H), 6.62 (d, J=8.2 Hz, 1H), 6.52 (d, J=8.2 Hz, 1H), 6.30 (d, J=10.34 Hz, 1H), 5.92-6.0 (m, 1H), 5.5 (t, J=4.36 Hz, 1H), 4.59 (s, 1H), 4.09 (d, J=15.18 Hz, 1H), 3.82 (s, 3H), 3.63 (d, J=15.18 Hz, 1H), 3.23-3.46 (m, 1H), 2.99-3.06 (m, 1H), 2.66-2.76 (m, 1H), 2.35 (s, 3H), 2.0-2.2 (m, 2H), 1.52-1.6 (m, 1H).

O-2-Thenoyl-galantamine (=(4aS,6R,8aS)-4a,5,9,10,11,12-Hexahydro-3-methoxy-11-methyl-6H-benzofuro[3a,3,2-ef][2]benzazepin-6-ol, thiophene-2-carboxylate (ester)); off-white solid; mp. 115-116° C.

$^1$H NMR (200 MHz, CDCl$_3$) δ (ppm) 7.78 (dd, J=1.2 Hz, J=3.8 Hz, 1H), 7.51 (dd, J=1.34 Hz, J=4.96 Hz, 1H), 7.04 (dd, J=3.76 Hz, J=4.98 Hz, 1H), 6.69 (d, J=8.18 Hz, 1H), 6.59 (d, J=8.04 Hz, 1H), 6.35 (d, J=10.2 Hz, 1H), 6.02 (dd, J=4.7 Hz, J=10.2 Hz, 1H), 5.54 (t, J=4.49 Hz, 1H), 4.63 (s, 1H), 4.18 (d, J=15.02 Hz, 1H), 3.87 (s, 3H), 3.71 (d, J=15.18 Hz, 1H), 3.31-3.5 (m, 1H), 3.07-3.14 (m, 1H), 2.73-2.83 (m, 1H), 2.42 (s, 3H), 2.04-2.26 (m, 2H), 1.6-1.68 (m, 1H).

O-5-Chloro-2-thenoyl-galantamine (=(4aS,6R,8aS)-4a,5,9,10,11,12-Hexahydro-3-methoxy-11-methyl-6H-benzofuro[3a,3,2-ef][2]benzazepin-6-ol, 5-chlorothiophene-2-carboxylate (ester)); off-white solid; mp. 58-59° C.

$^1$H NMR (200 MHz, CDCl$_3$) δ (ppm) 7.5 (d, J=4.04 Hz, 1H), 7.80 (d, J=4.02 Hz, 1H), 6.62 (d, J=8.04 Hz, 1H), 6.52 (d, J=8.06 Hz, 1H), 6.31 (d, J=10.2 Hz, 1H), 5.92 (dd, J=4.57 Hz, J=10.2 Hz, 1H), 5.45 (t, J=4.36 Hz, 1H), 4.56 (s, 1H), 4.08 (d, J=15.16 Hz, 1H), 3.81 (s, 3H), 3.61 (d, J=15.18 Hz, 1H), 3.21-3.34 (m, 1H), 2.97-3.04 (m, 1H), 2.64-2.74 (m, 1H), 2.34 (s, 3H), 1.97-2.19 (m, 2H), 1.5-1.57 (m, 1H).

Example 26

General Procedure 2

To the solution of the corresponding acid acid (13.87 g, 135.8 mmol) in DCM (250 mL) was added DCC (33.62 g, 162.9 mmol) followed by DMAP (3.32 g, 27.15 mmol), reaction mixture was stirred for additional 30 minutes at room temperature. To this (−)-galantamine hydrobromide (10.0 g, 27.15 mmol) and triethyl amine (4.6 mL, 32.59 mmol) was added, the mixture was stirred overnight at room temperature under argon. The precipitated DCHU was removed by filtration and the filtrate was evaporated. The additional DCHU was removed by subsequent trituration with cold ethyl acetate and filtration. The ethyl acetate solution was roto-evaporated and the crude product obtained was purified by column chromatography to give the desired product.

2-Methyl-butanoyl-galantamine (=(4aS,6R,8aS)-4a,5,9,10,11,12-Hexahydro-3-methoxy-11-methyl-6H-benzofuro[3a,3,2-ef][2]benzazepin-6-ol, 2-methyl-butanoate (ester)) was obtained in 53% yield as a solid using the general procedure 2.

The same product, identical in every respect (HPLC, m.p., 1H-NMR), was also obtained in 58% yield using the general procedure 1.

2-Methyl-propanoyl-galantamine (=(4aS,6R,8aS)-4a,5,9,10,11,12-Hexahydro-3-methoxy-11-methyl-6H-benzofuro[3a,3,2-ef][2]benzazepin-6-ol, 2-methyl-propanoate (ester)) was obtained in 63% yield as a solid using the general procedure 1.

2-Methyl-propanoyl-galantamine hydrochloride salt

To the solution of 2-methyl-propanoyl-galantamine (150 mg, 0.43 mmol) in ethyl acetate (5 mL), ethyl acetate saturated with HCl (5 mL) was added slowly with stirring at 0° C. The reaction mixture was stirred at room temperature for 1 h. Solvent was evaporated and the residue obtained was washed with dry ether and was dried under high vacuum to give 164 mg (97%) of desired product as an off-white solid.
Anal. calcd for $C_{21}H_{27}NO_4$ (1.5 HCl): C, 61.2; H, 6.97; N, 3.40. Found: C, 61.62; H, 6.95; N, 3.91.

2-Methyl-propanoyl-galantamine citric acid salt

To the solution of 2-methyl-propanoyl-galantamine (150 mg, 0.43 mmol) in methanol (5 mL), a solution of citric acid in methanol (5 mL) was added slowly with stirring at room temperature. The reaction mixture was stirred at room temperature for 1 h. Solvent was evaporated and the residue obtained was precipitated from methanol-diethyl ether and was dried under high vacuum to give 187 mg (81%) of desired product as a off-white solid.
Anal. calcd for $C_{27}H_{35}NO_{11}$ (1.0H$_2$O): C, 57.14; H, 6.57; N, 2.47. Found: C, 57.43; H, 6.48; N, 2.53.

Example 27

General Procedure 3

To a stirred solution of (−)-galantamine hydrobromide (1.10 mmol) in pyridine (6 mL) at 0° C. under nitrogen, the corresponding acid chloride (2.2 mmol) was added and the mixture was stirred until a TLC showed the reaction to be complete. Then $CH_2CL_2$ (10 mL) and water (10 mL) were added and stirring was continued for 30 min. The organic layer was separated, washed with water (2×10 mL), dried over anhydrous $MgSO_4$ and the solvent removed. The residue was purified by flash chromatography giving the product identical in all respects to O-Benzoyl-galantamine.

Example 28

Synthesis of R1-pyridinoyl-galantamine

In addition to the examples provided above, the following compounds were prepared by the described general procedures:

TABLE 6

| MF | MW | Substituent R1 |
| --- | --- | --- |
| $C_{21}H_{25}NO_4$ | 355.43 | cyclopropanecarboxylate |
| $C_{24}H_{23}Cl_2NO_4$ | 460.3 | 3,4-dichlorobenzoate |
| $C_{28}H_{33}NO_4$ | 447.57 | 4-tert-butylbenzoate |
| $C_{25}H_{23}ClF_3NO_4$ | 493.91 | 4-chloro-3-(trifluoromethyl)benzoate |
| $C_{25}H_{23}F_3N_2O_6$ | 504.46 | 4-nitro-3-(trifluoromethyl)benzoate |
| $C_{25}H_{24}F_3NO_4$ | 459.47 | 4-(trifluoromethyl)benzoate |
| $C_{24}H_{23}Cl_2NO_4$ | 460.36 | 2,4-dichlorobenzoate |
| $C_{24}H_{24}N_2O_6$ | 436.47 | 4-nitrobenzoate |
| $C_{24}H_{24}ClNO_4$ | 425.92 | 3-chlorobenzoate |
| $C_{25}H_{24}F_3NO_4$ | 459.47 | 3-(trifluoromethyl)benzoate |
| $C_{24}H_{24}N_2O_6$ | 436.47 | 3-nitrobenzoate |
| $C_{24}H_{23}Cl_2NO_4$ | 460.36 | 3,5-dichlorobenzoate |
| $C_{26}H_{30}N_2O_4$ | 434.54 | 3-(dimethylamino)benzoate |
| $C_{25}H_{27}NO_4$ | 405.50 | 3-methylbenzoate |
| $C_{24}H_{24}ClNO_4$ | 425.92 | 2-chlorobenzoate |
| $C_{24}H_{23}F_2NO_4$ | 427.45 | 2,4-difluorobenzoate |
| $C_{24}H_{23}Cl_2NO_4$ | 460.36 | 2,5-dichlorobenzoate |
| $C_{24}H_{24}FNO_4$ | 409.46 | 4-fluorobenzoate |
| $C_{26}H_{30}N_2O_4$ | 434.54 | 4-(dimethylamino)benzoate |
| $C_{24}H_{26}N_2O_4$ | 406.49 | 4-aminobenzoate |
| $C_{27}H_{32}N_2O_4$ | 448.57 | 4-(dimethylamino)-3-methylbenzoate |
| $C_{25}H_{25}NO_6$ | 435.48 | 2H-1,3-benzodioxole-5-carboxylate |
| $C_{26}H_{27}NO_5$ | 433.51 | 4-acetylbenzoate |
| $C_{22}H_{23}NO_4S$ | 397.50 | thiophene-3-carboxylate |
| $C_{21}H_{23}N_3O_4$ | 381.44 | 1H-imidazole-5-carboxylate |
| $C_{21}H_{22}N_2O_5$ | 382.42 | 1,3-oxazole-5-carboxylate |
| $C_{21}H_{22}N_2O_4S$ | 398.48 | 1,3-thiazole-5-carboxylate |
| $C_{21}H_{22}N_2O_4S$ | 398.48 | 1,3-thiazole-2-carboxylate |
| $C_{26}H_{27}NO_6$ | 449.51 | 2-(acetyloxy)benzoate |

Example 29

Preparation of Mouse Brain Homogenate

The brain is removed from the animal (mouse), shock frozen in liquid nitrogen and stored at minus 80° C. until use. Before preparing the extract, the frozen brain is thawed on ice and the weight is determined. Ice cold buffer (130 mM NaCl, 5 mM KCl, 2.5 mM $CaCl_2$, 1 mM $MgCl_2$, 5 mM Glucose, 5 mM HEPES, pH 7.4) is added to the thawed mouse brain (1:4, weight to volume, resulting in a 20% brain homogenate). The tissue is then homogenized in a potter homogeniser on ice, moving the piston up and down 11 times at 240 rpm. The freshly prepared mouse brain homogenate is divided into aliquots.

Example 30

Procedure for Measuring the Inhibition of Brain Esterase. Results Shown as FIG. 1

A modified Ellmann's esterase test is used. Briefly the method relies on the cleavage of the substrate acetylthiocholine to acetate and thiocholine. The latter reacts with DTNB (5,5'-Dithiobis-(2-nitro-benzoicacid) to a yellow compound, which can be quantified spectrometrically. The incubation buffer contains 51 mmol/l sodium phosphate buffer and 0.05% Tween 20, at pH 7.2 and is supplemented with 100 mg/l DTNB, and 0.2% mouse brain homogenate (prepared as described in Example 29). The compound to be investigated is added to the desired concentration. The mixture is brought to 37° C. and the reaction is started by addition of 200 µM acetylthiocholine. $A_{405}$ is measured in is intervals in a microplate reader for 40 s. The linear parts of the absorption-time-curves represent the starting speed of the enzymatic reaction and are used for the calculation of the reaction speed. The slope of the curve corresponds to the reaction speed. The inhibition is expressed as percent of the non inhibited reaction according to following equation:

$$\% \text{ Inhibition}=100*(1-(\text{Slope}_{inhibited}/\text{Slope}_{noninhibited})).$$

Example 31

Procedure for Determination of Prodrug Cleavage in Mouse Brain Homogenate.

To aliquots of mouse brain homogenate as prepared according to Example 13 pro-galantamine derivatives are added and adjusted to a final concentration of 10 µM of the prodrug. At the end of the incubation time, 12 µl 0.1 M NaOH and 100 µl saturated KCl are added to the 0.1 ml reaction mixture and mixed thoroughly. The remaining prodrug and the released galantamine are extracted by 200 µl toluene. The toluene extraction step is repeated twice using 150 µl toluene and the obtained extracts are pooled, dried, dissolved in 50% Methanol and used for subsequent HPLC analysis.

Example 32

Investigation of the allosteric modulation effect of drug candidates on nicotinic acetylcholine receptors (nAChRs) expressed in HEK-293 cells by electrophysiology. Results shown as FIG. 4.

Single HEK-293 cells expressing either human α4β2, human α3β4, or chimeric chicken α7 (with mouse $5HT_3$) nAChR were plated on fibronectin-coated cover slips for 3 days before measurement. The selected nAChR containing cells were placed in the recording bath, filled with extracellular buffer (145 mM NaCl, 5 mM KCl, 1 mM $MgCl_2$, 2 mM $CaCl_2$, 10 mM D-glucose, 10 mM HEPES, pH 7.3, approximately 300 mOsm). Patch-clamp system consisted of an inverted microscope (Zeiss, Germany), computer-controlled patch-clamp amplifier with PatchMaster software (HEKA, Germany), tubing perfusion system (ALA, USA) together with a U-tube applicator (IMM, Germany) and dual micromanipulators. The patch pipettes were pulled from fire-polished, 100 mm long and 1.5 mm width, single borosilicate glass capillaries (WPI, Germany). A programmable puller (Sutter, USA) was used to prepare a twin pair of ready for use pipettes. Each patch pipette (resistance 4-8 MΩ) was used only once. Pipettes were filled with an internal buffer (140 mM CsCl, 11 mM EGTA, 10 mM HEPES, 2 mM $MgCl_2$, pH 7.3, approximately 300 mOsm) and connected to the working electrode. Working and reference electrodes for experiments were made from daily renewed, freshly chlorinated silver wire (40 mm×0.4 mm) and were connected to a headstage circuit of the patch-clamp amplifier. Patching was done using rectangular test pulses with an amplitude of −1 mV and a duration of 20 ms. Immediately after formation of the gigaseal the holding potential of −70 mV was applied to the patch electrode and whole-cell recordings were established by using negative pressure pulses. All necessary compensations for fast and slow membrane capacitance and serial resistance transients were automatically set within the PatchMaster software. Whole-cell currents were evoked by the application of nicotine at the $EC_{50}$ for each appropriate nAChR subtype (α4β2 and α3β4 $EC_{50}$=30 µM, chimeric α7 $EC_{50}$=3 µM). To evaluate an allosteric potentiating ligand (APL) effect of selected compounds on each subtype of nAChR, they were added to stimulating nicotine solutions at the following concentrations: 1, 5, 10, 50, 100, 500, 1,000, 5,000 and 10,000 nM, and solutions were applied to the cell surface during 500 ms pulses through the U-tube, and then corresponding currents, digitized to 10 kHz, were recorded for 10 s. Consecutive current stimulations were done with a 2 min interval to avoid nAChR desensibilisation and to ensure full exchange of stimulating solutions. The averaged peak amplitudes of the currents, measured in the presence of selected compound concentrations, were compared with those determined in the absence of compounds (control) and they were calculated as % of control. The measurements of an APL effect of particular compound were repeated on a minimum of five cells to obtain the mean values+/−SD. Mean values of the observed APL effect, which did not exceed 15% were treated as insignificant. To present a concentration-dependent APL effect of particular compound, the corresponding % of control values+/−SD were plotted against the concentrations used.

Example 33

Pharmacokinetics of Pro-Galantamine Gln-1062 (3 mg/kg) in the Mouse. (Results Shown as FIG. 5.)

Study Objective

Determination of the pharmacokinetic profiles of Gln-1062 and its cleavage product galantamine in blood and brain. Determine the brain-to-blood concentration ratios of Gln-1062 and its cleavage product galantamine, and assess the blood-brain barrier penetration capacities.

Study Plan

Bioanalysis

Analytical method for estimation of Gln-1062 was evaluated for its linearity, precision & accuracy and recovery in SAM blood and brain homogenate using LC/MS/MS.

LC/MS/MS Parameters

The parameters of chromatographic conditions and extraction conditions for the Gln-1062 and Galantamine analysis were Chromatographic Parameters:

Column: Phenomenex Synergi, Polar-RP 80 A, C18, 75×2.0 mm, 4µ

Mobile Phase

Mobile Phase Buffer: 40 mM Ammonium Formate, pH 3.5

Aqueous Reservoir (A): 10% Buffer, 90% Water

Organic Reservoir (B): 10% Buffer, 90% Acetonitrile

Flow rate: 0.450 mL/min

Gradient Programme:

| Time (min) | Gradient Curve | % A | % B |
|---|---|---|---|
| 0 | 1 | 100 | 0 |
| 1.2 | 1 | 60 | 40 |
| 3 | 1 | 0 | 100 |
| 3.1 | 1 | 100 | 0 |
| 5 | 1 | 100 | 0 |

Divert Valve Time Schedule:

| Time (min) | Divert Valve | |
| --- | --- | --- |
| | Waste | MS |
| 0 | x | |
| 1.2 | | x |
| 4.5 | x | |

Run time: 5.0 min
Column oven temperature: Ambient
Auto sampler temperature: Ambient
Auto sampler Wash: Water:acetonitrile:isopropanol with 0.2% formic acid, 1:1:1(v/v/v)

| Retention time: | Gln-1062: | $3.33 \pm 0.05$ min. |
| --- | --- | --- |
| | Galantamine: | $2.44 \pm 0.05$ min |
| | Metoprolol: | $2.80 \pm 0.05$ min. |

Mass Parameters (API 3200):
Mode: MRM
Polarity: Positive
Ion source: Turbo spray
Analyte: Gln-1062 (Q1 Mass 392.4; Q3 Mass 213.2)
    Galantamine (Q1 Mass 288.3; Q3 Mass 213.1)
ISTD: Metoprolol (Q1 Mass 268.4; Q3 Mass 116.2)
Source/Gas Parameters:

| Curtain gas (CUR) | 10 |
| --- | --- |
| Collision gas (Collision associated Dissociation) CAD | 5 |
| Ion Spray Voltage (IS) | 5500 V |
| Temperature (TEM) | 575° C. |
| GS1 | 55 |
| GS2 | 45 |
| Ihe | ON |

Compound Parameters:

| Parameter | Galantamine | Metoprolol | Gln-1062 |
| --- | --- | --- | --- |
| Declustering Potential (V) | 45 | 35 | 50 |
| Entrance Potential (V) | 10 | 10 | 10 |
| Collision Cell Entrance Potential (V) | 20 | 20 | 20.00 |
| Collision Energy (eV) | 32 | 26 | 32 |
| Collision Cell Exit Potential (V) | 4.5 | 2 | 5 |
| Dwell Time (milliSec) | 200 | 200 | 200 |

Extraction Procedure:

The Extraction procedure, including preparation of STD, QC and study samples, and preparation of calibration curve standards for recovery is shown in FIGS. 8, (A) and (B).

Method Evaluation

This method was evaluated for linearity, precision & accuracy and recovery of Gln-1062 in SAM blood and brain homogenate.

A. Linearity, Precision & Accuracy

A single standard curve and six replicates each of three quality control (QC) levels (18 total QCs) were extracted and analyzed. The linearity of the calibration curve was determined by a weighed least square regression analysis.

Acceptance Criteria i. At least six out of nine standards must have an accuracy of ±15% from nominal, except at the lower limit of quantitation (LLOQ) where ±20% is acceptable.

ii. Two-thirds of the batch QCs and at least half of the QCs at each level must have a calculated accuracy of ±15% from nominal.

iii. Intra-assay Mean Precision and Accuracy
   1. Four out of six QCs must be available to determine accuracy and precision.
   2. The intra-assay coefficient of variation (% CV) of each QC level must not exceed 15% and the accuracy of the mean value for each validation to be accepted.

Gln-1062 linearity, precision and accuracy in blood and brain homogenate matrices were evaluated.

B. Recovery

The recovery of Gln-1062 from the blood and brain homogenate matrices were also evaluated.

Recovery was determined by quantifying the concentration of the analytes in extracted matrix QC samples with a standard curve prepared in post-extract (blank extracts) sample matrix as described above in section B of the extraction procedure, entitled "Preparation of Calibration Curve Standards for Recovery."

Gln-1062 recovery in blood and brain homogenate matrices were evaluated.

Animal Study
Study Design

| Animal | Test item | Dose (mg/kg) | Dose Conc. (mg/mL) | Dose Volume (mL/kg) | Dose route | No. of Animals for each time point | Sample time points (hr) |
| --- | --- | --- | --- | --- | --- | --- | --- |
| Male SAM 25-33 gm | Gln-1062 | 3 | 0.2 | 15 | i.v, bolus (tail vein) | 3 | Predose, 0.05, 0.10, 0.17, 0.33, 0.50, 0.83, 1.33, 2.0 and 4.0 |

Sample Collection

Collection of Blood:

Blood samples were collected from the retro-orbital plexus. 0.5 ml of blood was collected into a pre-labeled polypropylene micro centrifuge tube containing sodium citrate as the anticoagulant, and kept on ice.

Blood was mixed gently with anticoagulant and an aliquot of 50 µL of blood sample immediately precipitated as described above in section A of the extraction procedure, entitled "Preparation of STD, QC and Study Samples." Remaining volume of blood sample at each time point frozen on dry ice.

All the blood samples were transferred to analytical department and frozen at −80±10° C. until analysis.

Collection of Brain:

Immediately after blood withdrawal, brain was perfused with phosphate buffer saline (pH 7.4), removed and frozen on dry ice.

All the brain samples were transferred to analytical department and frozen at −80° C. until analysis.

Brain Homogenate Preparation:

Brain samples were thawed on ice and weighed. n appropriate volume ice cold homogenizing media (methanol: water::20:80,v/v) added. n ice, homogenized the brain sample with the polytron homogenizer and make up the volume with homogenizing media to get 1 gm of brain per 4 mL of homogenate. After homogenizing, immediately freezed the brain homogenate samples at −80° C. until analysis.

Example 34

Behavioural index for gastro-intestinal side effects in ferrets following application of galantamine and several R1-pro-galantamines, respectively. Results shown in FIG. 6.

Test System

Fourteen adult male *Putoris furo* ferrets (Marshall BioResources (North Rose, USA)), weighting 750-1000 grams on the day of experimentation were used in the present study. In agreement with the sponsor four out of the fourteen animals were included in two experimental groups, ferrets #1, 2, 3 and 4).

Animal Housing

The acclimatization of the animals lasted at least 5 days. At receipt, animals were collectively housed in cages at Syncrosome's premises. They had free access to food and drinking water ad libitum.

Test Item and Reference Compound

During this study, one reference compound (Galantamine) and one Galantos candidate compound (GLN979) were tested at two doses each. Both compounds were administered I.P. at doses and concentrations.

Details of the different compound shipments are presented in Table 7.

TABLE 7

| | Receipt | | |
|---|---|---|---|
| Compound | Nov. 11$^{th}$, 2007 | Nov., the 21$^{st}$, 2007 | Nov., the 29$^{th}$, 2007 |
| Galantamine | 48.0 mg | 256.0 mg (One vial) | — |
| GLN979 | 48.0 mg | — | 262.6 mg |
| 2-Hydroxy propyl-β-cyclodextrin | U.I: (One vial) | 7.3 g + 7.3 g (Two vials) | ≈4.7 g + ≈5.0 g |
| NaCl | U.I: (One vial) | 3.0 g (One vial) | — |

As requested by the sponsor, the same vehicle (15% 2-Hydroxypropyl-β-cyclodextrin/96 mM NaCl) was used for both Galantamine and GLN979 preparation. A detailed solubilization protocol was sent by mail by Galantos to Syncrosome and received on Nov. 5, 2007.

Test Compound (GLN979)

| Nature | GLN979. |
|---|---|
| Molar mass | U.I. |
| Administration dose | 20 and 40 mg/kg B.W. |
| Administration route | I.P. |
| Vehicle | 15% 2-Hydroxypropyl-β-cyclodextrin/96 mM NaCl. |

Reference Compound (Galantamine)

| Nature | Galantamine |
|---|---|
| Molar mass | U.I. |
| Administration dose | 3 and 20 mg/kg B.W. |
| Administration route | I.P. |
| Vehicle | 15% 2-Hydroxypropyl-β-cyclodextrin/96 mM NaCl. |

I.P. Administrations

For the 4 experimental groups, the administrations were performed in unanaesthetized animals through the I.P. route at $T_0$.

Emesis Test

After I.P. administration of the compound solution, the animals were continuously observed by a trained technician for four hours. During that period, the number of episodes of vomiting (series of retches leading to the expulsion of part of the gastro-intestinal content) were recorded.

Behavioural Observation

During the 4 hours-observation period, several side-effects (salivation, shivering, respiratory problems and diarrhea) were also observed. For each of these behaviours, a scoring method was determined with the sponsor. Depending on its severity, each parameter were quantified as:

"None" (None): Behaviour not observed.

"Moderate" (Mod.): Behaviour observed with a low frequency and/or a low intensity.

"Intense" (Int.): Behaviour observed frequently and/or continuously and/or at a high intensity.

Inclusion Criteria

All the animals receiving I.P. administration of the reference or the test compound were included in the study regardless of the pattern of both their emetic responses and behavious.

Example 35

Reversal from scopolamine-induced amnesia in mice, results shown as FIG. 6

Drug Preparation

Gln 1062, Gln 0979 and galantamine were dissolved in 15%—hydroxypropyl-β-cyclodextrin in 96 mM NaCl (isotonic) supplied by the sponsor. Gln 1062 and Gln 0979 were used in concentrations of 0.01, 0.03, 0.1 and 0.2 mg/ml, which when given in a volume of 10 ml/kg result in doses of 0.1, 0.3, 1 and 2 mg/kg i.p., respectively. Galantamine was used in concentrations of 0.03, 0.1, 0.2 and 0.5 mg/ml, which when given in a volume of 10 ml/kg result in doses of 0.3, 1, 2 and 5 mg/kg i.p., respectively.

Control animals received 15%—hydroxypropyl-β-cyclodextrin in 96 mM NaCl injection as a vehicle.

Nicotine ((−)-Nicotine hydrogen tartrate salt, Sigma, France), scopolamine (−(−)scopolamine hydrochloride, Sigma, France) were dissolved in saline (0.9% NaCl, Aguettant, France) at the concentration of 0.04 and 0.1 mg/ml, respectively. They were administrated at a dosage volume of 10 ml/kg to achieve doses of 0.4 and 1 mg/kg, respectively.

Test Animals

Four to five week old male CD-1 mice (Janvier; Le Genest St Isle—France) were used for the study.

They were group-housed (10 mice per cage) and maintained in a room with controlled temperature (21-22° C.) and a reversed light-dark cycle (12 h/12 h; lights on: 17:30-05:30; lights off: 05:30-17:30) with food and water available ad libitum.

Experimental Design

The potential cognitive enhancing property of Gln 1062, Gln 0979 and galantamine were evaluated in scopolamine-treated mice in the T-maze alternation model under the same experimental conditions. Both Gln 1062 and Gln 0979 were tested in doses of 0.1, 0.3, 1 and 2 mg/kg i.p. Galantamine was tested in doses 0.1, 0.3, 1, 2 and 5 mg/kg i.p. Nicotine was tested in a dose of 0.4 mg/kg i.p. All these compounds were administered immediately after the injection of 1 mg/kg i.p. scopolamine (20 min prior to the T-maze trial) used to induce memory deficit.

Memory performance was assessed by the percentage of spontaneous alternation in the T-maze. The number of alternation in saline-injected mice was used as the base level of unaltered memory performance.

Mice were housed 10 per cage. Each mouse in a cage was randomly assigned by a unique number (1 to 10) written on the tail with permanent ink.

Gln 1062, Gln 0979 and galantamine were tested separately in three set of experiments with different animals. Each set of experiments was divided in series of daily experiments that always comprises at least one representative of each of Saline/vehicle, Scopolamine/vehicle and Scopolamine/Nicotine (0.4 mg/kg) groups.

Measurement

The T-maze apparatus was made of gray Plexiglas with a main stem (55 cm long×10 cm wide×20 cm high) and two arms (30 cm long×10 cm wide×20 cm high) positioned at 90 degree angle relative to the left and right of the main stem. A start box (15 cm long×10 cm wide) was separated from the main stem by a guillotine door. Horizontal doors were present to close off specific arms during the force choice alternation task.

The experimental protocol consists of one single session, which starts with 1 "forced-choice" trial, followed by 14 "free-choice" trials. In the first "forced-choice" trial, the animal is confined 5 s in the start arm and then released while either the left or right goal arm is blocked by a horizontal door. After the mouse is released, it will negotiate the maze and eventually enter the open goal arm, and return to the start position. Immediately after the return of the animal to the start position, the closed goal door is opened and the animal is now free to choose between the left and right goal arm ("free choice trials"). The animal is considered as entered when it places its four paws in the arm. A session is terminated and the animal is removed from the maze as soon as 14 free-choice trials have been performed or 10 min have elapsed, whatever event occurs first. The average duration of a trial is 6 min.

The apparatus is cleaned between each animal using alcohol (70°). Urine and feces are removed from the maze.

During the trials, animal handling and the visibility of the operator are minimized as much as possible.

The percentage of alternation over the 14 free-choice trials was determined for each mouse and was used as an index of working memory performance. This percentage was defined as entry in a different arm of the T-maze over successive trials (i.e., left-right-left-right, etc).

Statistical Analysis

Analysis of variance (ANOVA) was performed on the result data. Fisher's Protected Least Significant Difference was used for pairwise comparisons. p value≤0.05 were considered significant. The drug induced reversion of scopolamine-induced memory deficit was calculated by setting the respective response of the saline/vehicle group as 100% and the scopolamine/vehicle group as 0% reversion.

In order to determine the $ED_{50}$ for each drug, the recovery performance was plotted following a sigmoidal dose-response model (graphpad software). ED50 was read from the curve fitting table and represents the effective dose associated with 50% of response.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A method for the treatment of a neurodegenerative, psychiatric or neurological disease associated with a cholinergic deficit comprising administering GLN-1062:

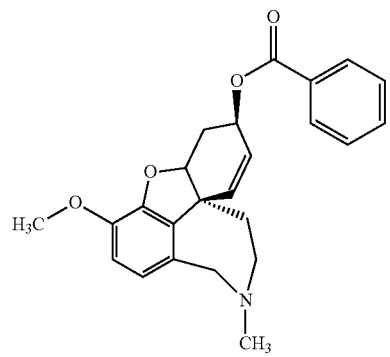

or a pharmaceutically acceptable salt thereof by nasal administration to a patient in need thereof.

2. The method of claim 1, wherein the disease is selected from the group consisting of Alzheimer's disease, Parkinson's disease, other types of dementia, schizophrenia, epilepsy, stroke, poliomyelitis, neuritis, oxygen and nutrient deficiencies in the brain after hypoxia, anoxia, asphyxia, cardiac arrest, chronic fatigue syndrome, various types of poisoning, anesthesia, spinal cord disorders, central nervous system inflammation, postoperative delirium and/or subsyndronal postoperative delirium, neuropathic pain, subsequences of the abuse of alcohol and drugs, addictive alcohol and nicotine craving, and subsequences of radiotherapy.

3. The method of claim 1, wherein the neurodegenerative, psychiatric or neurological disease is selected from the group consisting of Alzheimer's disease, Parkinson's disease, dementia, schizophrenia, stroke, central nervous system inflammation and epilepsy.

4. The method of claim 1, wherein GLN-1062 is administered in a pharmaceutical composition as a suspension.

5. The method of claim 1, wherein GLN-1062 is administered in a pharmaceutical composition as a solution.

6. The method of claim 4, wherein the suspension comprises 0.5 to 30 wt % GLN-1062.

7. The method of claim 5, wherein the solution comprises 0.5 to 30 wt % GLN-1062.

8. The method of claim 1, comprising multiple doses to the patient, wherein a single dose comprises between 0.1 and 20 mg of GLN-1062.

* * * * *